United States Patent [19]

Klemarczyk et al.

[11] 4,357,246

[45] Nov. 2, 1982

[54] CARBOALKOXY ALKYL NORBORNANES, ORGANOLEPTIC USES THEREOF AND PROCESS FOR PREPARING SAME

[75] Inventors: Philip T. Klemarczyk, Old Bridge; James M. Sanders, Eatontown; Manfred H. Vock, Locust; Joaquin F. Vinals, Red Bank; Frederick L. Schmitt, Holmdel; Edward J. Granda, Englishtown, all of N.J.

[73] Assignee: International Flavors & Fragrances Inc., New York, N.Y.

[21] Appl. No.: 303,162

[22] Filed: Sep. 17, 1981

Related U.S. Application Data

[60] Division of Ser. No. 206,466, Nov. 13, 1980, Pat. No. 4,312,888, which is a continuation-in-part of Ser. No. 133,870, Mar. 25, 1980, Pat. No. 4,319,036.

[51] Int. Cl.³ .............................................. D06M 13/18
[52] U.S. Cl. ..................................................... 252/8.6
[58] Field of Search ........................................ 252/8.6

[56] References Cited

U.S. PATENT DOCUMENTS

| | | | |
|---|---|---|---|
| 4,053,657 | 10/1977 | Schreiber et al. | 426/538 |
| 4,089,986 | 5/1978 | Light et al. | 426/538 |
| 4,151,309 | 4/1979 | Diglit et al. | 426/538 |
| 4,218,347 | 8/1980 | Waf et al. | 426/538 |

Primary Examiner—Maria Parrish Tungol
Attorney, Agent, or Firm—Arthur L. Liberman

[57] ABSTRACT

Described is a process for augmenting or enhancing the aroma or taste of a foodstuff or chewing gum comprising the step of adding to a foodstuff or chewing gum an aroma augmenting or enhancing quantity of a product comprising a major proportion of compounds defined according to the structure:

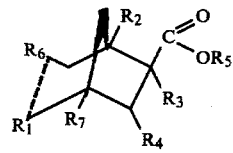

2 Claims, 67 Drawing Figures

MASS SPECTRUM FOR EXAMPLE I.

GLC PROFILE FOR EXAMPLE II.

GLC PROFILE EXAMPLE I.

NMR SPECTRUM FOR EXAMPLE I, FRACTION 8.

IR SPECTRUM FOR EXAMPLE I, FRACTION 2.

NMR SPECTRUM FOR EXAMPLE I, FRACTION 2.

IR SPECTRUM FOR EXAMPLE I, FRACTION 8.

NMR SPECTRUM FOR EXAMPLE II, PEAK 1.

NMR SPECTRUM FOR EXAMPLE II, FRACTION 6.

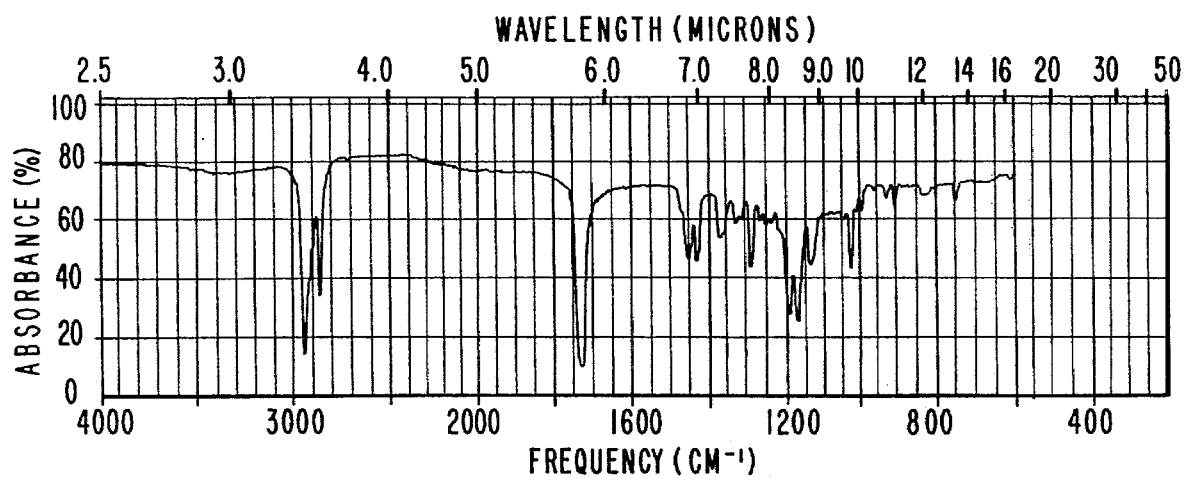
IR SPECTRUM FOR EXAMPLE II, PEAK I.
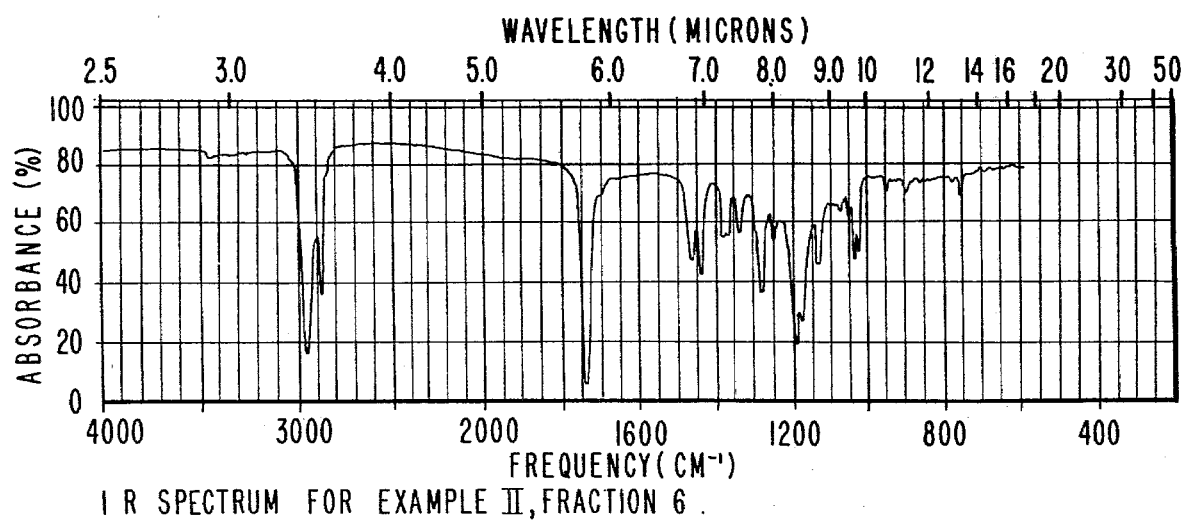
IR SPECTRUM FOR EXAMPLE II, FRACTION 6.

GLC PROFILE FOR EXAMPLE VI.

GLC PROFILE FOR EXAMPLE II.

GLC PROFILE FOR EXAMPLE III.

NMR SPECTRUM FOR EXAMPLE III, FRACTION 10.

MASS SPECTRUM EXAMPLE V.

NMR SPECTRUM FOR EXAMPLE III, FRACTION 6.

IR SPECTRUM FOR EXAMPLE III, FRACTION 10.

IR SPECTRUM FOR EXAMPLE III, FRACTION 6.

MASS SPECTRUM FOR EXAMPLE III.

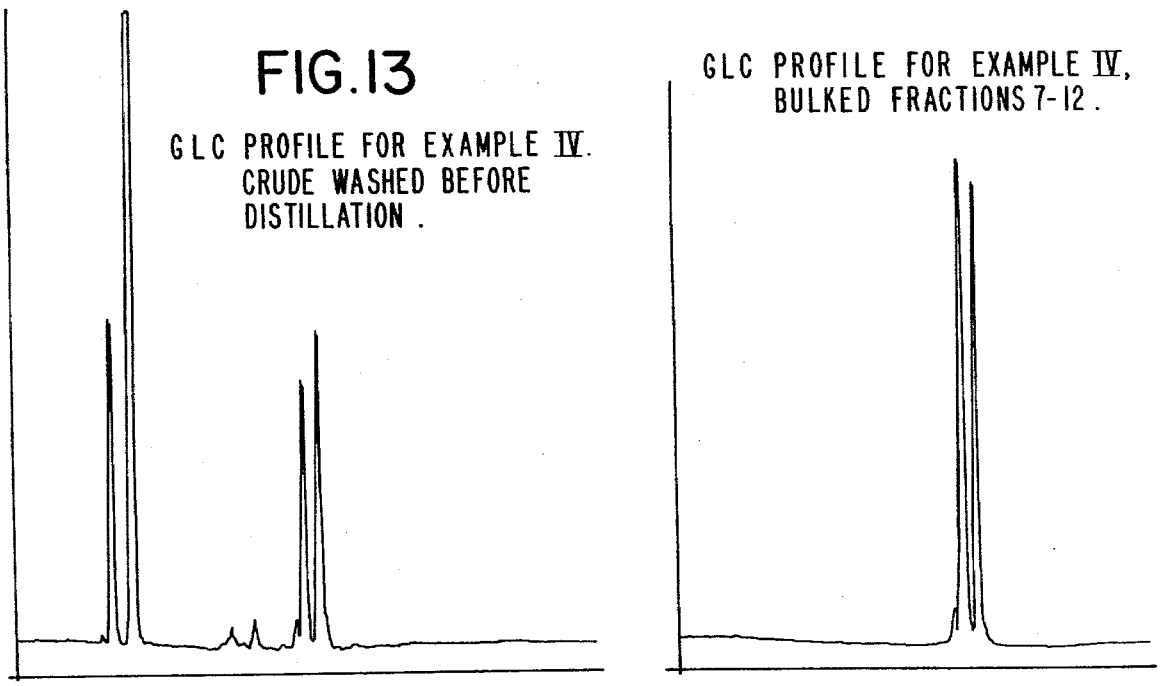
FIG. 13
GLC PROFILE FOR EXAMPLE IV. CRUDE WASHED BEFORE DISTILLATION.
FIG. 14
GLC PROFILE FOR EXAMPLE IV, BULKED FRACTIONS 7-12.
FIG. 15 A
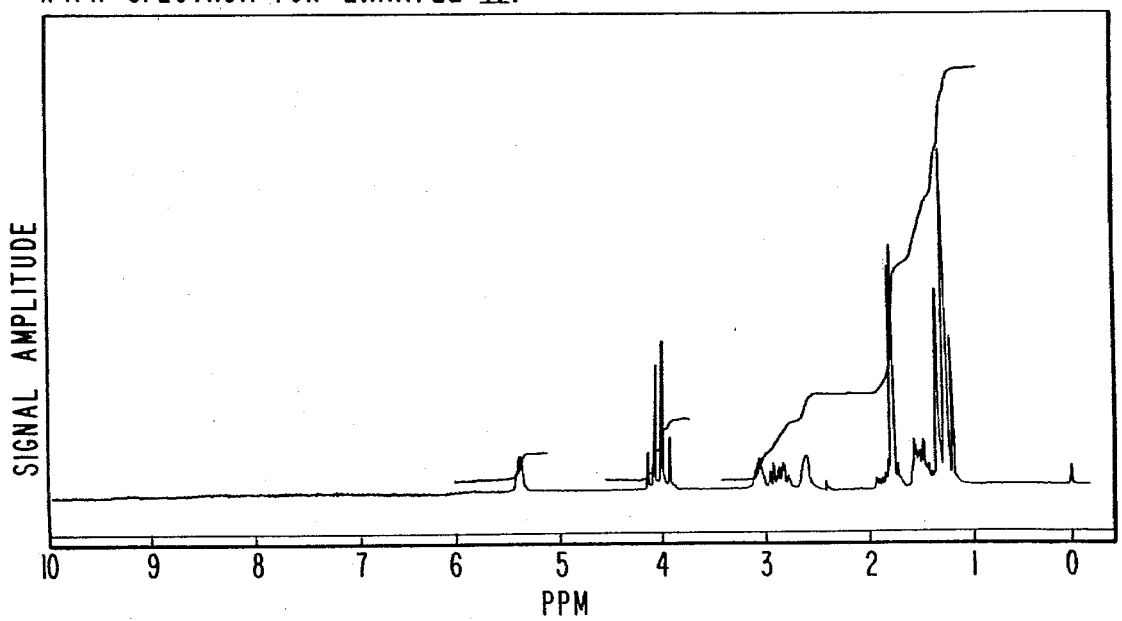
NMR SPECTRUM FOR EXAMPLE IV.

NMR SPECTRUM FOR EXAMPLE IV.

IR SPECTRUM FOR EXAMPLE IV.

IR SPECTRUM FOR EXAMPLE IV.

MASS SPECTRUM EXAMPLE IV.

GLC PROFILE EXAMPLE V.

NMR SPECTRUM FOR EXAMPLE V, FRACTION 9.

NMR SPECTRUM FOR EXAMPLE V, FRACTION 1.

I R SPECTRUM FOR EXAMPLE V, FRACTION 9.

I R SPECTRUM FOR EXAMPLE V, FRACTION 1.

NMR SPECTRUM FOR EXAMPLE VI, FRACTION 14.

NMR SPECTRUM FOR EXAMPLE VI, FRACTION 4.

IR SPECTRUM FOR EXAMPLE VI, FRACTION 14.

IR SPECTRUM FOR EXAMPLE VI, FRACTION 4.

MASS SPECTRUM FOR EXAMPLE VI.

GLC PROFILE FOR EXAMPLE VII.

NMR SPECTRUM FOR EXAMPLE VII.

IR SPECTRUM FOR EXAMPLE VII.

MASS SPECTRUM FOR EXAMPLE VII

GLC PROFILE FOR EXAMPLE XXXII.

GLC PROFILE FOR EXAMPLE VII-A.

NMR SPECTRUM FOR EXAMPLE VII-A, FRACTION I.

MASS SPECTRUM FOR EXAMPLE VII-A, PEAK 2.

NMR SPECTRUM FOR EXAMPLE VII-A, PEAK 2.

IR SPECTRUM FOR EXAMPLE VII-A, FRACTION 1

IR SPECTRUM FOR EXAMPLE VII-A, PEAK 2.

MASS SPECTRUM EXAMPLE VII-A FRACTION I.

NMR SPECTRUM FOR PEAK 1 OF EXAMPLE XXXII.

NMR SPECTRUM FOR PEAK 2 OF EXAMPLE XXXII.

PPM

IR SPECTRUM FOR PEAK 1 OF EXAMPLE XXXII.

IR SPECTRUM FOR PEAK 2 OF EXAMPLE XXXII.

GLC PROFILE FOR EXAMPLE XXXV, (BEFORE DISTILLATION)

GLC PROFILE FOR EXAMPLE XXXIII.

NMR SPECTRUM FOR FRACTION I, PEAK I OF EXAMPLE XXXIII.

IR SPECTRUM FOR EXAMPLE XXXIV.

NMR SPECTRUM FOR FRACTION 8, PEAK 2 OF EXAMPLE XXXIII.

IR SPECTRUM FOR PEAK I, FRACTION I OF EXAMPLE XXXIII.

IR SPECTRUM FOR FRACTION 8, PEAK 2 OF EXAMPLE XXXIII.

NMR SPECTRUM FOR PEAK 1, FRACTION 2 OF EXAMPLE XXXIV.

NMR SPECTRUM FOR EXAMPLE XXXIV.

IR SPECTRUM FOR FRACTION 2, PEAK 1 OF EXAMPLE XXXIV.

NMR SPECTRUM FOR PEAK 1, EXAMPLE XXXV.

NMR SPECTRUM FOR PEAK 2 OF EXAMPLE XXXV.

IR SPECTRUM FOR PEAK 1 OF EXAMPLE XXXV.

IR SPECTRUM FOR PEAK 2, OF EXAMPLE XXXV.

CARBOALKOXY ALKYL NORBORNANES, ORGANOLEPTIC USES THEREOF AND PROCESS FOR PREPARING SAME

This is a divisional of application Ser. No. 206,466, filed 11/13/80 now U.S. Pat. No. 4,312,888, which in turn, is a continuation-in-part of application for U.S. Letters Patent, Ser. No. 133,870 filed 3/25/80 now U.S. Pat. No. 4,319,036.

BACKGROUND OF THE INVENTION

The present invention relates to carboalkoxy alkyl norbornanes having the generic formula:

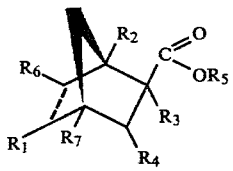

wherein the dashed line represents either a carbon-carbon single bond or a carbon-carbon double bond; $R_1$, $R_2$, $R_3$, $R_4$, $R_6$ and $R_7$ represents hydrogen or methyl; with the proviso that one of $R_1$, $R_2$, $R_6$ and $R_7$ is methyl and each of the other of $R_1$, $R_2$, $R_6$ and $R_7$ is hydrogen; and with the further proviso that $R_3$ and $R_4$ are not both methyl, produced by the novel process of our invention, and to novel compositions using one or more of such norbornane derivatives to alter, modify or enhance the flavor and/or aroma of consumable materials or impart flavor and/or aroma to consumable materials.

There has been considerable work performed relating to substances which can be used to impart (modify, augment or enhance) flavors and fragrances to (or in) various consumable materials. These substances are used to diminish the use of natural material, some of which may be in short supply, and to provide more uniform properties in the finished product.

Fruity, burnt fruit-like, raspberry, sweet, seedy, berry-like, red berry-like, blueberry-like, spicy, black pepper-like, herbaceous, clove-like, vermouth-like, strawberry-like, wild strawberry-like, camphoraceous and balsamic aromas with fruity burnt fruit-like, raspberry, seedy, sweet, berry-like, red berry-like, blueberry-like, spicy, black pepper-like, herbaceous, clove-like, vermouth-like, strawberry-like, wild strawberry-like, camphoraceous, balsamic and bitter tastes are particularly desirable for many uses in foodstuff flavors, chewing gum flavors, toothpaste flavors and medicinal product flavors.

Spicy, cooling, clove-like, cinnamon bark-like, sweet, fruity, berry-like, juicyfruit, woody, piney, blueberry, banana, green, herbaceous, strawberry-like and dill aroma and taste characteristics both prior to and on smoking in the mainstream and in the side stream.

Intense and pleasant fruity, strawberry-like, raspberry, Reseda body-like, banana-like, creamy, camphoraceous, herbaceous, sweet, spicy, woody, eucalyptol-like, rum/butterscotch-like, balsamic, green, minty, borneol-like and "medicinal" aromas with strong camphor, minty and calamnus-like undertones are desirable in several types of perfume compositions, perfumed articles and colognes.

Arctander, "Perfume and Flavor Chemicals", 1969, Volume I discloses the use in perfume compositions and in foodstuff flavors of camphene carbinyl acetate thus:
"1029: 2,2-Dimethyl-Delta-2-beta-norbornane-2-ethylacetate "Camphene Carbinyl acetate".

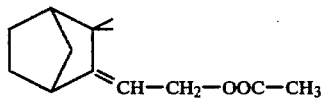

Mild and sweet-woody odor with a floral-piney undertone. The commercial products are probably not well defined single chemicals, and great variations in odor have been observed. This ester has been developed in line with the research on Sandalwood type odors. The parent alcohol "Camphene carbinol" was once considered useful as a Sandalwood type material, but is has found more use as a sweetening and enriching ingredient in sophisticated Pine fragrances. The title ester finds limited use in perfume compositions of woody character, Fougeres, Pine fragrances, etc. and it blends very well with the Cyclohexanol derivatives, Ionones, iso-Bornyl-acetate, Nitromusks, etc."

Mellor and Webb, J. Chem. Soc. Perkin Trans II, 1974 (I) 26-31 discloses production of the compounds having the structures:

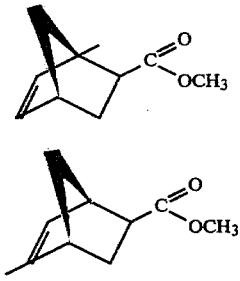

together with several other methyl substituted isomers thereof in admixture, according to the reaction:

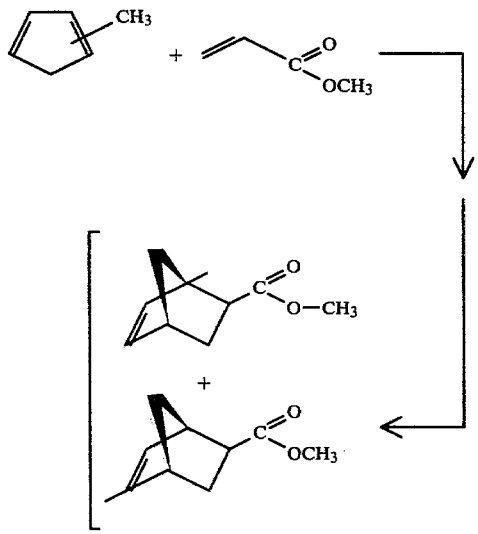

The Mellor and Webb article however, does not disclose the reaction to take place at low temperatures in the pressence of an alkyl aluminum halide or dialkyl aluminum halide whereby but two isomers are produced in a controlled fashion in high yields thus yielding an organoleptically acceptable mixture of carboalkoxy norbornane derivatives.

Thus, nothing in the prior art indicates production for organoleptic uses of compounds having the generic structure:

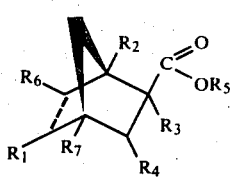

wherein the dashed line represents a carbon-carbon single bond or a carbon-carbon double bond and $R_1$, $R_2$, $R_3$, $R_4$, $R_5$, $R_6$ and $R_7$ are as defined above.

U.S. Pat. No. 4,143,074 discloses, generically, compounds which are esters and contain the norbornyl moiety having the structures:

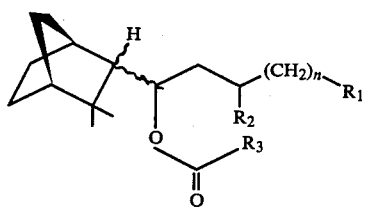

wherein either or both of $R_1$ or $R_2$ is hydrogen or lower alkyl, $R_3$ is hydrogen or lower alkyl and n is zero or 1 and in addition, the compound having the structure:

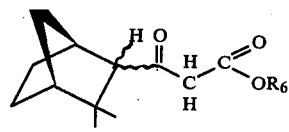

wherein $R_6$ is alkyl having from one up to eight carbon atoms.

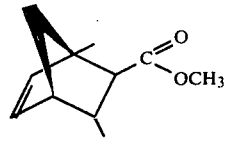

and

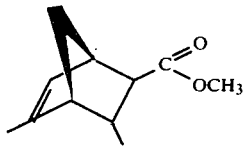

Figure 2A:
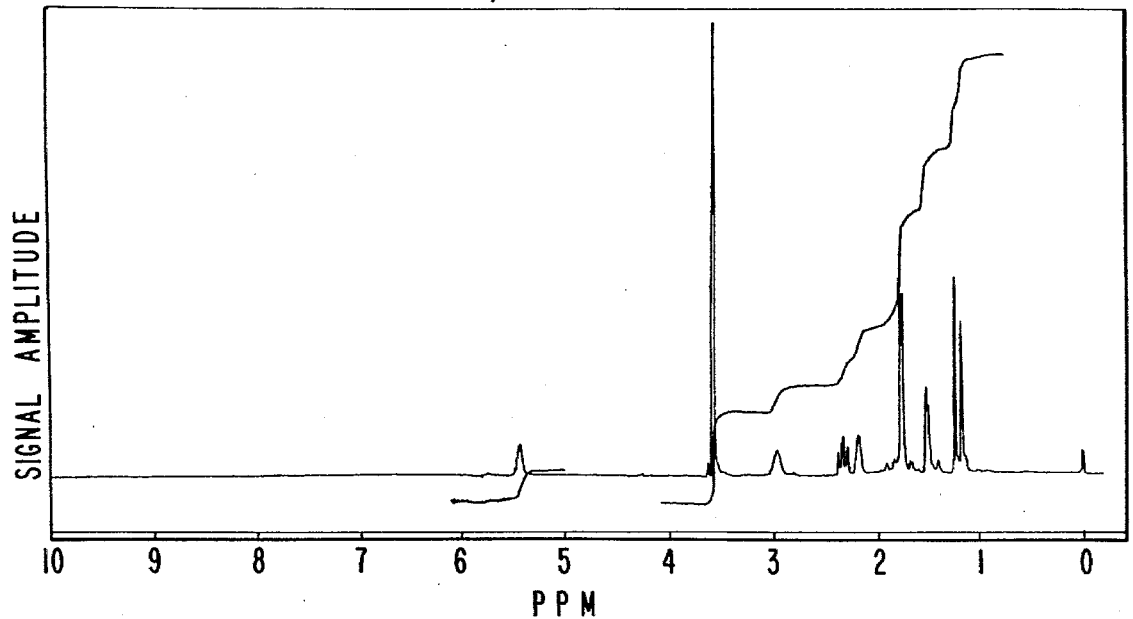

FIG. 2A is the NMR spectrum for fraction 8 of the distillation product of the reaction product of Example I having the structure:

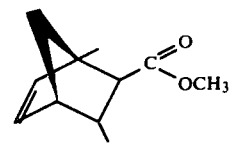

Figure 2B:
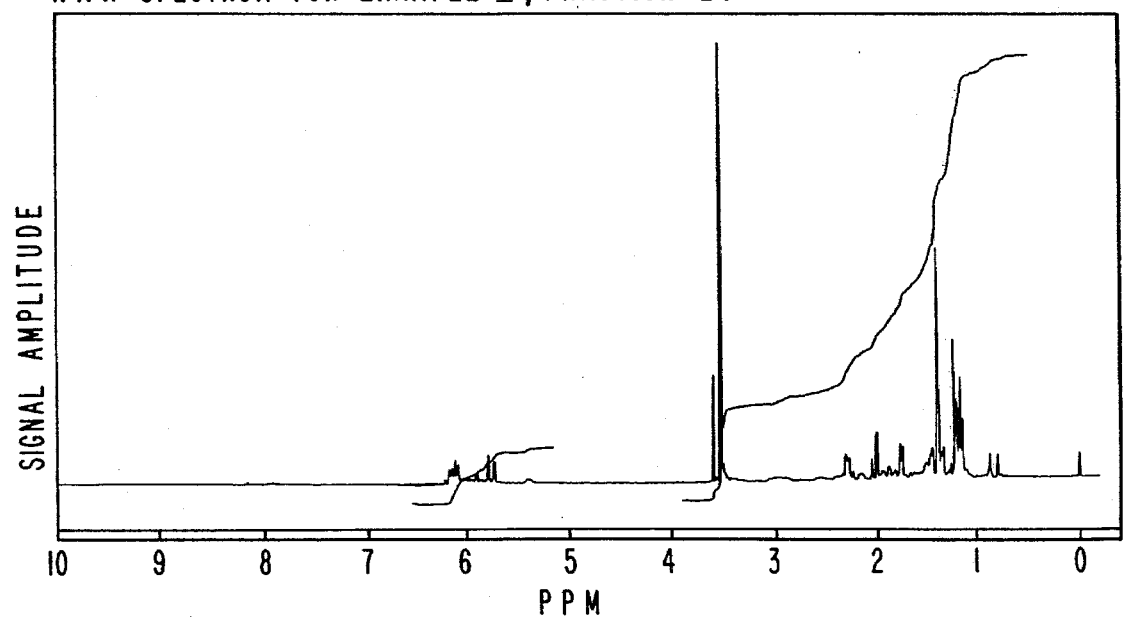

FIG. 2B represents the NMR spectrum for fraction 2 of the distillation product of the reaction product of Example I having the structure:

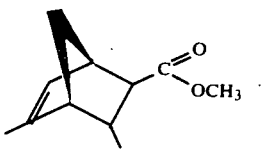

Figure 3B:
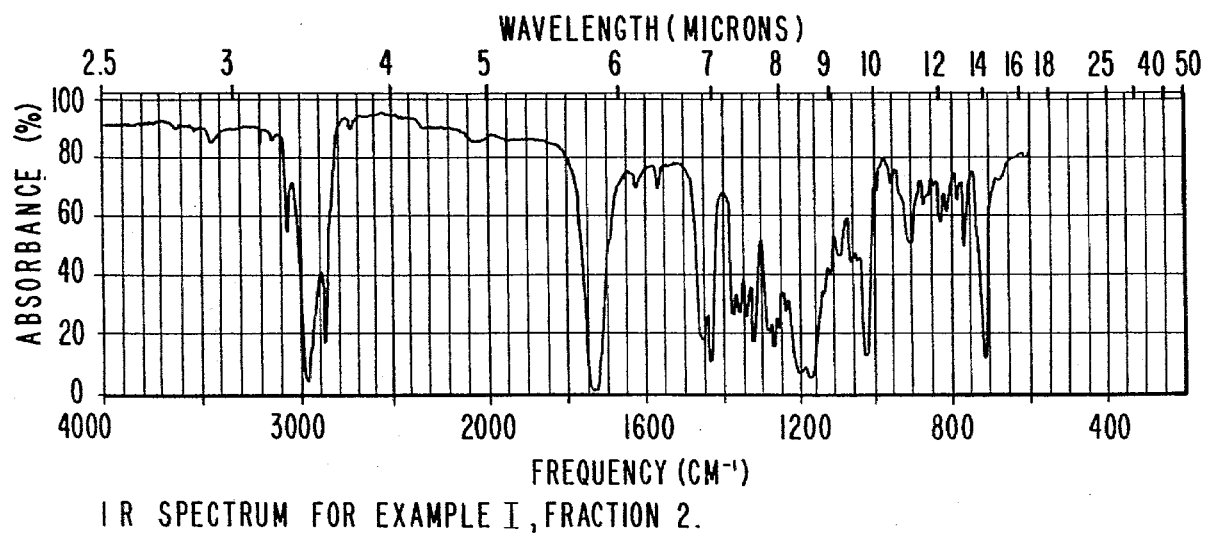
Figure 3A:
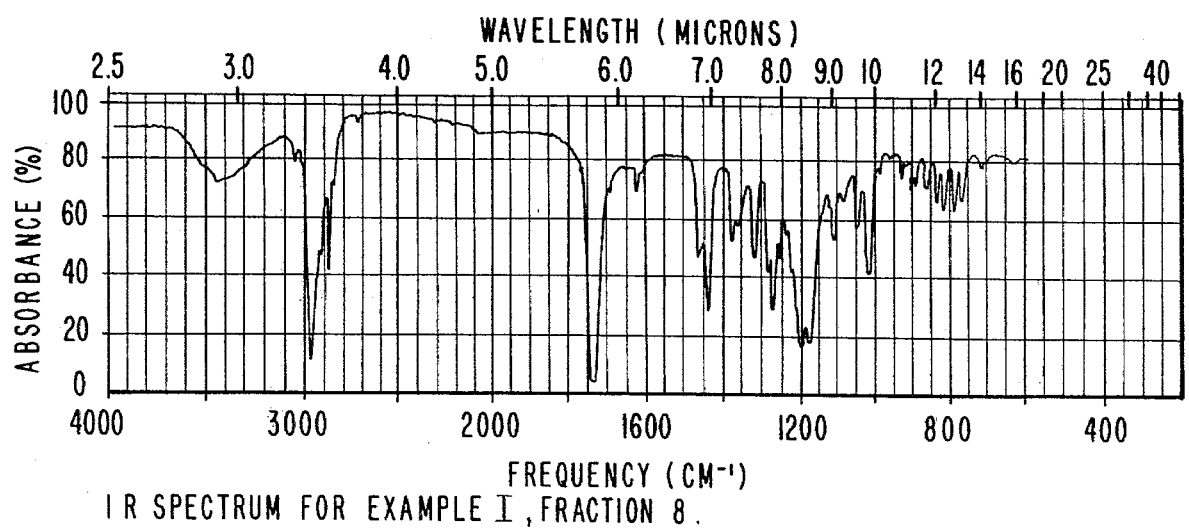

FIG. 3A represents the infrared spectrum for fraction 8 of the distillation product of the reaction product of Example I having the structure:

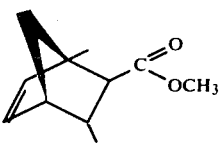

FIG. 3B represents the infrared spectrum for fraction 2 of the distillation product of the reaction product of Example I having the structure:

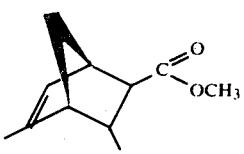

Figure 4:
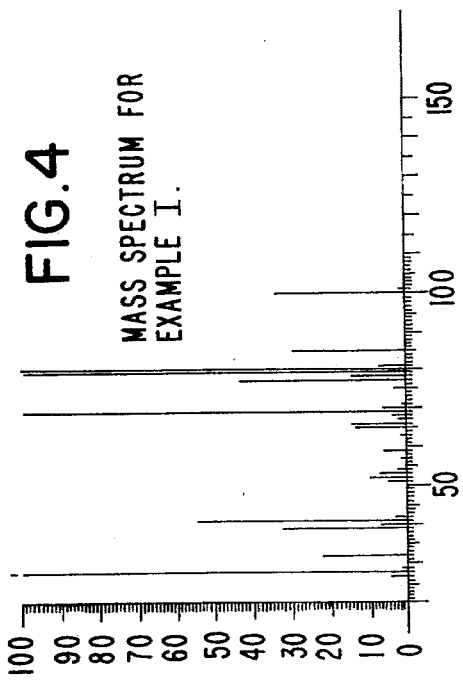

FIG. 4 represents the mass spectrum for the reaction product of Example I containing compounds having the structures:

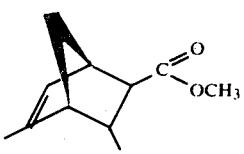

and

-continued

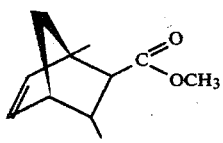

Figure 5:
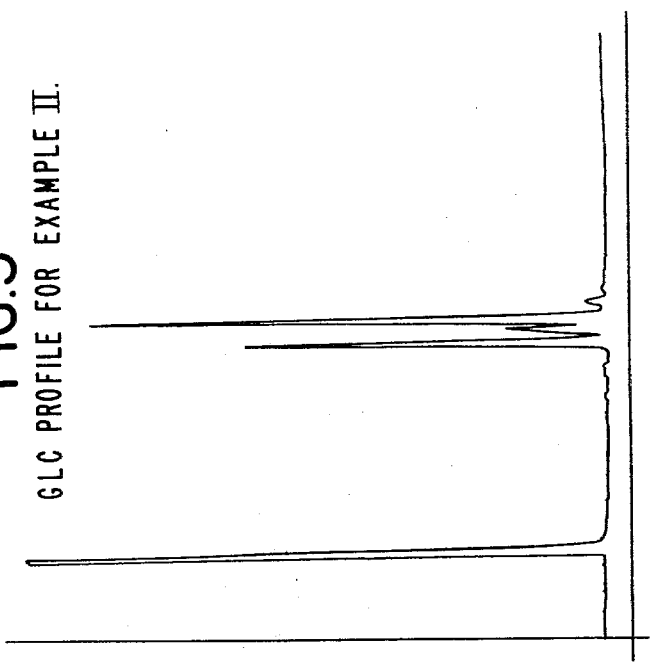

FIG. 5 represents the GLC profile for the reaction product of Example II containing compounds having the structures:

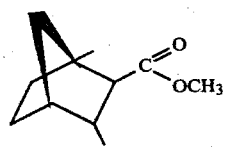

and

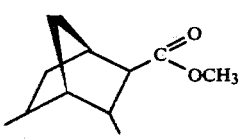

Figure 6A:
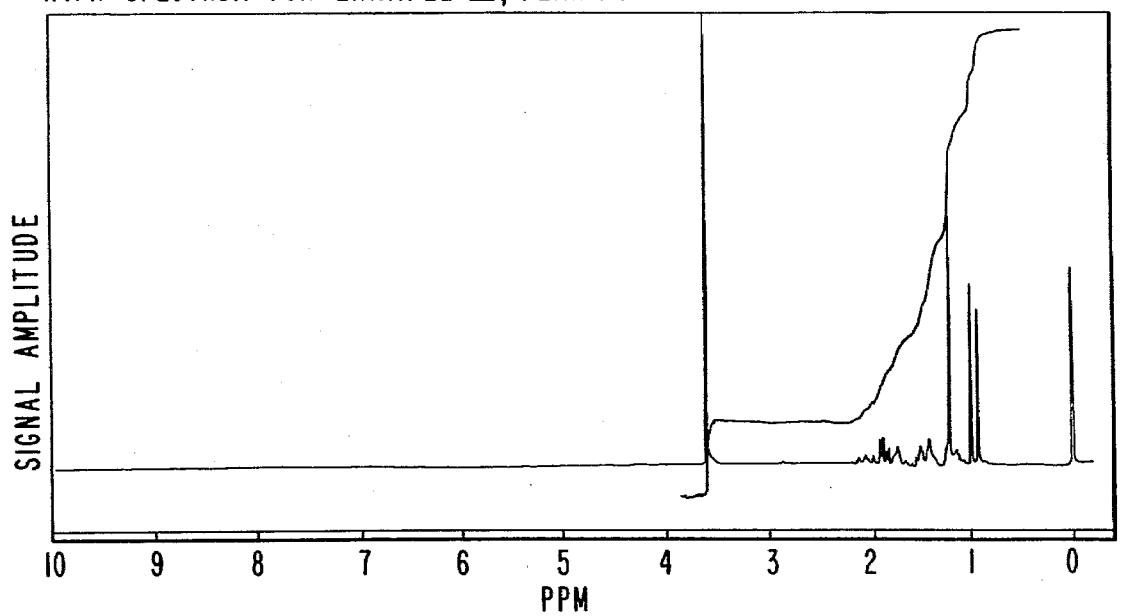

FIG. 6A represents the NMR spectrum of peak 1 of the GLC profile of FIG. 5 consisting essentially of the compound having the structure:

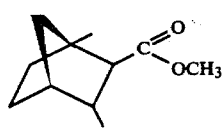

Figure 6B:
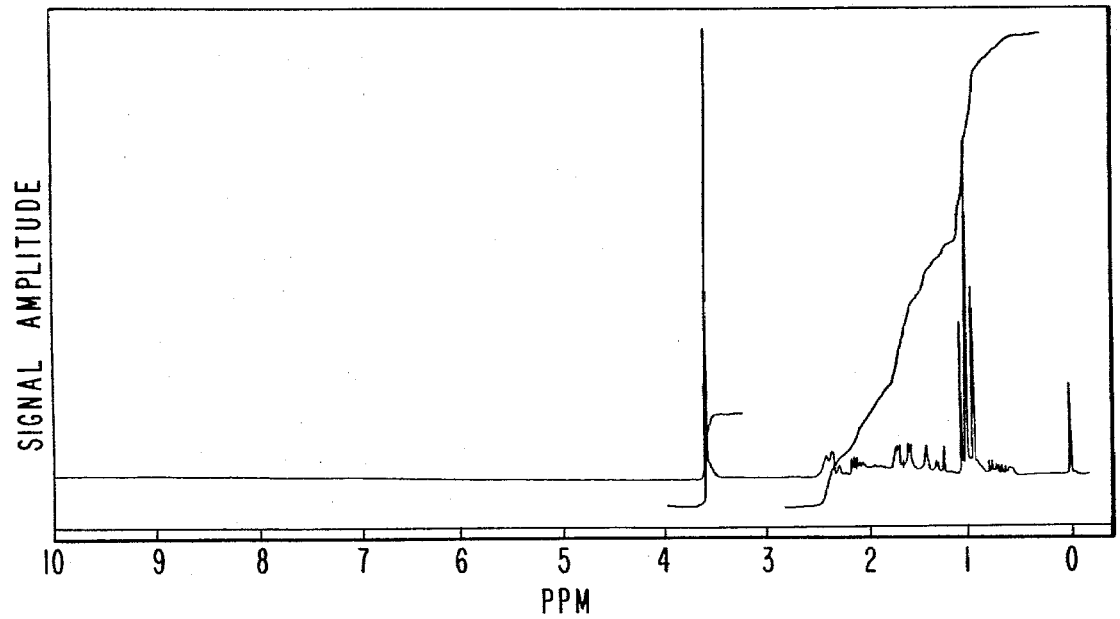

FIG. 6B represents the NMR spectrum for fraction 6 of the distillation product of the reaction product of Example II consisting essentially of the compound having the structure:

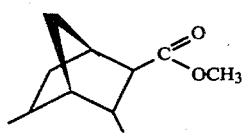

FIG. 7A represents the infrared spectrum for peak 1 of the GLC profile of FIG. 5 of the reaction product of Example II consisting essentially of the compound having the structure:

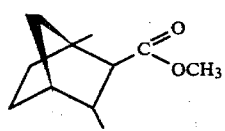

FIG. 7B represents the infrared spectrum for fraction 6 of the distillation product of the reaction product of Example II having the structure:

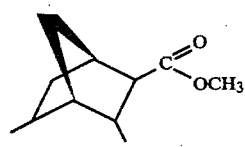

Figure 8:
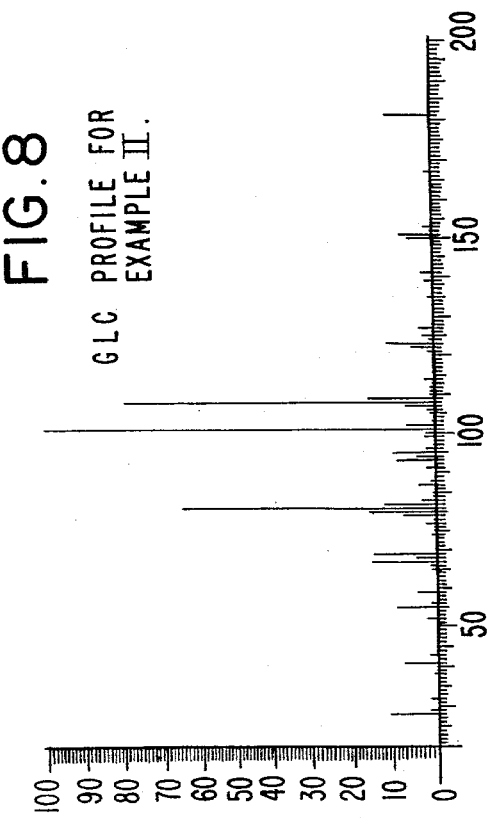

FIG. 8 represents the mass spectrum of the reaction product of Example II containing compounds having the structures:

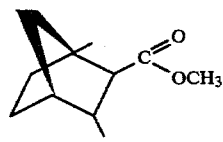

and

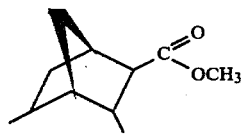

Figure 9:
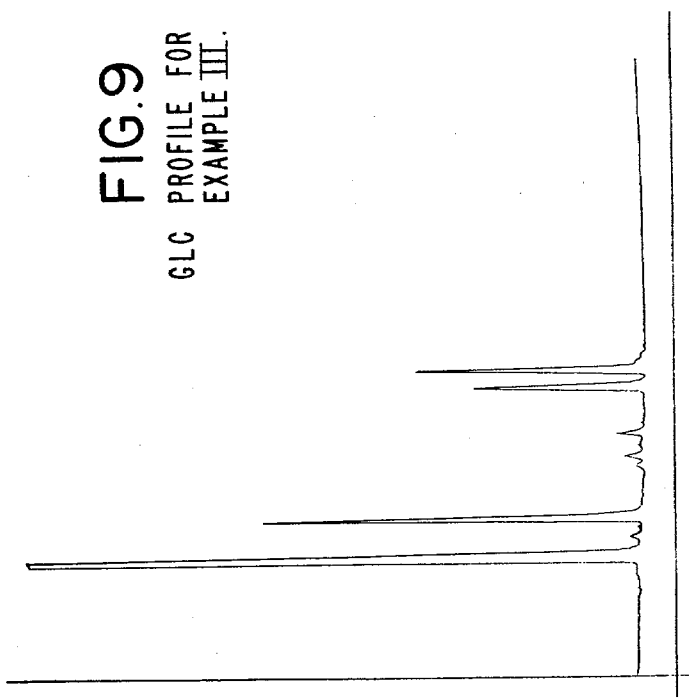

FIG. 9 represents the GLC profile of the reaction product of Example III containing compounds having the structures:

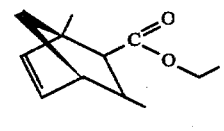

and

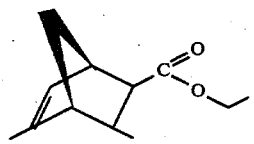

Figure 10:
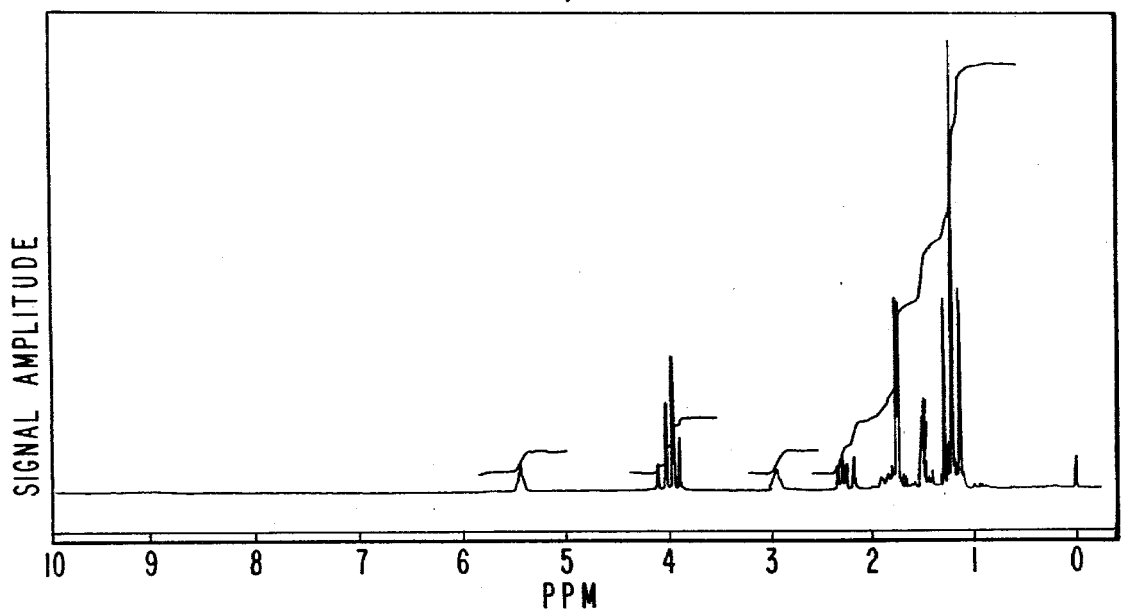

FIG. 10A represents the NMR spectrum for fraction 10 of the distillation product of the reaction product of Example III containing the compound having the structure:

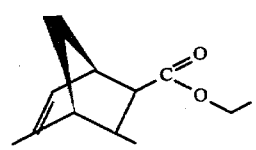

FIG. 10B represents the NMR spectrum for fraction 6 of the distillation product of the reaction product of Example III containing the compound having the structure:

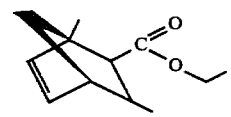

Figure 11:
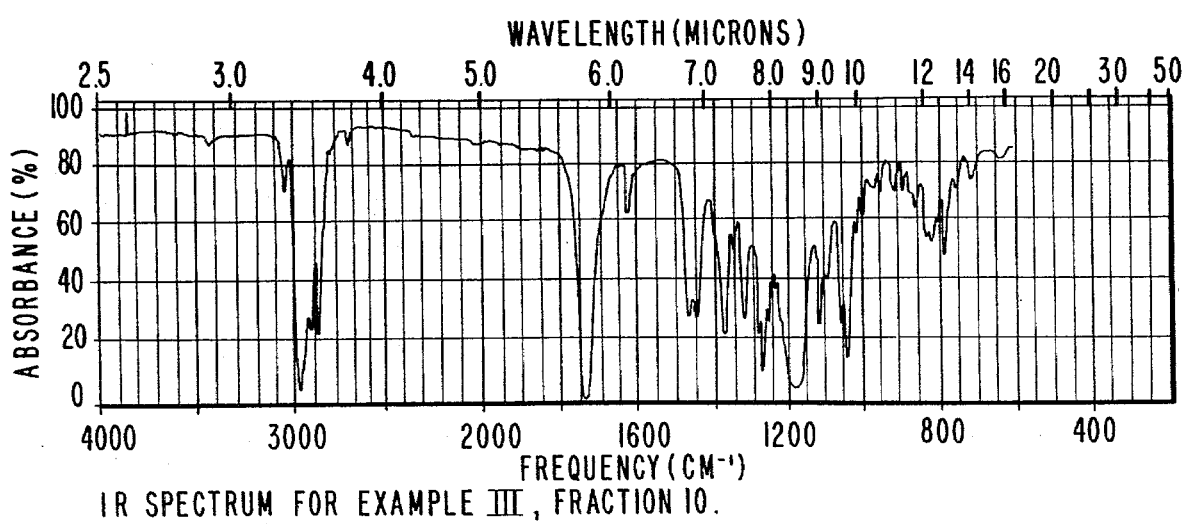
Figure 11:
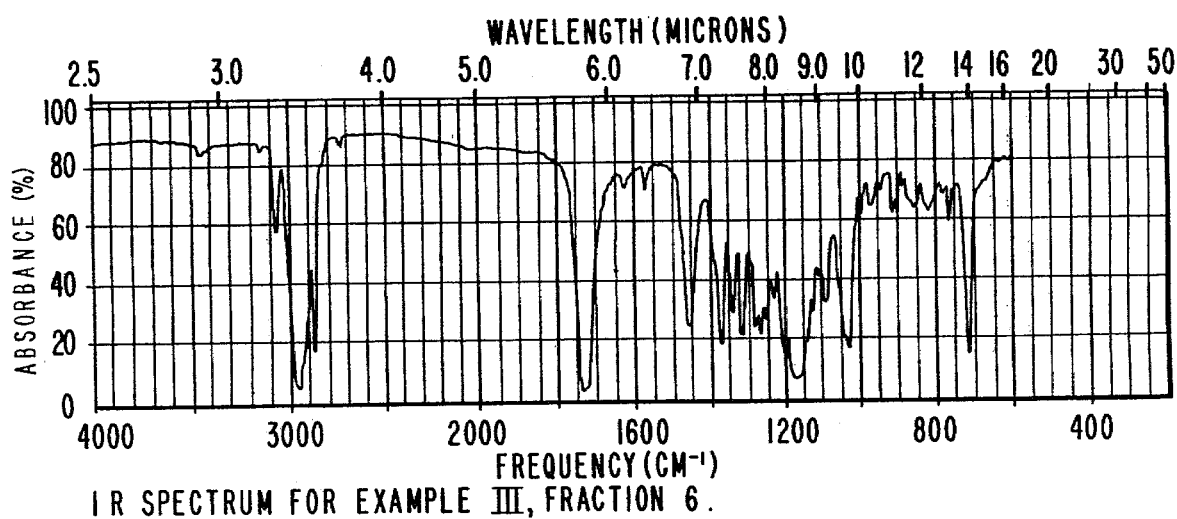

FIG. 11A represents the infrared spectrum for fraction 10 of the distillation product of the reaction product of Example III containing the compound having the structure:

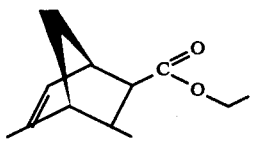

FIG. 11B represents the infrared spectrum for fraction 6 of the distillation product of the reaction product of Example III containing the compound having the structure:

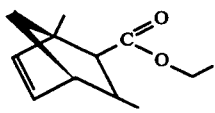

Figure 12:
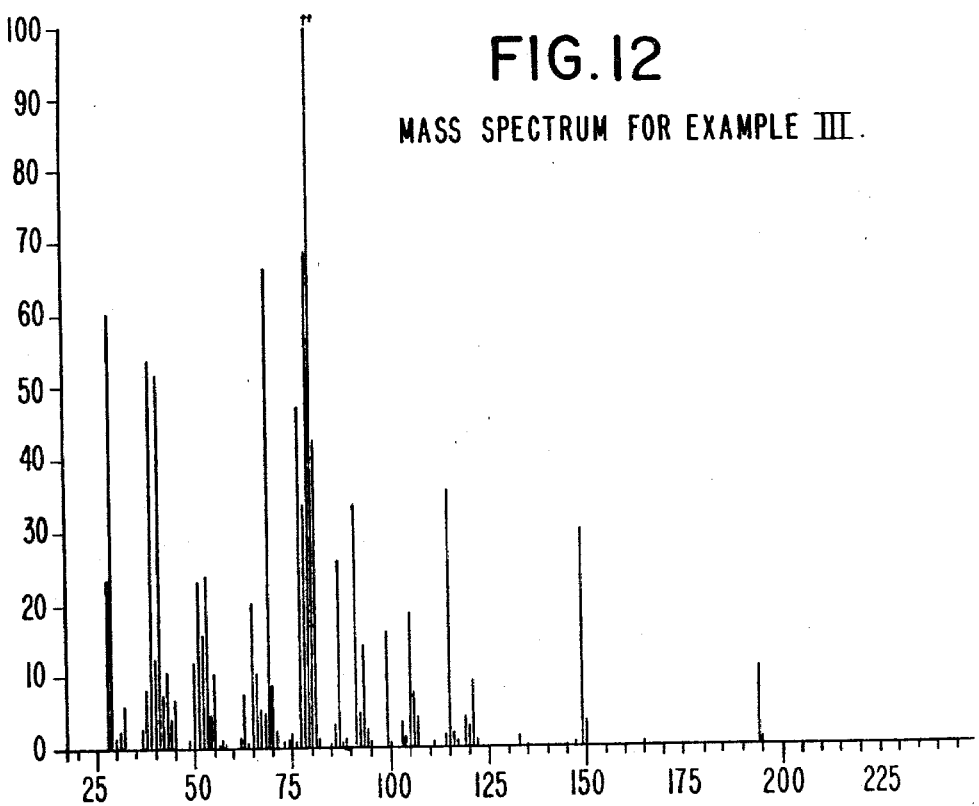

FIG. 12 represents the mass spectrum for the reaction product of Example III containing compounds having the structures:

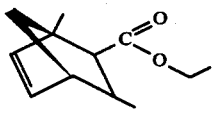

and

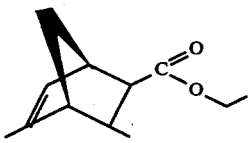

FIG. 13 represents the GLC profile of the crude reaction product (washed before distilling) of Example IV containing the compounds having the structures:

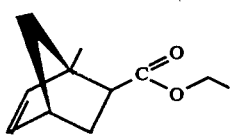

and

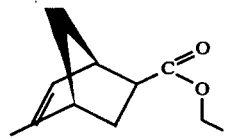

FIG. 14 represents the GLC profile for bulked fractions 7-12 inclusive of the distillation product of the reaction product of Example IV (conditions: Carbowax column programmed at 80°-122° C. at 8° C. per minute).

FIG. 15A represents the NMR spectrum for the reaction product of Example IV containing the compound having the structure:

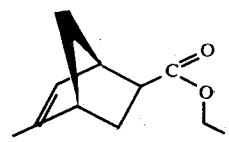

Figure 15B:
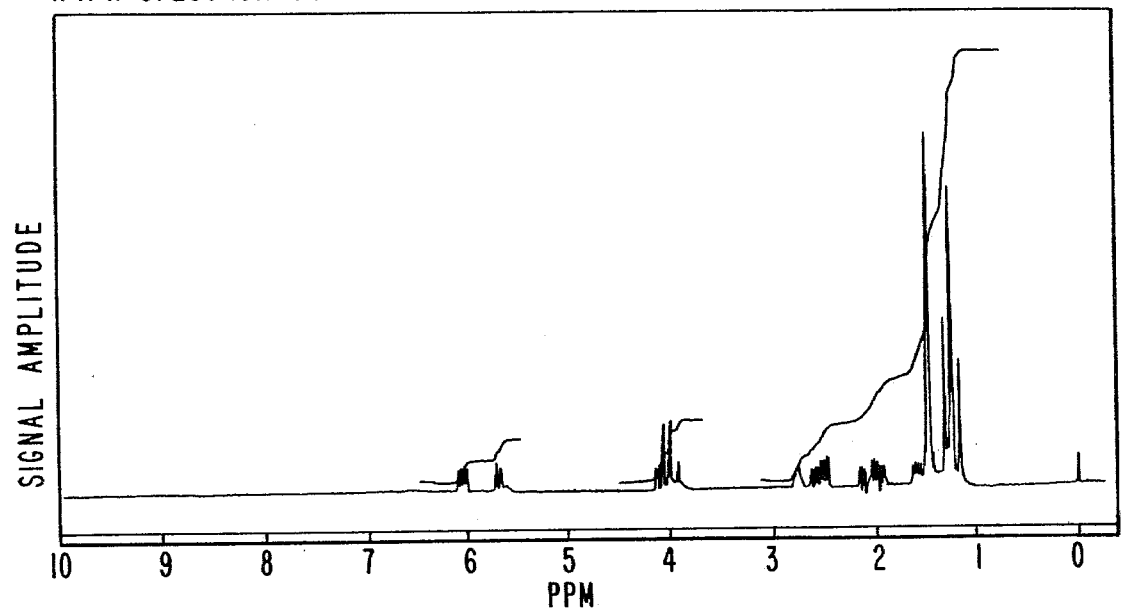

FIG. 15B represents the NMR spectrum for the reaction product of Example IV containing the compound having the structure:

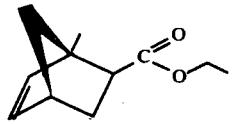

Figure 16A:
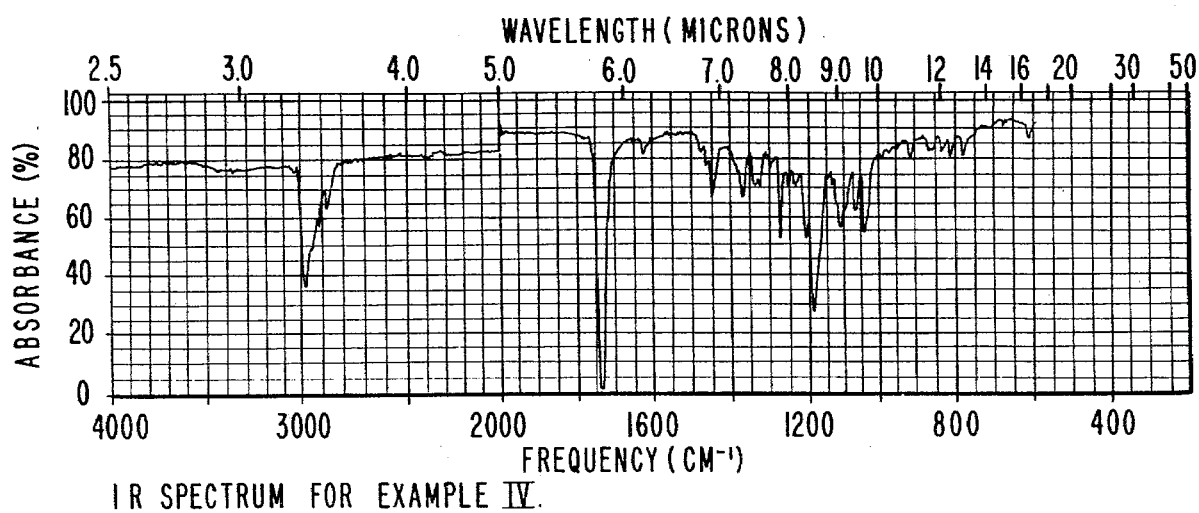
Figure 16:
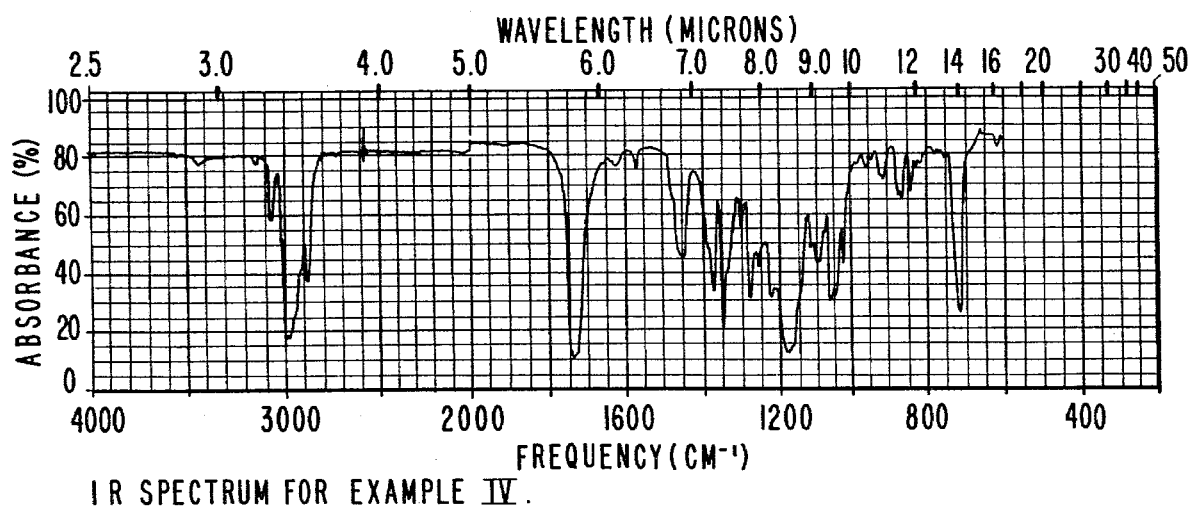

FIG. 16A represents the infrared spectrum for the reaction product of Example IV containing the compound having the structure:

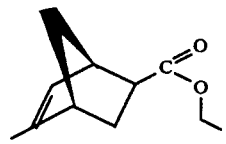

FIG. 16B represents the infrared spectrum for the reaction product of Example IV containing the compound having the structure:

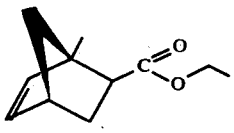

Figure 17:
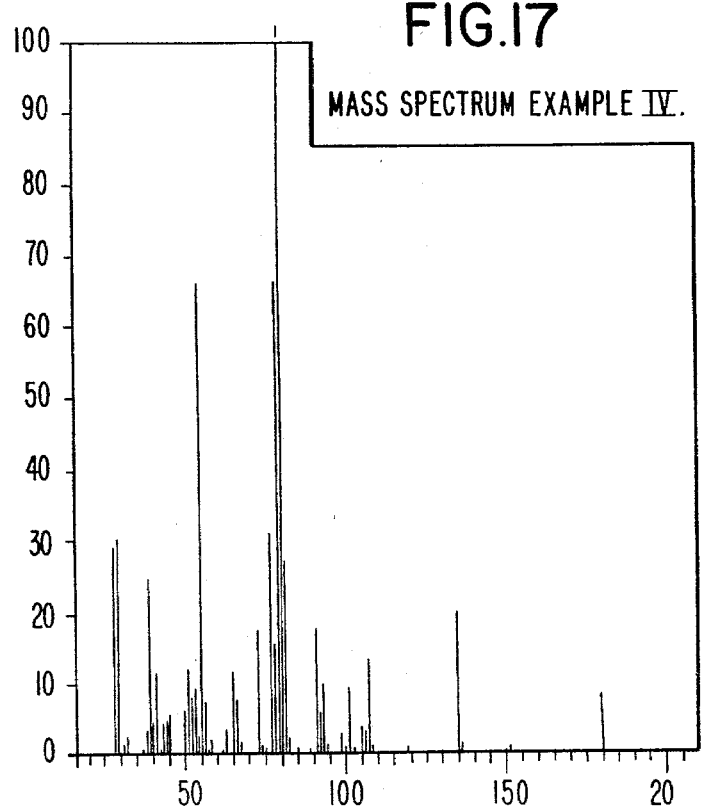

FIG. 17 represents the mass spectrum for the reaction product of Example IV containing the compounds having the structures:

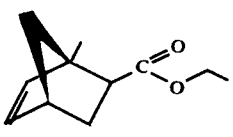

and

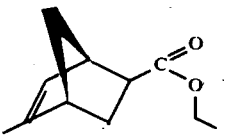

Figure 18:
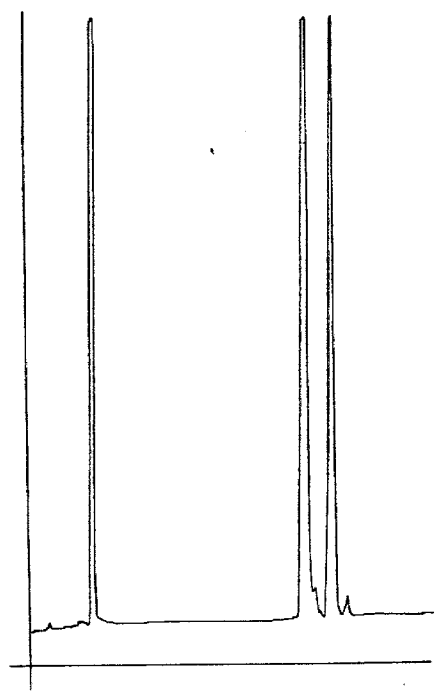

FIG. 18 represents the GLC profile for the reaction product of Example V containing the compounds having the structures:

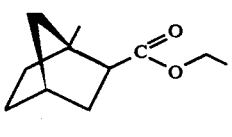

and

-continued

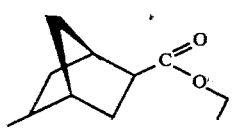

Figure 19:
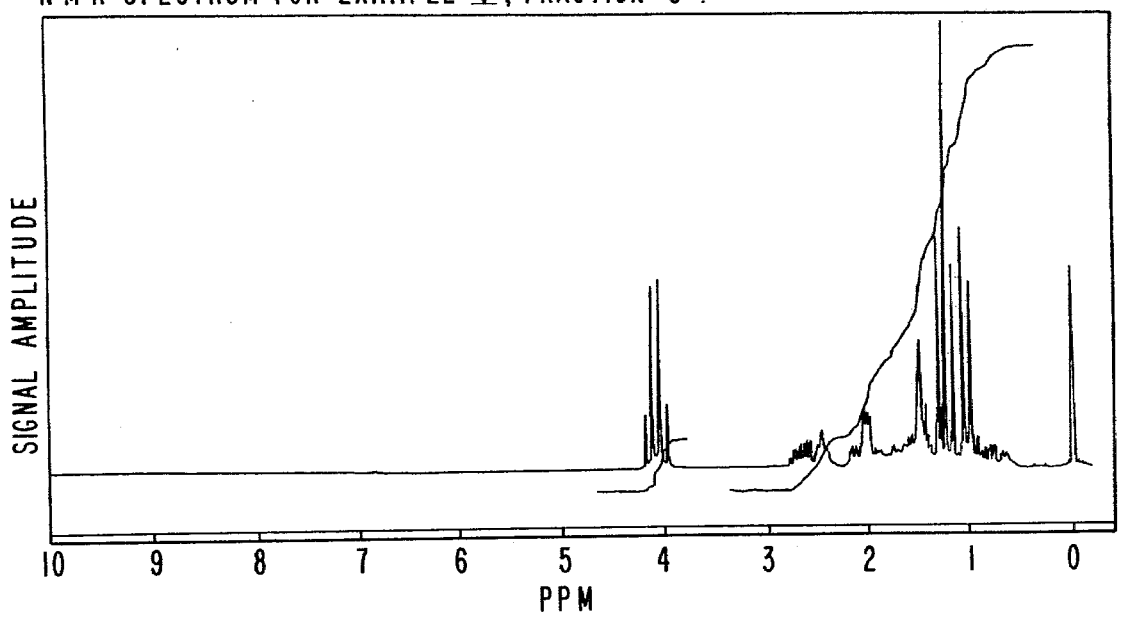
Figure 19:
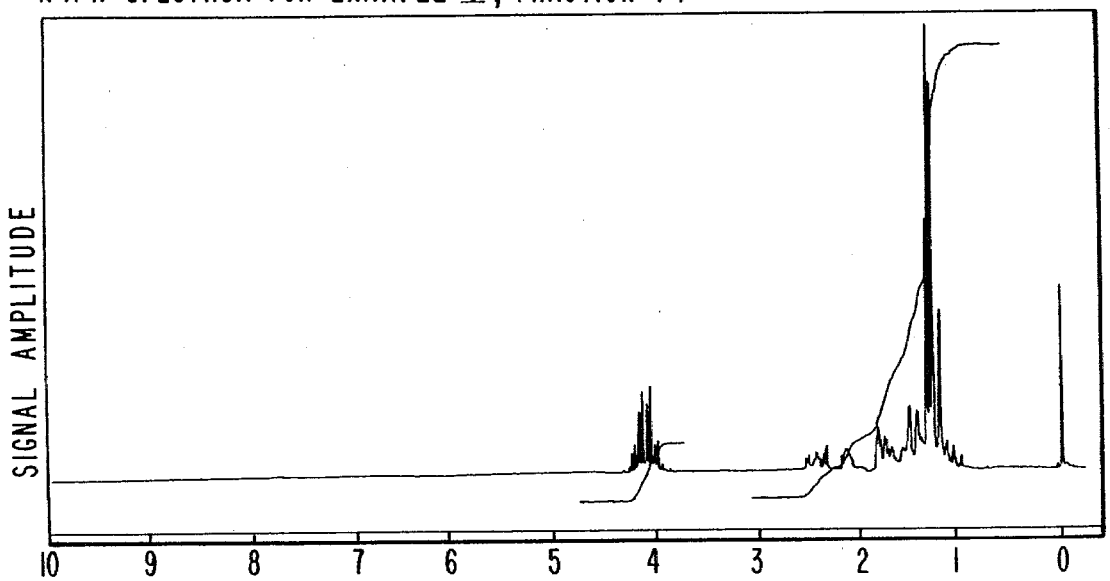

FIG. 19A represents the NMR spectrum for fraction 9 of the distillation product of the reaction product of Example V containing the compound having the structure:

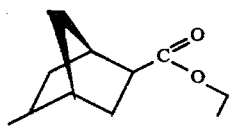

FIG. 19B represents the NMR spectrum for fraction 1 of the distillation product of the reaction product of Example V containing the compound having the structure:

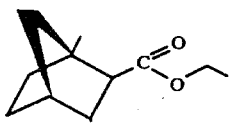

Figure 20A:
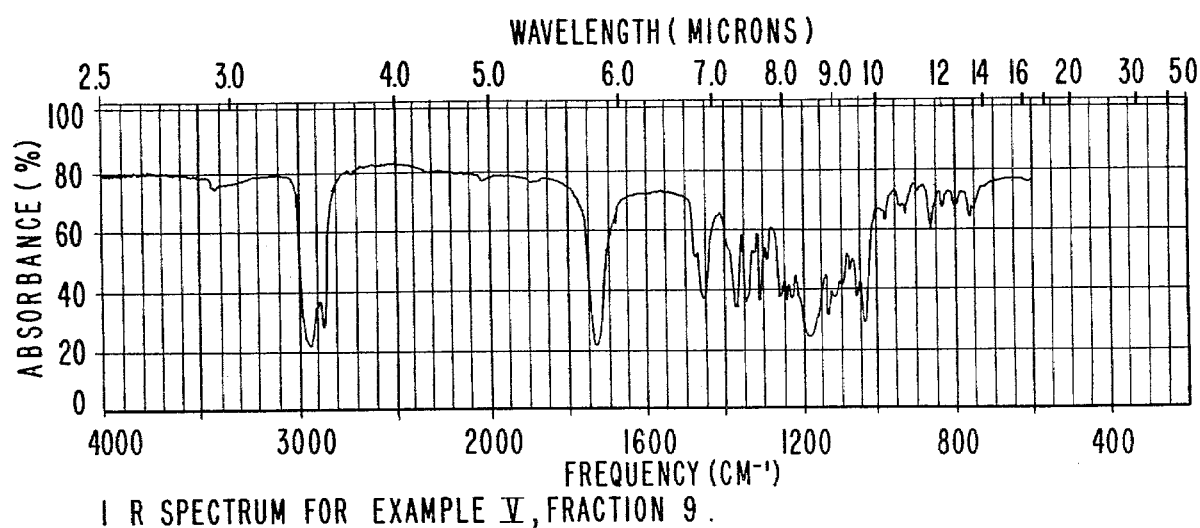

FIG. 20A represents the infrared spectrum for fraction 9 of the distillation product of the reaction product of Example V containing the compounds having the structure:

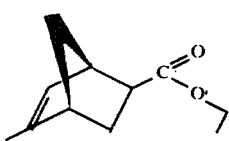

Figure 20B:
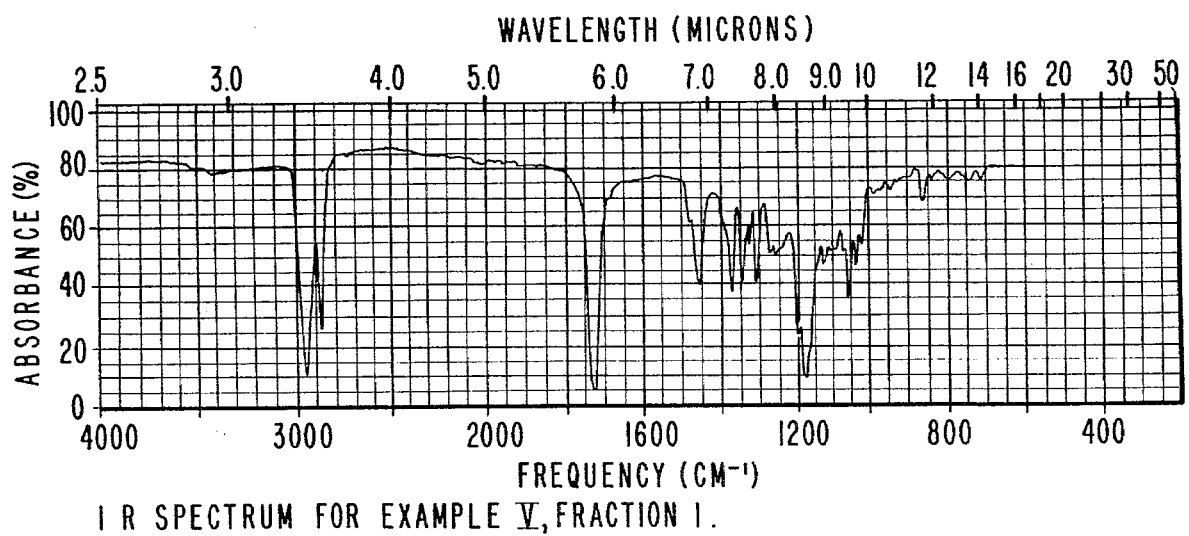

FIG. 20B represents the infrared spectrum for fraction 1 of the distillation product of the reaction product of Example V containing the compound having the structure:

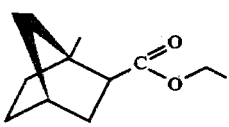

Figure 21:
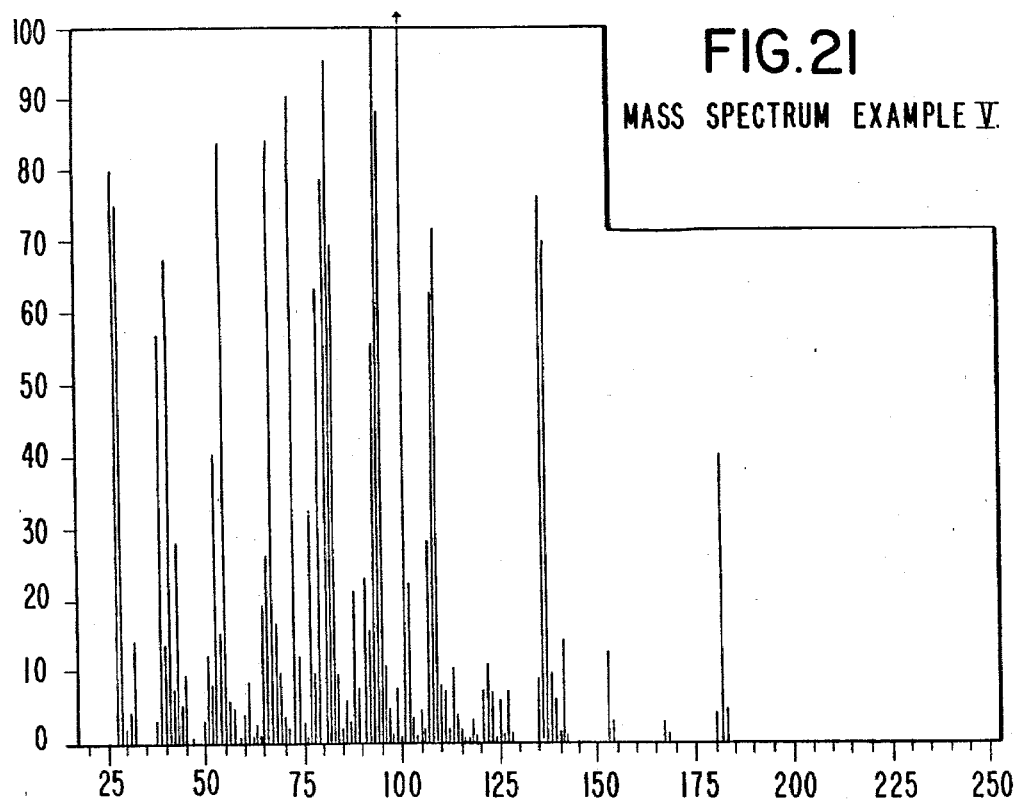
Figure 10:
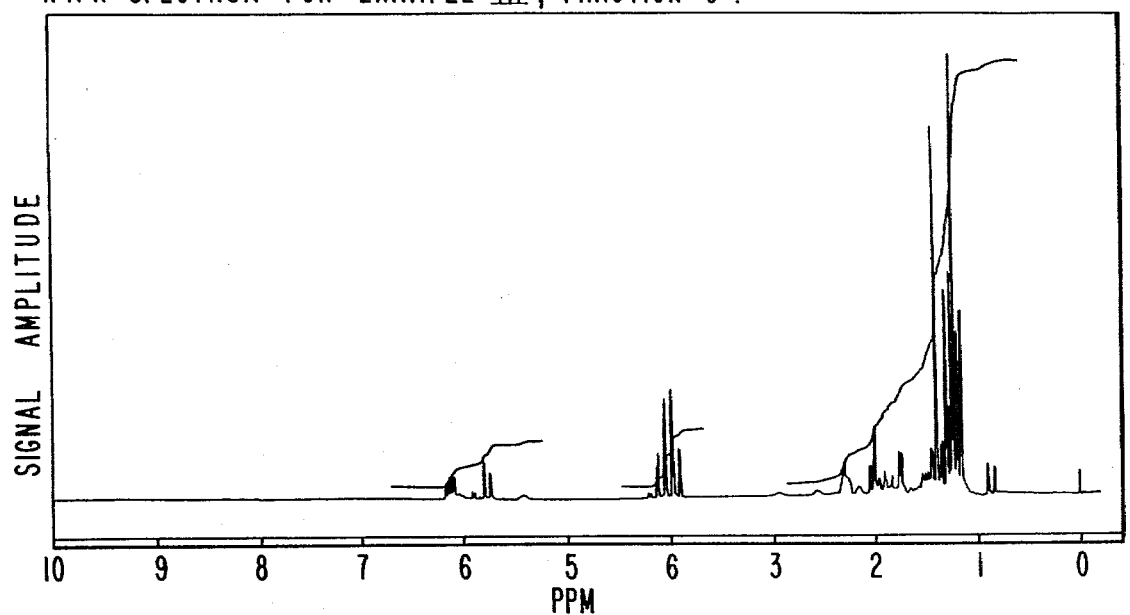

FIG. 21 represents the mass spectrum for the reaction product of Example V containing the compounds having the structures:

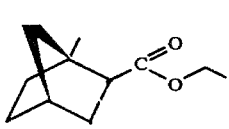

and

-continued

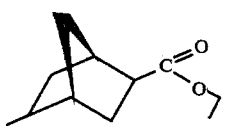

Figure 22:
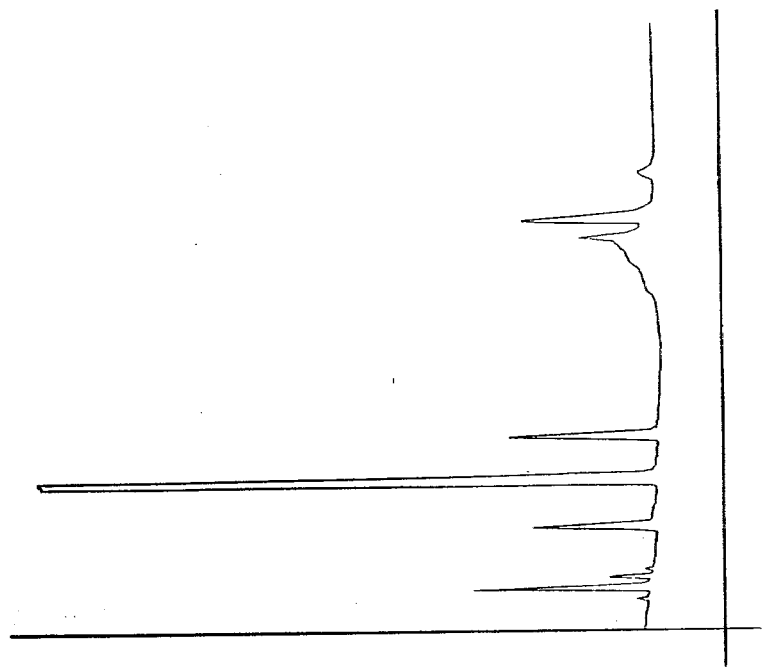

FIG. 22 represents the GLC profile for the reaction product of Example VI containing the compounds having the structures:

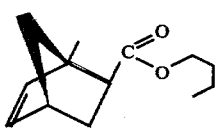

and

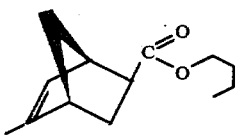

Figure 23:
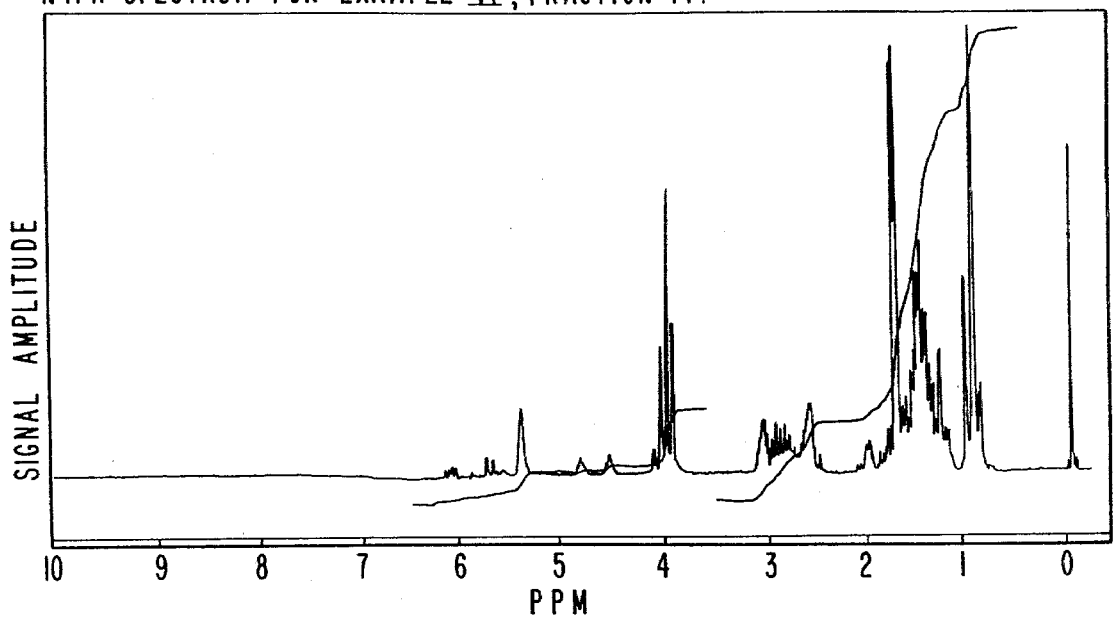
Figure 23:
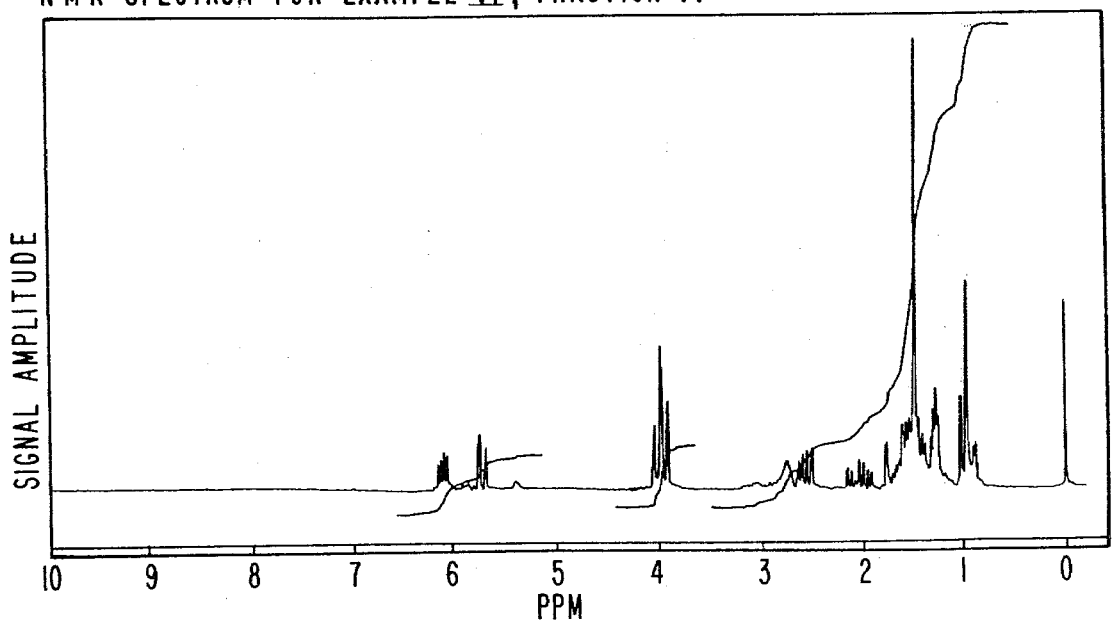

FIG. 23A represents the NMR spectrum for fraction 14 of the distillation product of the reaction product of Example VI containing the compound having the structure:

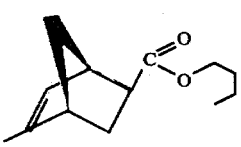

FIG. 23B represents the NMR spectrum for fraction 4 of the distillation product of the reaction product of Example VI containing the compound having the structure:

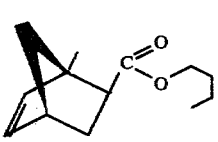

Figure 24A:
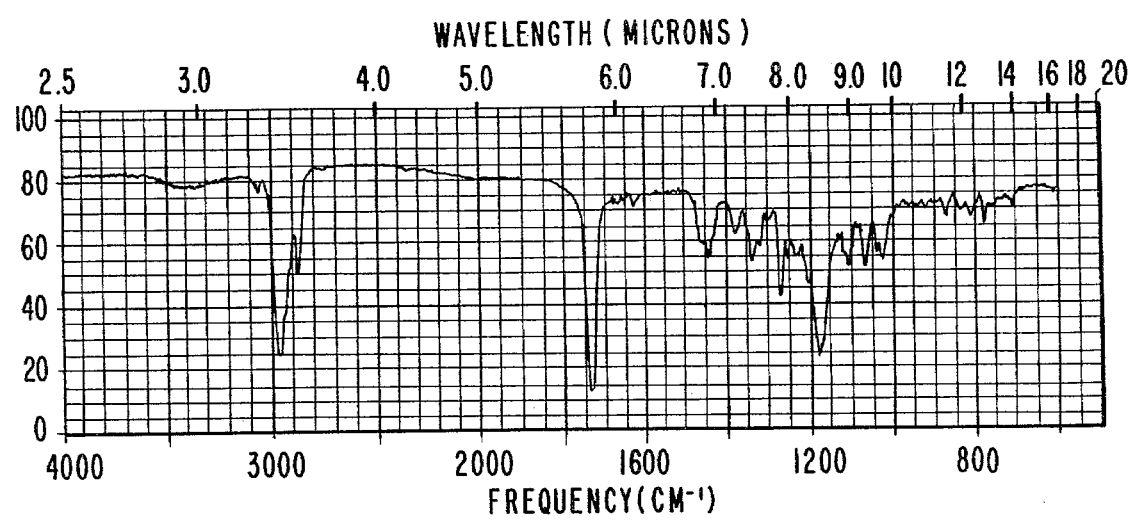

FIG. 24A reresents the infrared spectrum for fraction 14 of the distillation product of the reaction product of Example VI containing the compound having the structure:

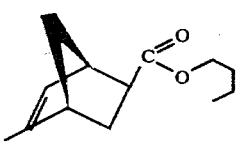

Figure 24B:
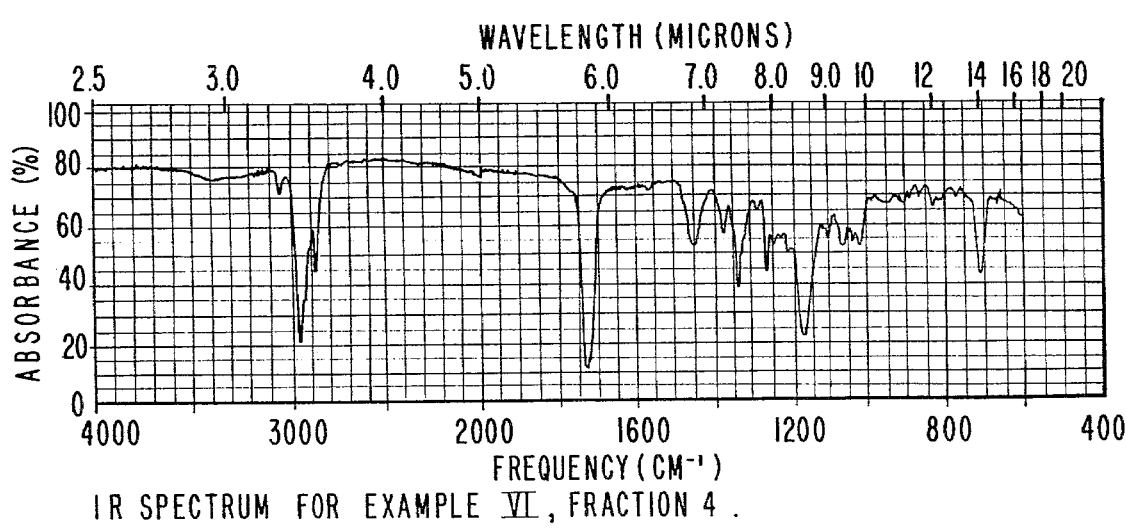

FIG. 24B represents the infrared spectrum for fraction 4 of the distillation product of the reaction product of Example VI containing the compound having the structure:

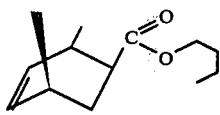

Figure 25:
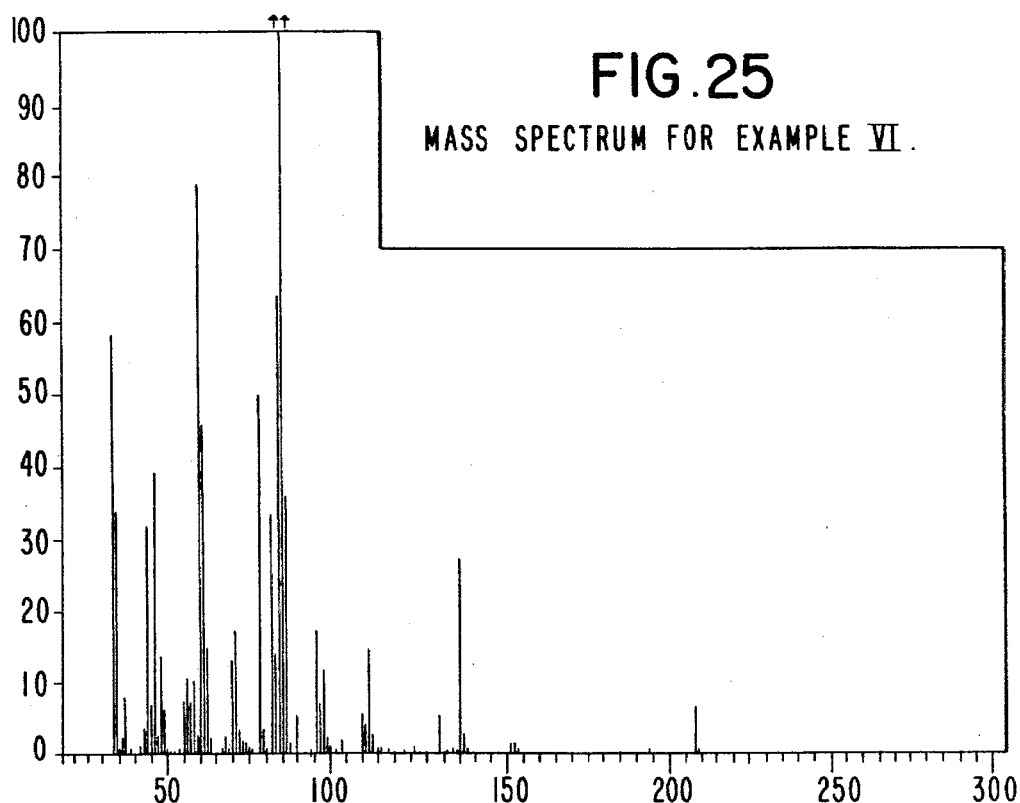

FIG. 25 represents the mass spectrum for the reaction product of Example VI containing the compounds having the structures:

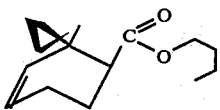

and

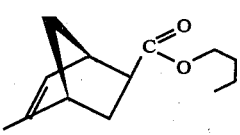

Figure 26:
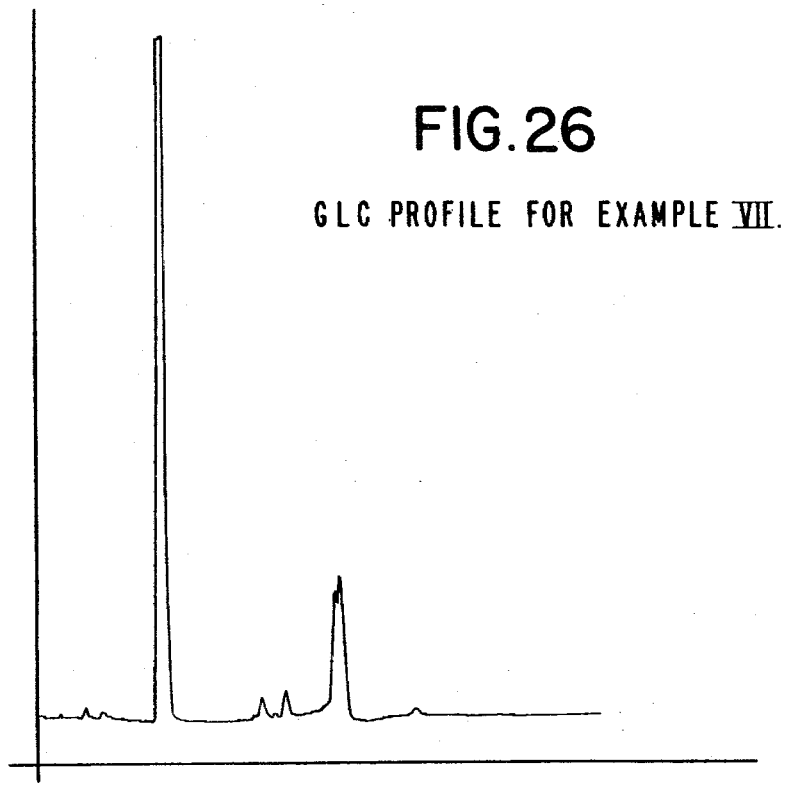

FIG. 26 represents the GLC profile for the reaction product of Example VII containing the compounds having the structures:

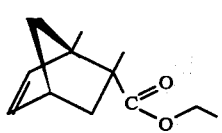

and

Figure 27:
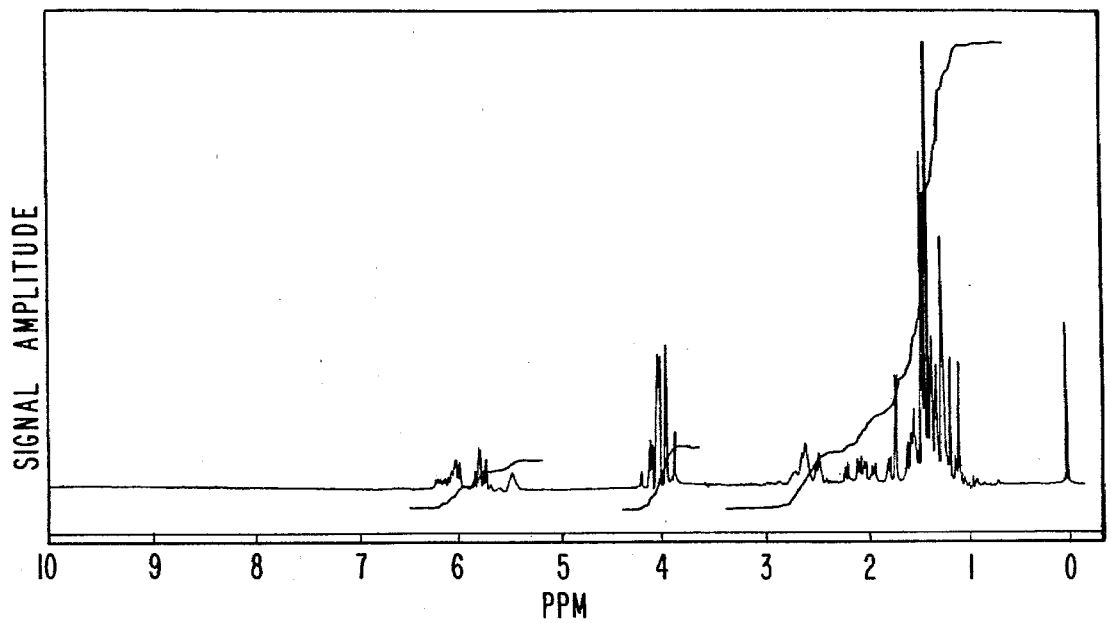

FIG. 27 represents the NMR spectrum for the reaction product of Example VII containing a mixture of the compounds having the structures:

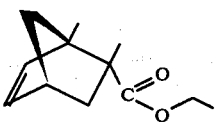

and

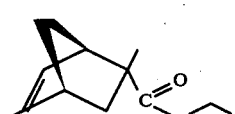

Figure 28:
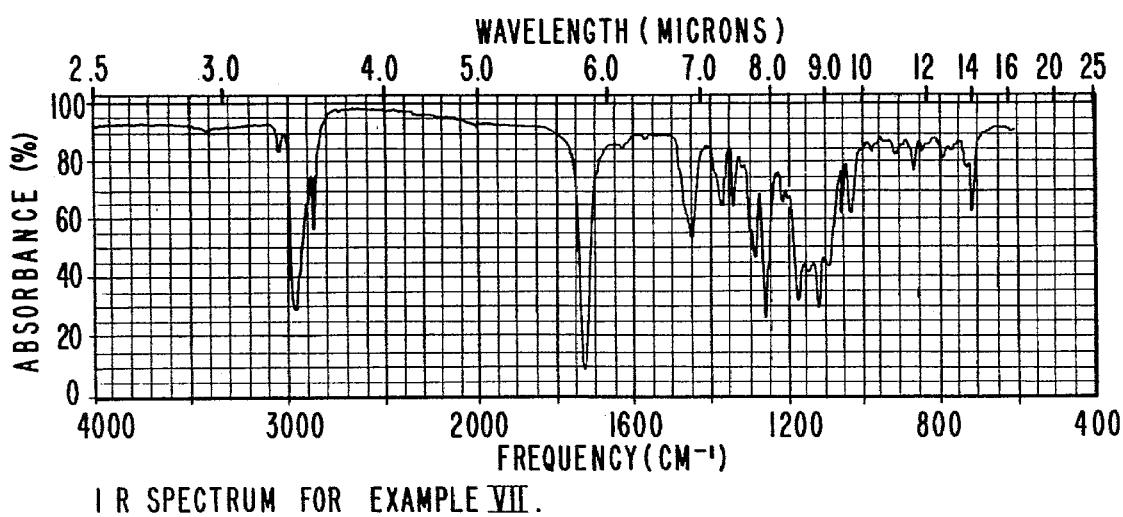

FIG. 28 represents the infrared spectrum for the reaction product of Example VII containing a mixture of the compounds having the structures:

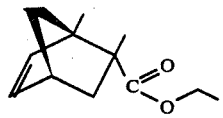

and

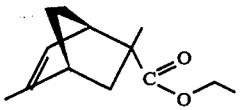

Figure 29:
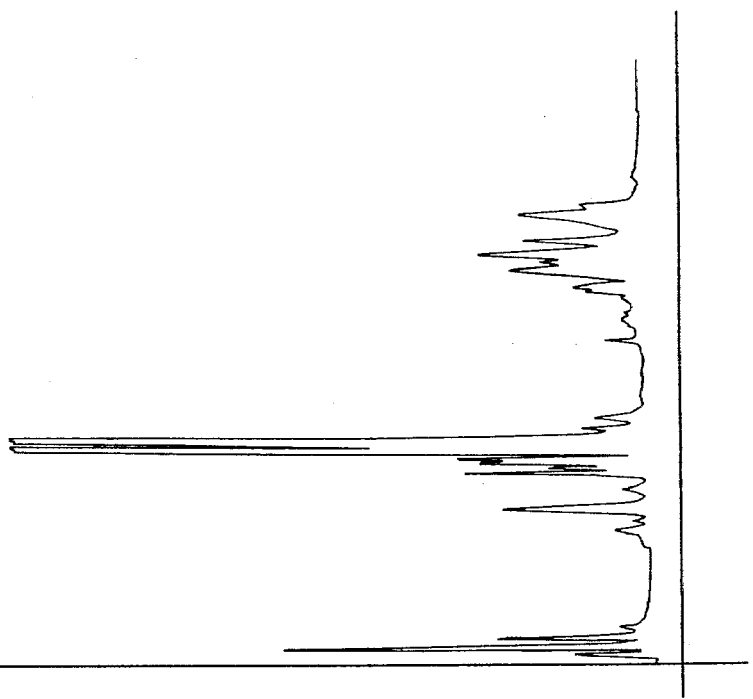

FIG. 29 represents the mass spectrum for the reaction product of Example VII containing a mixture of the compounds having the structures:

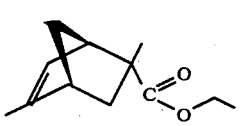

and

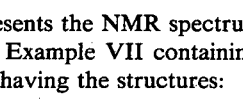

Figure 30:
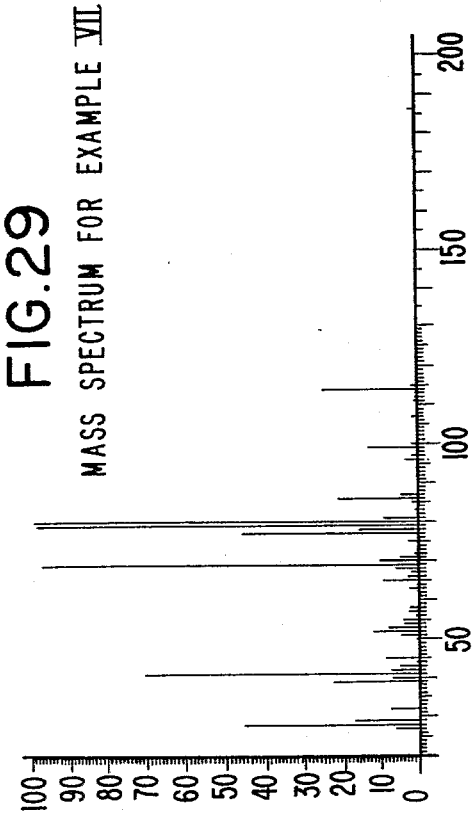

FIG. 30 sets forth the GLC profile for the reaction product of Example VII-A (bulked fractions 3–5 after distillation) consisting of the compounds having the structures:

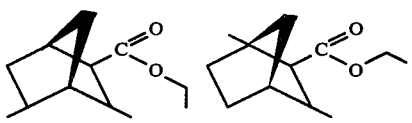

Figure 31:
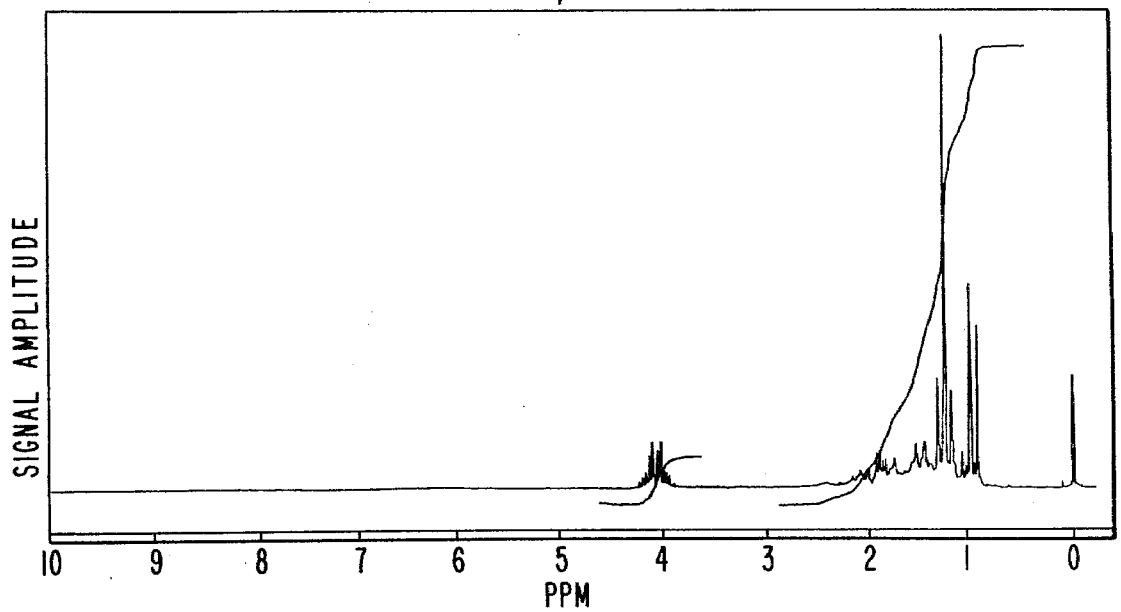

FIG. 31-A sets forth the NMR spectrum for fraction 1 of the distillation product of the reaction product of Example VII-A consisting of the compound having the structure:

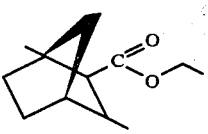

FIG. 31-A sets forth the the NMR spectrum for peak 2 of the GLC profile of the reaction product of Example VII-A consisting of the compound having the structure:

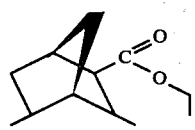

Figure 32:
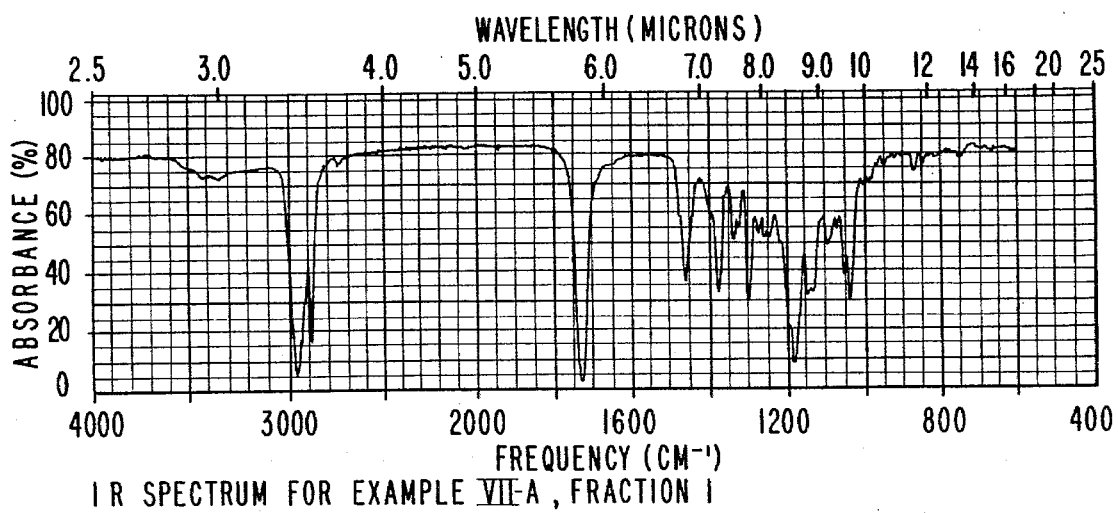
Figure 32:
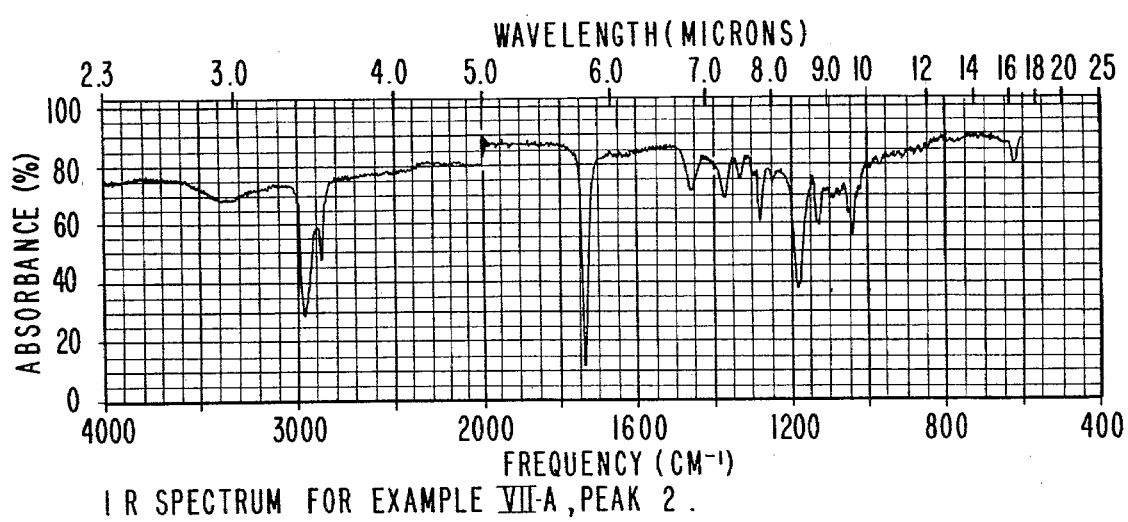
Figure 33:
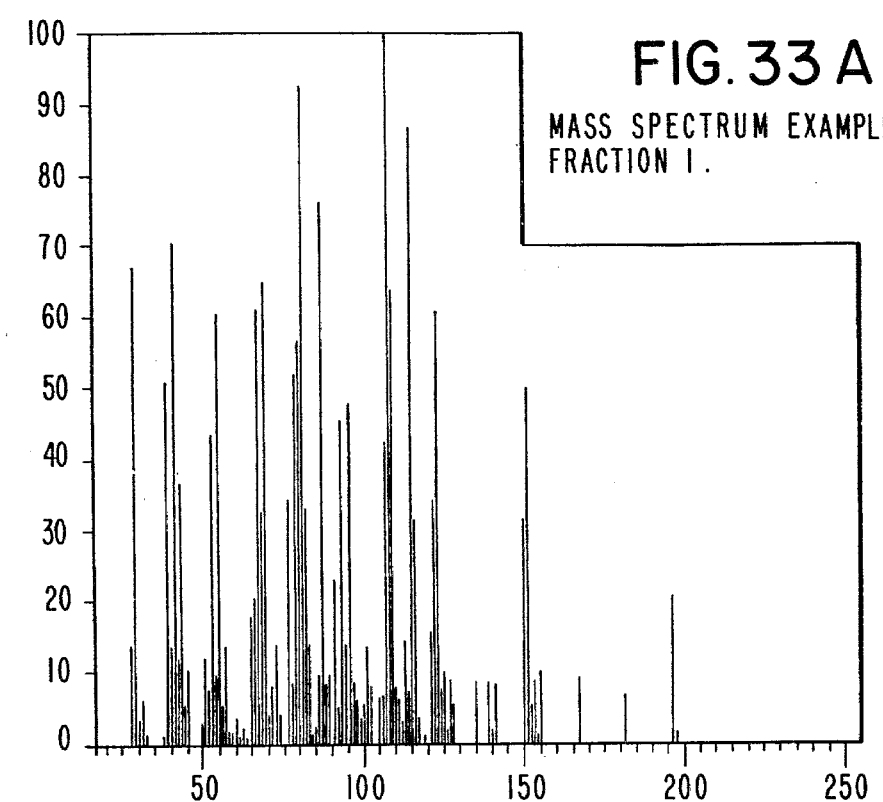

FIG. 32-A sets forth the infrared spectrum for fraction 1 of the distillation product of the reaction product of Example VII-A consisting of the compound having the structure:

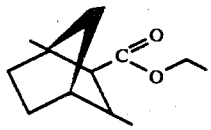

FIG. 32-B sets forth the infrared spectrum for peak 2 of the GLC profile of the reaction product of Example VII-A consisting of the compound having the structure:

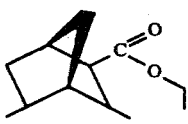

Figure 33:
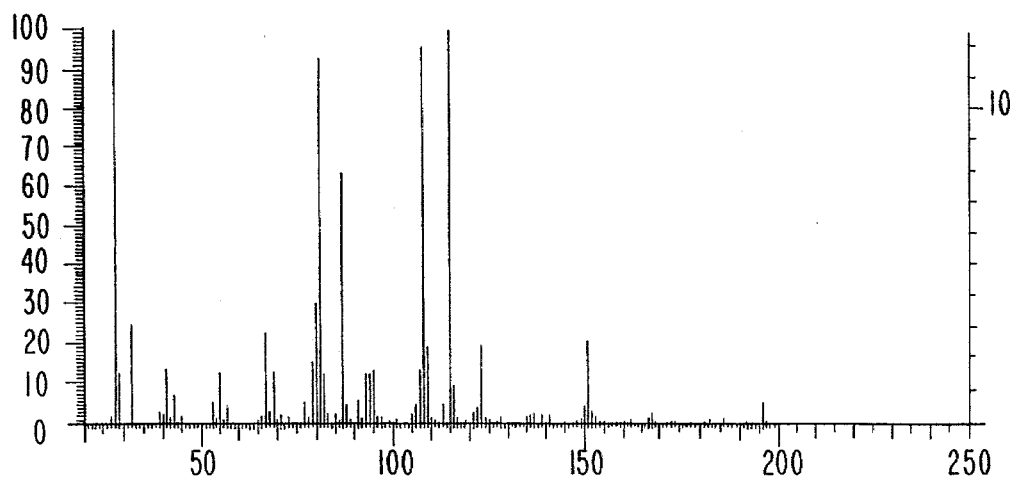
Figure 31:
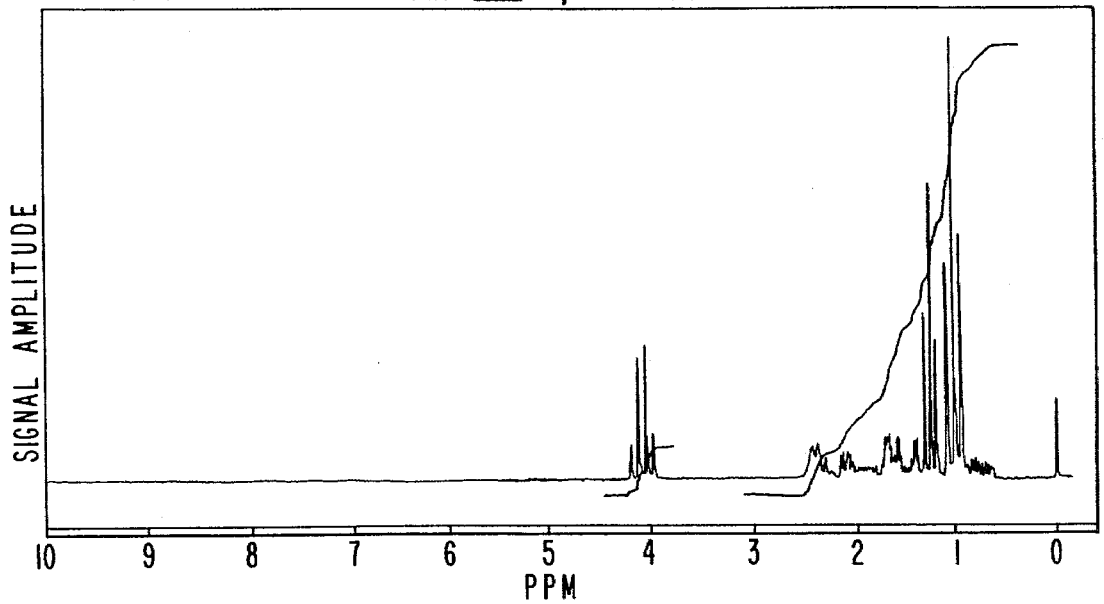

FIG. 33-A sets forth the mass spectrum for fraction 1 of the distillation product of the reaction product of Example VII-A consisting of the compound having the structure:

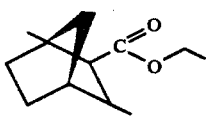

FIG. 33-B sets forth the mass spectrum for peak 2 of the GLC profile of the reaction product of Example VII-A consisting of the compound having the structure:

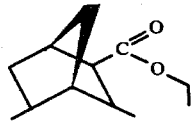

Figure 34:
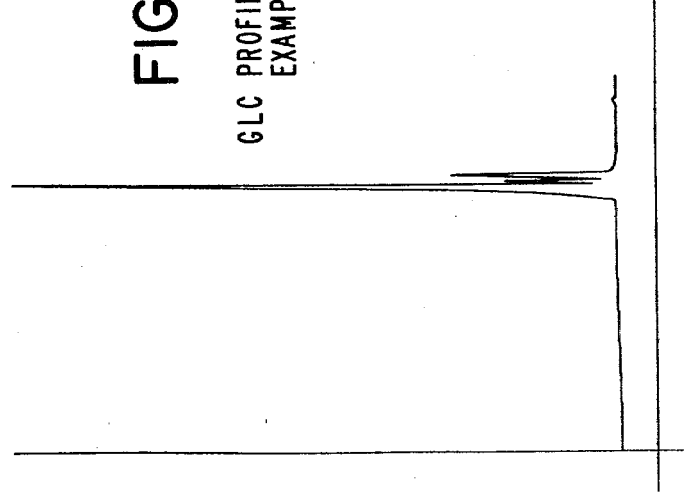

FIG. 34 is the GLC profile (conditions: carbowax programmed at 80°-220° C. at 8° C. per minute) of the reaction product of Example XXXII containing the compounds having the structures:

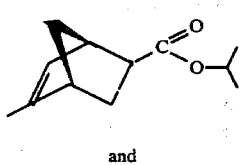

and

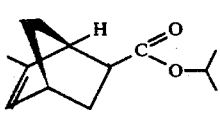

Figure 35A:
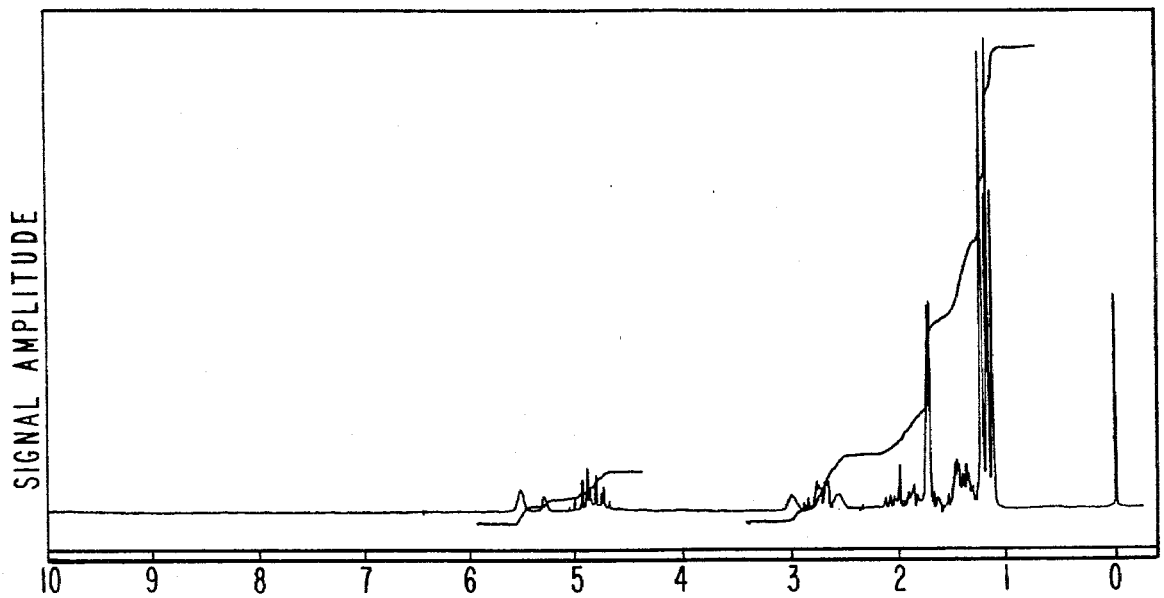
Figure 35B:
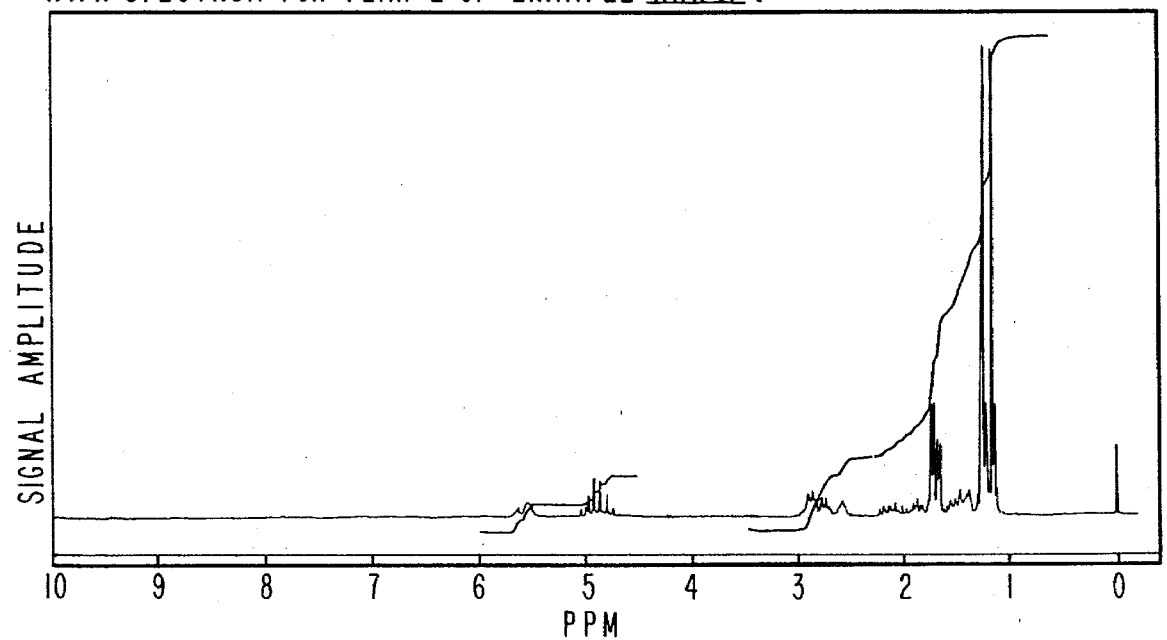

FIG. 35-A is the NMR spectrum for Peak 1 of the GLC profile of FIG. 34 containing the compound having the structure:

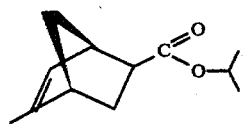

FIG. 35-B is the NMR spectrum for Peak 2 of the GLC profile of FIG. 34 containing the compound having the structure:

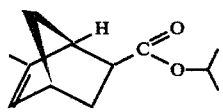

Figure 36A:
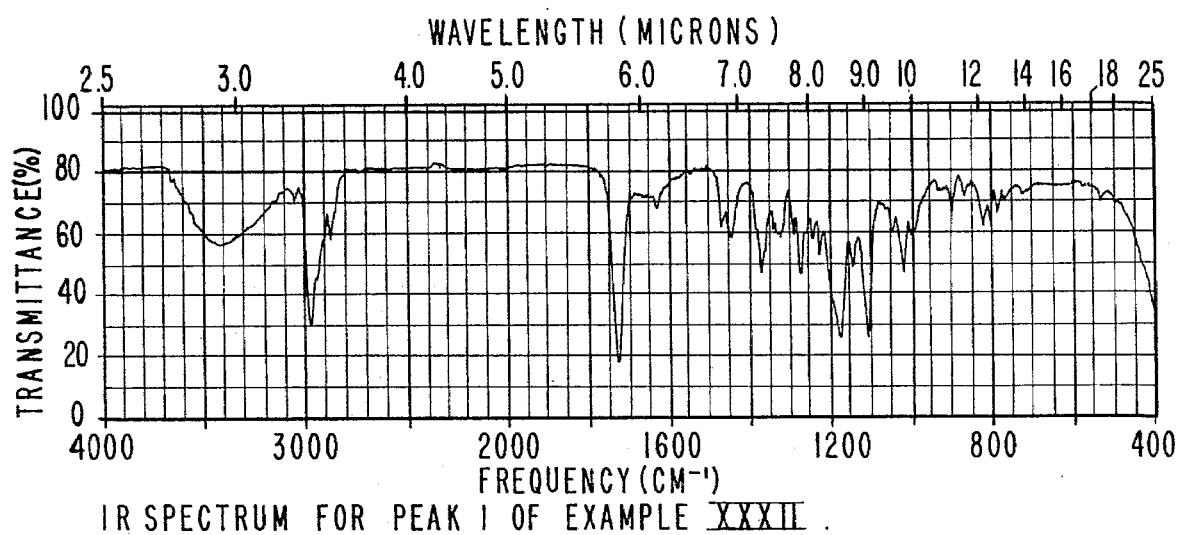
Figure 36B:
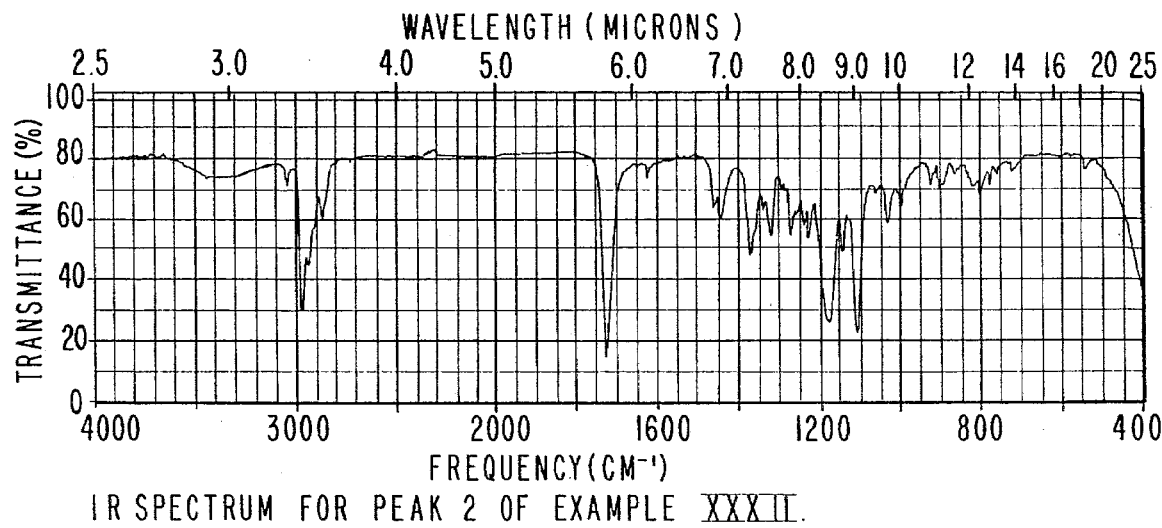

FIG. 36-A is the infra-red spectrum for Peak 1 of the GLC profile of FIG. 34 containing the compound having the structure:

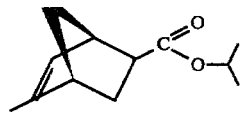

FIG. 36-B is the infra-red spectrum for Peak 2 of the GLC profile of FIG. 34 containing the compound having the structure:

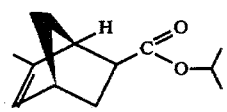

Figure 37:
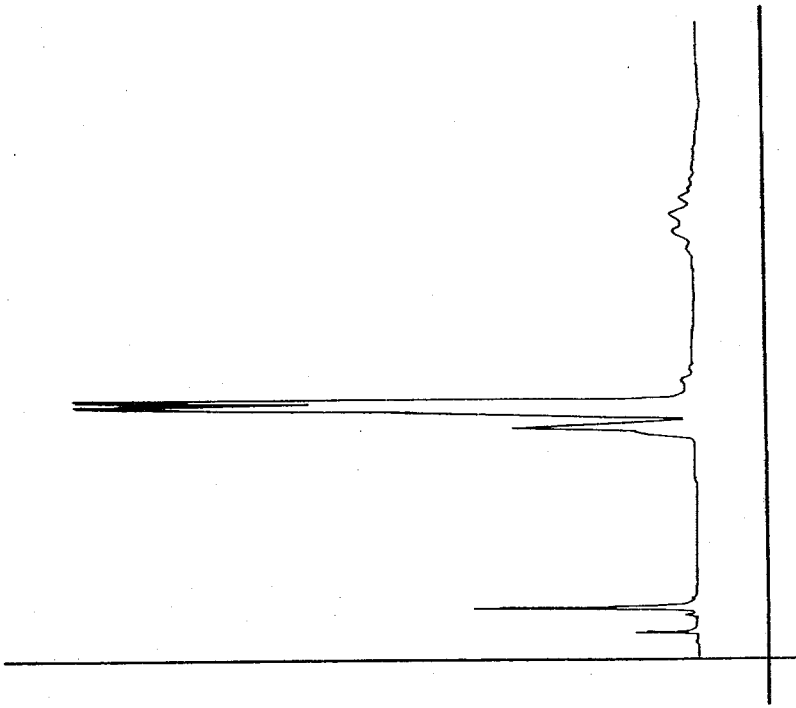
Figure 41A:
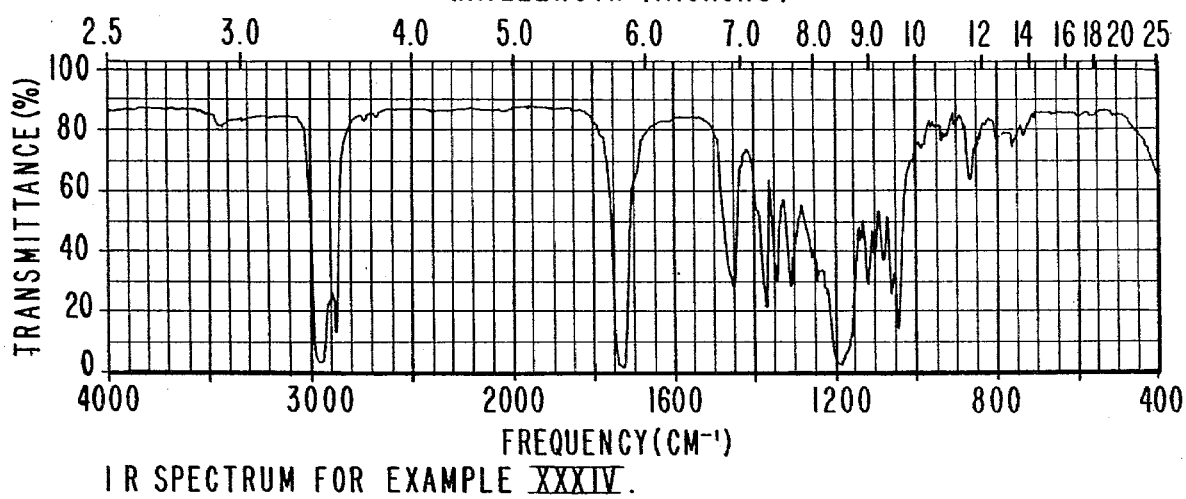

FIG. 37 is the GLC profile for the reaction product of Example XXXIII (conditions: SE-30 column programmed at 80°-220° C. at 8° C. per minute) containing the compounds having the structures:

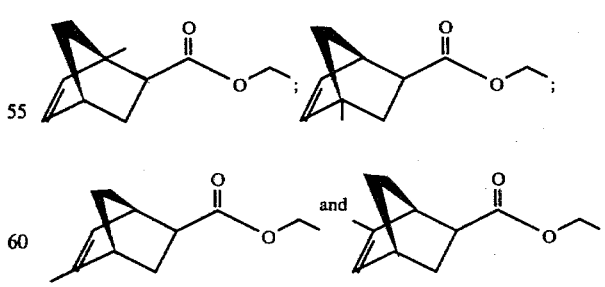

(reaction product before distillation).

Figure 38A:
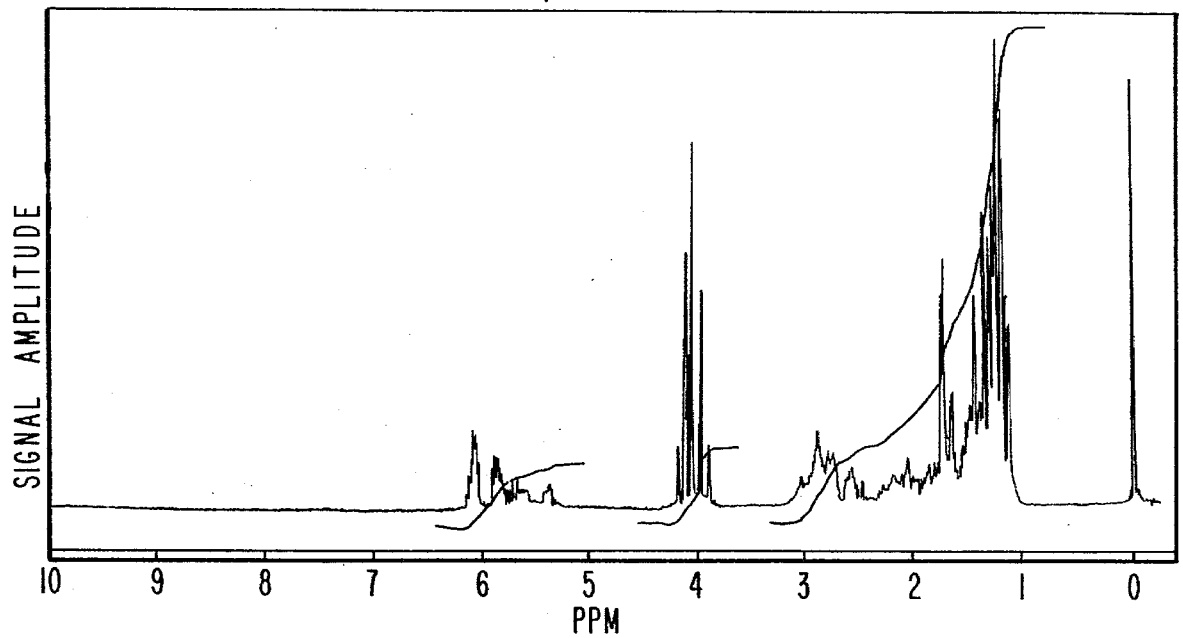
Figure 38:
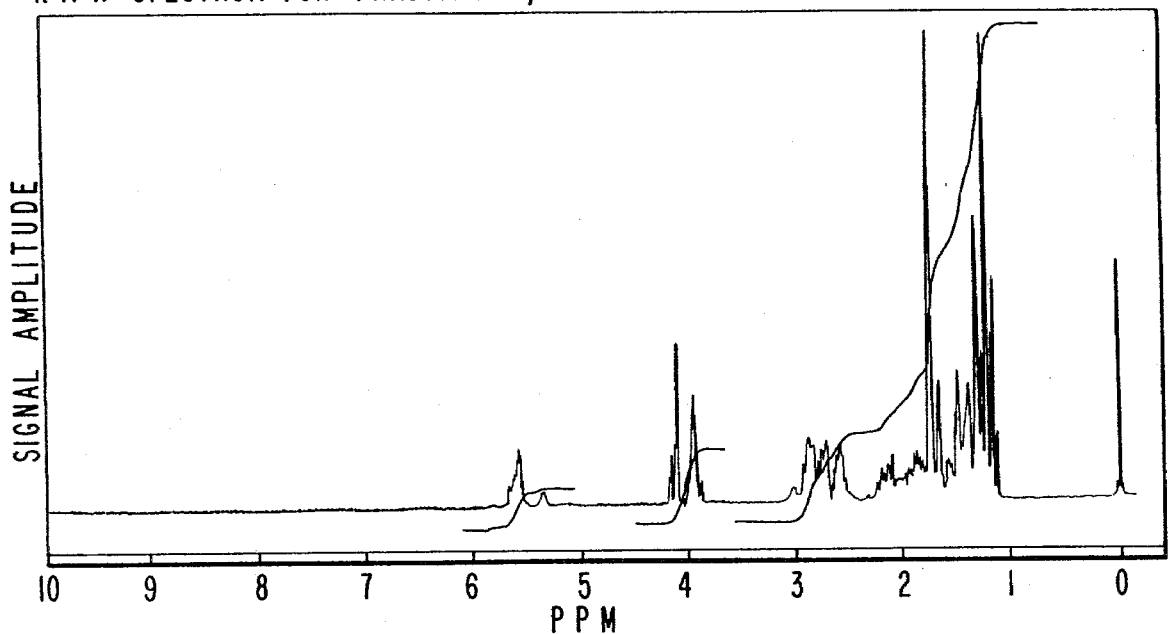

FIG. 38-A is the NMR spectrum for Fraction 1, Peak 1 of the distillation product of the reaction product of Example XXXIII containing the compounds having the structures:

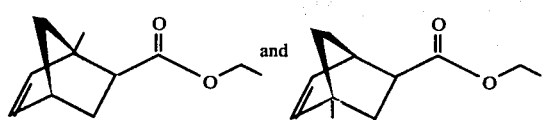

FIG. 38-B is the NMR spectrum for Fraction 8, Peak 2 of the distillation product of the reaction product of Example XXXIII containing the compounds having the structures:

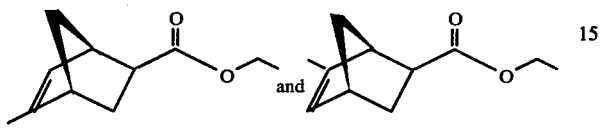

Figure 39:
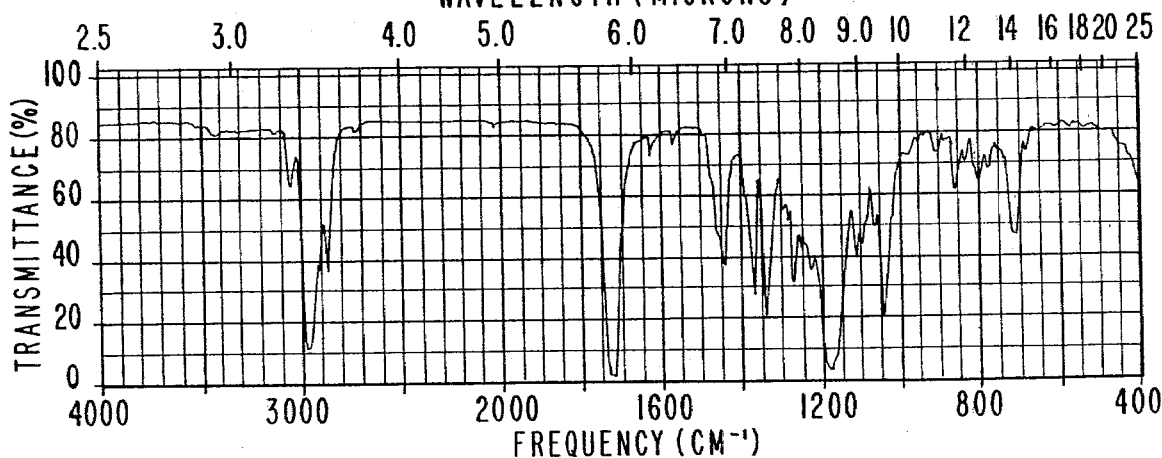
Figure 39B:
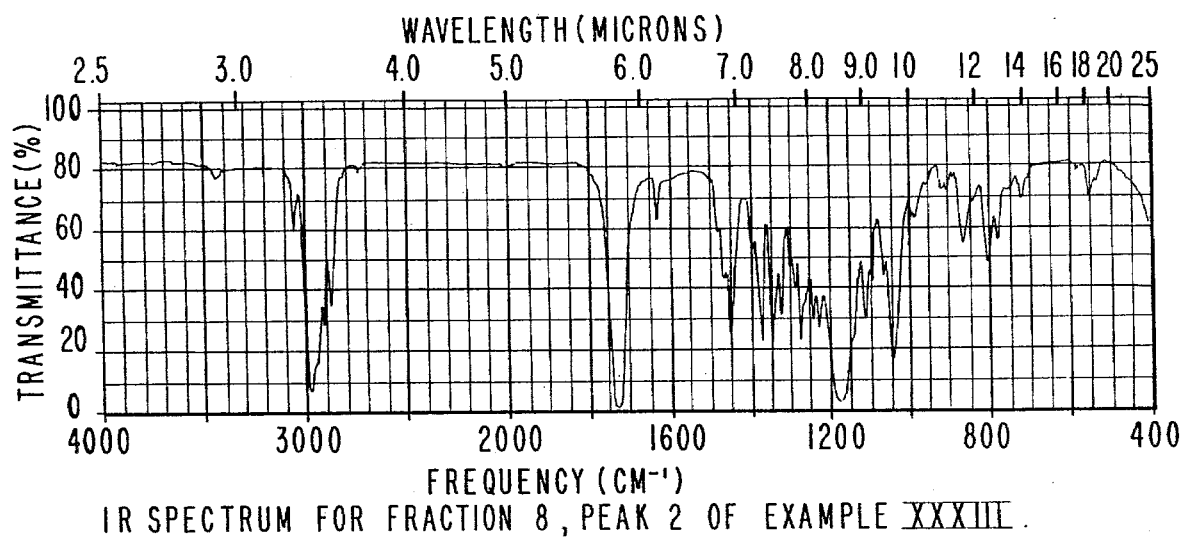

FIG. 39-A is the infra-red spectrum for Fraction 1, Peak 1 of the distillation product of the reaction product of Example XXXIII containing the compounds having the structures:

FIG. 39-B is the infra-red spectrum for Fraction 8, Peak 2 of the distillation product of the reaction product of Example XXXIII containing the compounds having the structures:

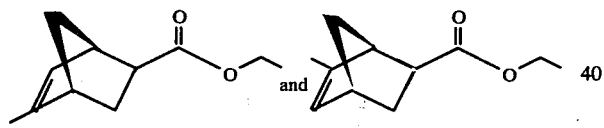

Figure 40A:
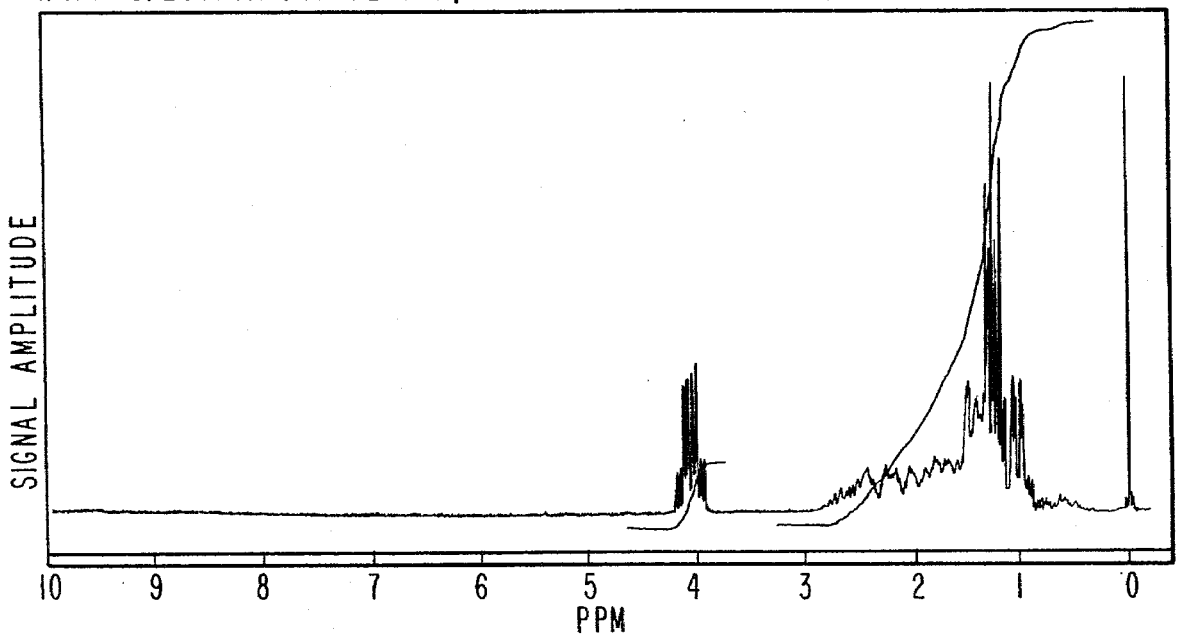
Figure 40:
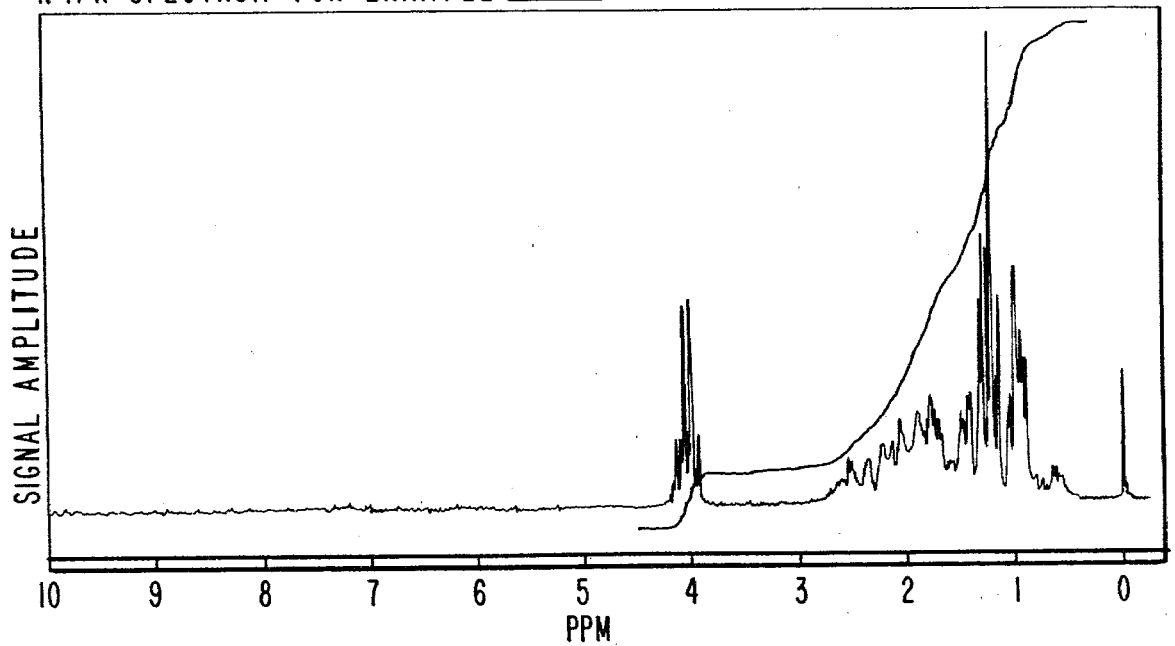

FIG. 40-A is the NMR spectrum for Fraction 2, Peak 1 of the distillation product of the reaction product of Example XXXIV containing the compounds having the structures:

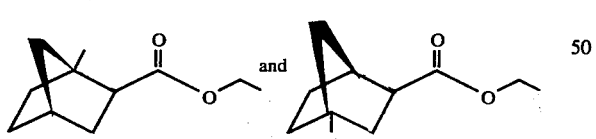

FIG. 40-B is the NMR spectrum for Fraction 10, Peak 2 of the distillation product of the reaction product of Example XXXIV containing the compounds having the structures:

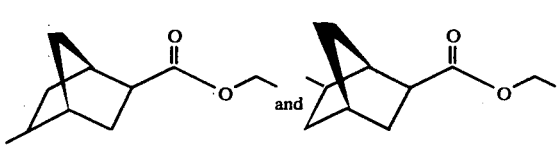

Figure 41:
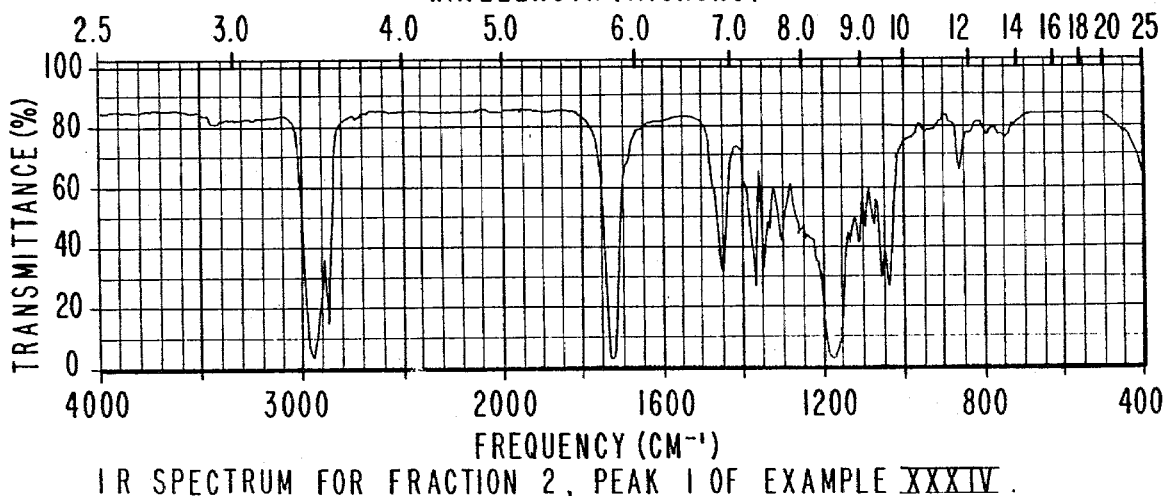

FIG. 41-A is the infra-red spectrum for Fraction 2, Peak 1 of the distillation product of the reaction product of Example XXXIV containing the compounds having the structures:

FIG. 41-B is the infra-red spectrum for Fraction 10, Peak 2 of the distillation product of the reaction product of Example XXXIV containing the compounds having the structures:

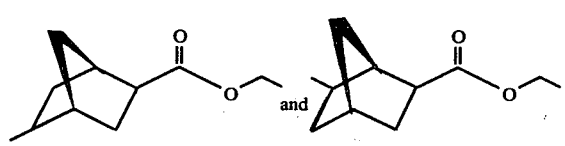

Figure 42:
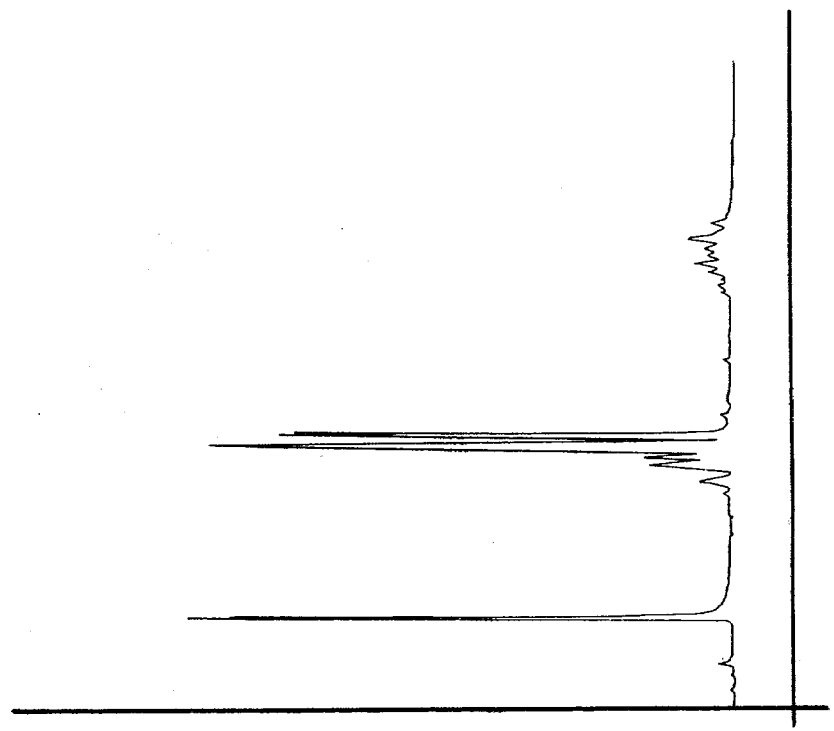

FIG. 42 is the GLC profile for the reaction product of Example XXXV containing the compounds having the structures:

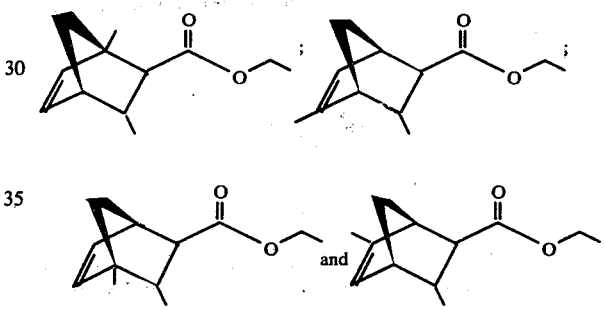

Figure 43:
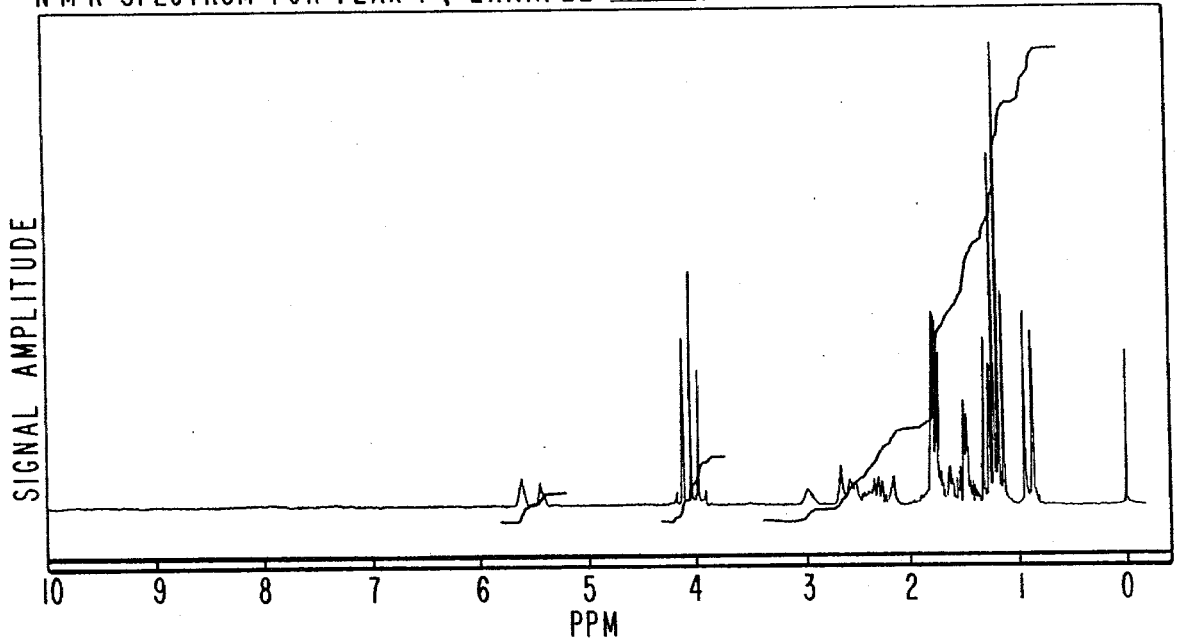
Figure 43:
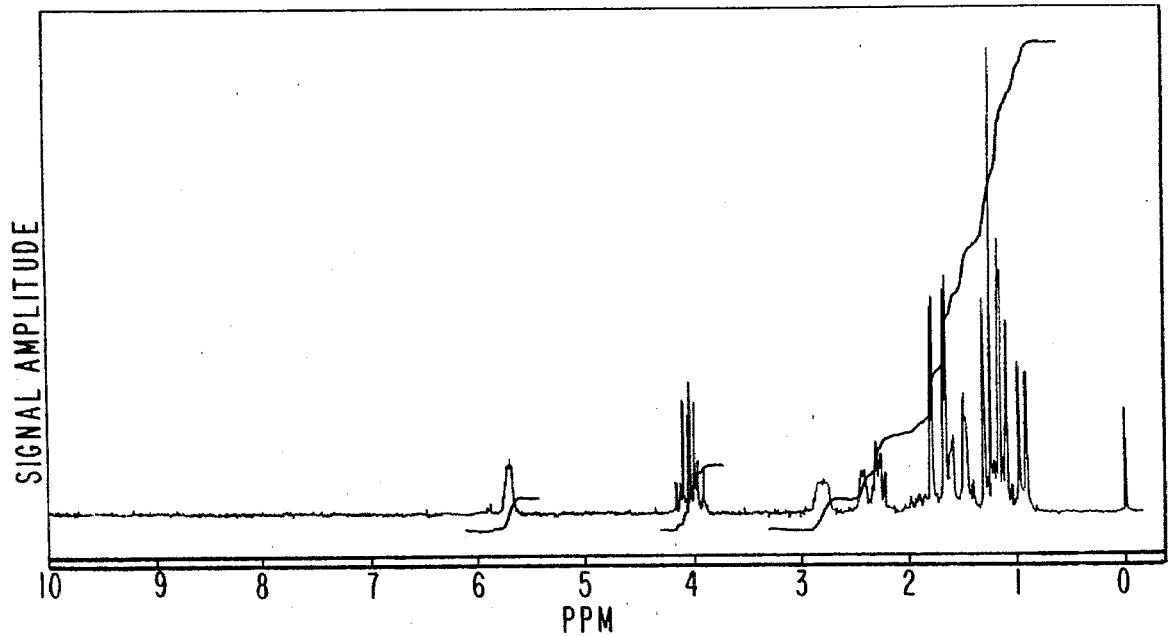

FIG. 43-A is the NMR spectrum for Peak 1 of the GLC profile of FIG. 42 of the reaction product of Example XXXV containing the compound having the structure:

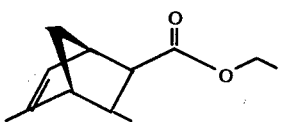

FIG. 43-B is the NMR spectrum for Peak 2 of the GLC profile of FIG. 42 for the reaction product of Example XXXV containing the compound having the structure:

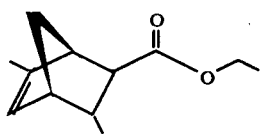

Figure 44A:
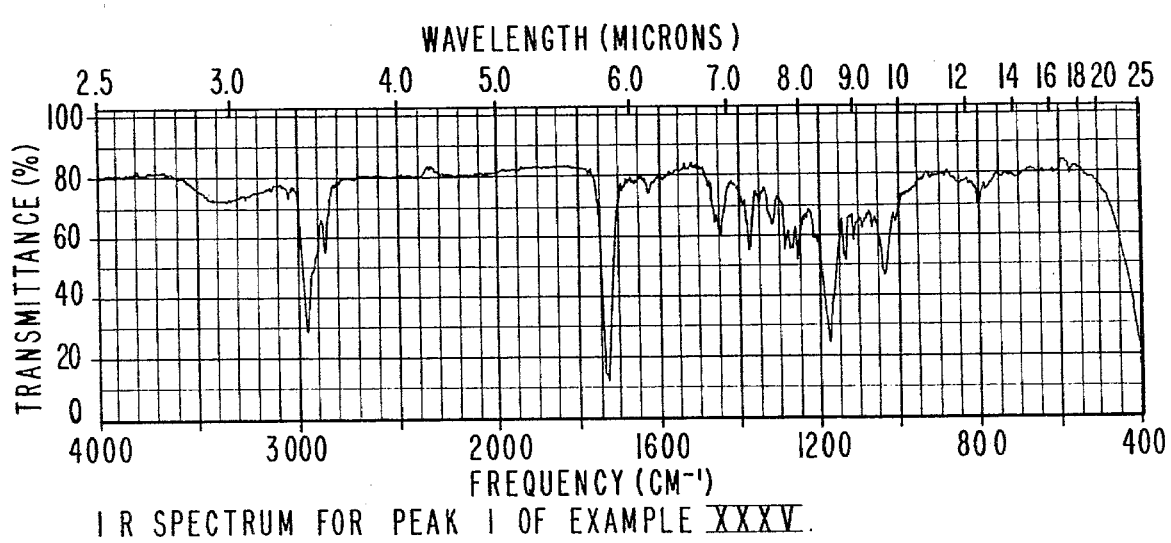
Figure 44B:
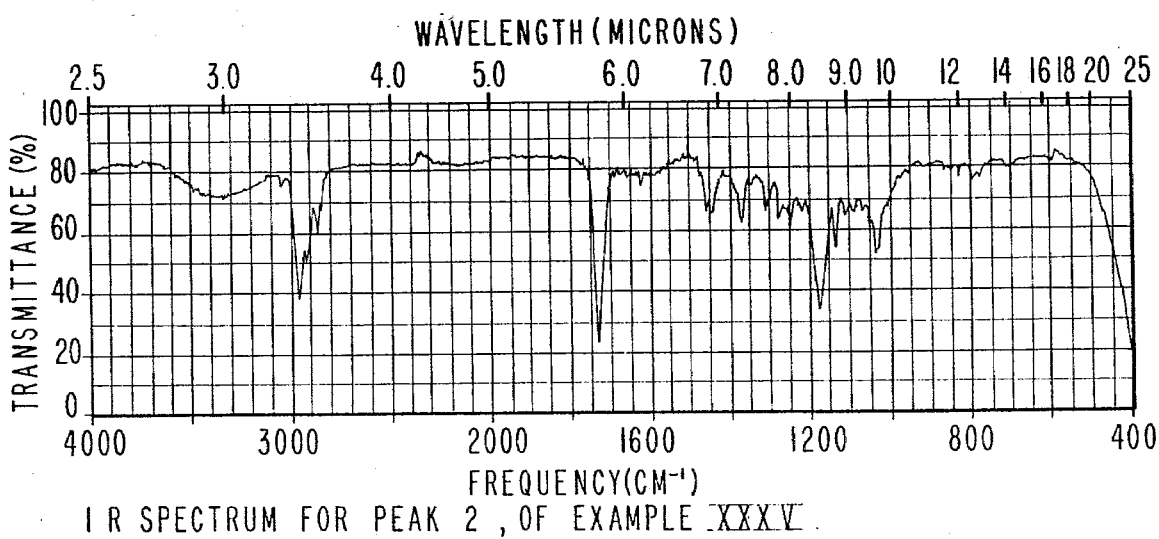

FIG. 44-A is the infra-red spectrum for Peak 1 of the GLC profile of FIG. 42 of the reaction product of Example XXXV containing the compound having the structure:

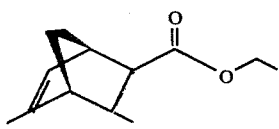

FIG. 44-B is the infra-red spectrum for Peak 2 of the GLC profile of FIG. 42 of the reaction product of Example XXXV containing the compound having the structure:

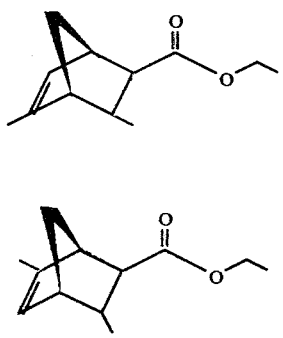

THE INVENTION

It has now been discovered that novel solid and liquid foodstuff, chewing gum, medicinal product and toothpaste compositions and flavoring compositions therefor having the fruity, burnt fruit, raspberry, seedy, sweet, berry-like, red berry-like, blueberry-like, spicy, black pepper-like, herbaceous, clove-like, vermouth-like, strawberry-like, wild strawberry-like, camphoraceous and balsamic aroma characteristics and flavor characteristics as well as bitter taste characteristics; as well as novel smoking tabocco and smoking tobacco flavoring compositions having spicy, cooling, clove-like, cinnamon bark-like, sweet, fruity, berry-like, juicyfruit, woody, piney, blueberry, banana, green, herbaceous, strawberry-like and dill aroma and taste prior to and on smoking in both the mainstream and the sidestream; as well as novel perfume compositions, colognes and perfumed articles (e.g., solid or liquid anionic, cationic, nonionic or zwitterionic detergents, fabric softeners and dryer-added fabric softener articles) having intense and long lasting fruity, banana, creamy, camphoraceous, strawberry-like, raspberry, reseda body-like, herbaceous, sweet, spicy, woody, eucalyptol-like, rum/butterscotch-like, balsamic, green, minty, borneol-like, and medicinal aromas with strong camphor, minty and calamnus-like undertones may be provided by utilization of one or more of the substituted norbornane derivatives having the generic structure:

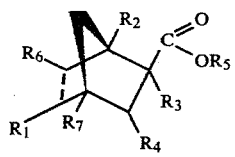

wherein the dashed line represents either a carbon-carbon single bond or a carbon-carbon double bond and $R_1$, $R_2$, $R_3$, $R_4$, $R_6$ and $R_7$ represent either hydrogen or methyl with the proviso that one of $R_1$, $R_2$, $R_6$ and $R_7$ is methyl and each of the other of $R_1$, $R_2$, $R_6$ and $R_7$ is hydrogen; and with the further proviso that $R_3$ and $R_4$ are not both methyl, in foodstuffs, chewing gums, toothpastes, medicinal products, perfume compositions, perfumed articles, colognes and smoking tobaccos as well as smoking tobacco substitutes.

Unless otherwise specified, representations herein are intended to indicate "cis" isomers, "trans" isomers, mixtures of "cis" and "trans" isomers and "endo" isomers and "exo" isomers with respect to the norbornane ring moiety and dextro and levvortatory isomers as well as racemic mixtures of optical isomers of the norbornance derivatives of our invention.

Thus, the generic structure:

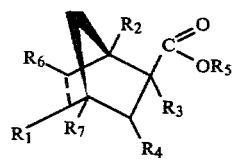

is intended to mean both "endo" and "exo" isomers having the structures:

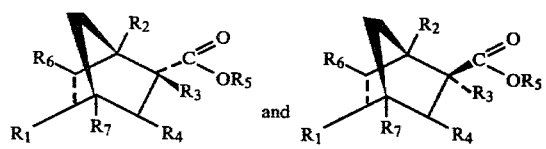

The novel substituted norbornane derivatives of our invention useful as indicated supra may be produced by reacting a 1-methylcylopentadiene or 2-methylcyclopentadiene having one of the structures:

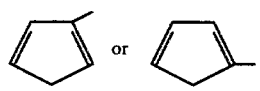

or a mixture of these methylcyclopentadienes defined according to the generic structure:

with an alkyl acrylate derivative defined according to the generic structure:

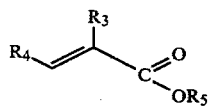

in the presence of a specific Lewis acid catalyst at relatively low temperatures (e.g., 0°–50° C.) or in the absence of a catalyst at relatively high temperatures (e.g., 170°–250° C.).

When using the catalytic process of our invention, an isomer mix will be produced which contains isomers in proportions and (in some cases) having structures different from the proportions and (in some cases) structures produced using the high temperature reaction of our invention (which reaction is carried out in the absence of catalyst).

The reactant having the structure:

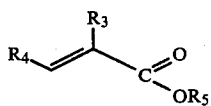

represents a "cis" isomer or a "trans" isomer or a mixture of "cis" and "trans" isomers. Thus, the "trans" isomer may be represented by the structure:

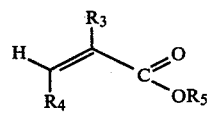

and the "cis" isomer may be represented by the structure:

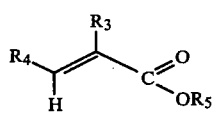

When performing the process for preparing compounds useful in the practice of our invention where the use of a catalyst is required, the catalyst for the reaction may be an alkyl aluminum dihalide or a dialkyl aluminum halide for example $RAlCl_2$ or $R_2AlCl$ wherein R represents methyl, ethyl or n-propyl or i-propyl. The preferred catalyst is ethyl aluminum dichloride. Other Lewis acids such as aluminum trichloride, stannic chloride, zinc chloride, ferric chloride and titanium tetrachloride have been attempted to be used but such attempts have proved to be unsuccessful with minimal or no yields of product being produced. The temperature range of the reaction may vary from about 0° C. up to about 50° C. with ambient temperatures, from 20° up to 30° C. being preferred. The reaction pressure will not affect the yield but conveniently and economically, a reaction pressure of atmospheric is preferred. Thus, the catalyst for the reaction may be defined according to the formula: $R_m' AlCl_n$ wherein R' is $C_1-C_3$ alkyl and the sum, m+n, equals 3; with m being one or two and n being one to two.

The reaction mass resulting from the catalytic process is a mixture of compunds containing unsaturation in the norbornane moieties defined according to the generic structures:

When performing the reaction for preparing compounds useful in the practice of our invention in the absence of catalysts (that is where no catalyst is required), the reaction temperature is in the range of from about 170° C. up to about 250° C. with a temperature of 200° C. being preferred. When the reaction is carried out at such high temperatures, the reaction is carried out under pressures greater than atmospheric in a closed pressurized system. The pressure of reaction may vary from about 10 psig up to about 100 psig depending on the vapor pressure of the reaction mass and depending upon the temperature at which it is desired to carry out the reaction. Thus, reaction pressures of between 10 psig and 100 psig will not in and of themselves affect the yield of product although too high a temperature of reaction will affect the yield of product in view of the higher degree of decomposition and too low a reaction temperature will affect the yield of product in that the reaction will take an inordinately long period of time in order to achieve a given yield. Thus, it appears that the optimum reaction temperature in the absence of catalyst is 200° C. Reaction temperatures below 170° C. will not be high enough to effect the initiating decomposition of the dimethyl dicyclopentadiene starting material which it is most practical to use as a precursor of the dimethyl dicyclopentadiene.

The reaction mass resulting from the "thermal-non-catalytic" process is also a mixture of compounds containing unsaturation in the norbornane moiety defined according the the generic structures:

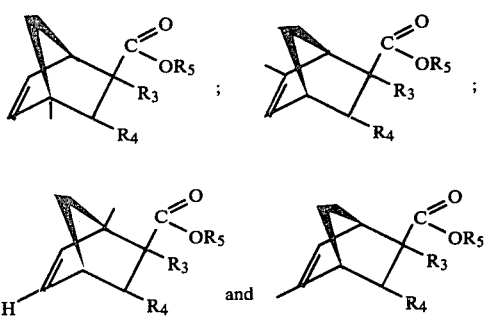

wherein $R_3$, $R_4$ and $R_5$ are as defined above.

The above unsaturated compounds may be used "as is" for their individual organoleptic properties or mixtures of compounds may be used "as is" for their organoleptic properties or the compounds individually or in admixture may be further hydrogenated using hydrogen gas at super atmospheric pressures. When it is desired to use the compounds "as is" for their organoleptic properties, it is referable to refine the reaction mass as by fractional distillation or high pressure liquid chromatography thereby creating one or more products usable as set forth above.

When it is desired to carry out a hydrogenation, the hydrogenation is carried out preferably on mixtures of products containing compounds having unsaturation prepared by the above named Diels-alder reactions. Thus, when carrying out the hydrogenation on a mixture of products containing compounds resulting from the catalytic process and having the structures:

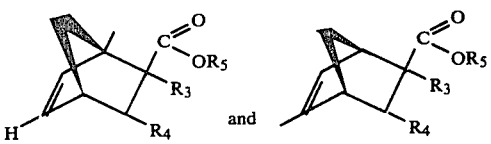

wherein $R_3$, $R_4$ and $R_5$ are defined as above, compounds having the structures:

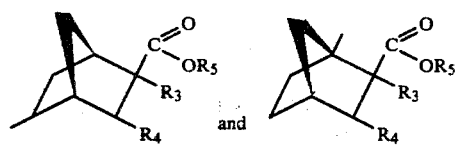

will be produced.

When carrying out the hydrogenation on a mixture of products containing the compounds resulting from the noncatalytic, thermal process and having the structures:

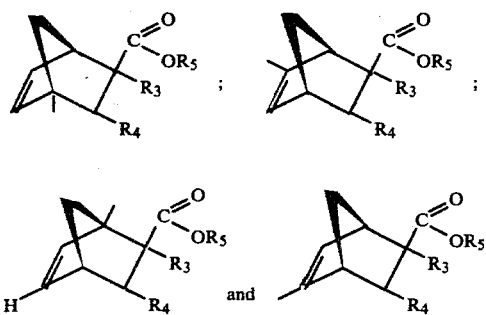

the compounds having the structures:

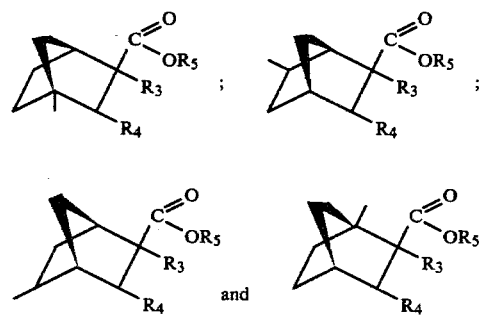

will be produced.

In either case, it is preferably to carry out the hydrogenation at pressures of from about 20 psig up to about 2,000 psig with a pressure range of from about 40 up to about 80 psig being preferred. It is also preferable for the reaction to be carried out in the presence of a catalyst such as Raney Nickel, palladium on carbon, palladium on calcium carbonate, palladium on barium surfate and platinum. When using the palladium-salt catalyst, it is preferred to use from about 3% up to about 12% palladium on salt, for example 5% palladium on calcium carbonate.

Thus, the reaction sequence which is embodied within our invention when using the catalytic procedure may be illustrated as follows:

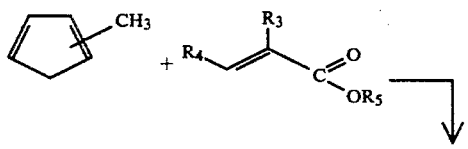

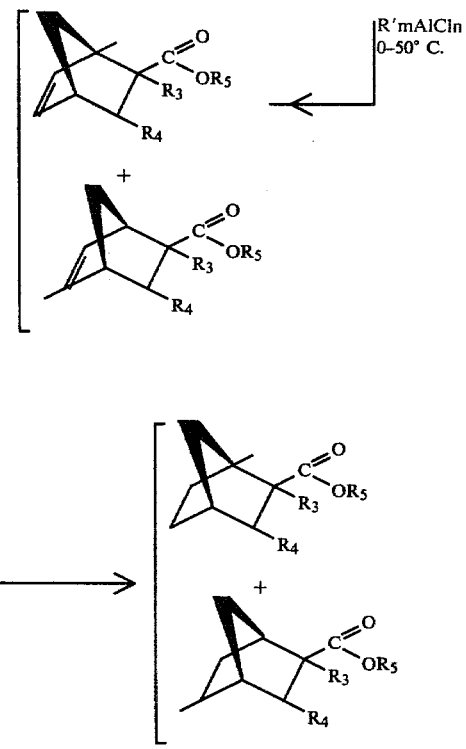

wherein one of $R_3$ and $R_4$ is hydrogen and the other of $R_3$ or $R_4$ is methyl; wherein $R_5$ represents $C_1$-$C_4$ lower alkyl; wherein $R'$ represents $C_1$-$C_3$ alkyl; and wherein M+N equals three with M being equal to one or two and N being equal to one or two.

Furthermore, the reaction sequence which is embodied within our invention when using the high temperature noncatalytic thermal Diels-alder reaction may be illustrated as follows:

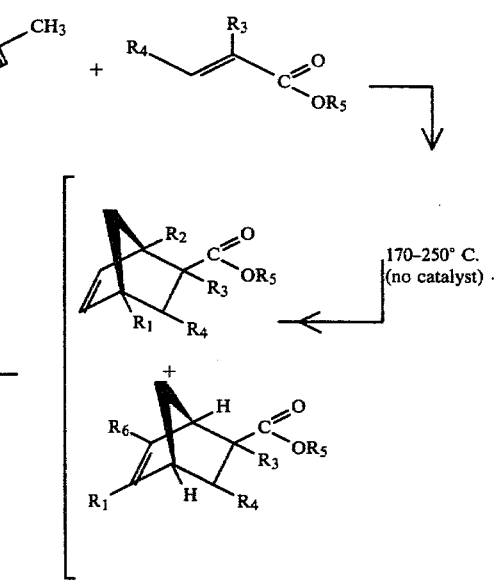

23
-continued

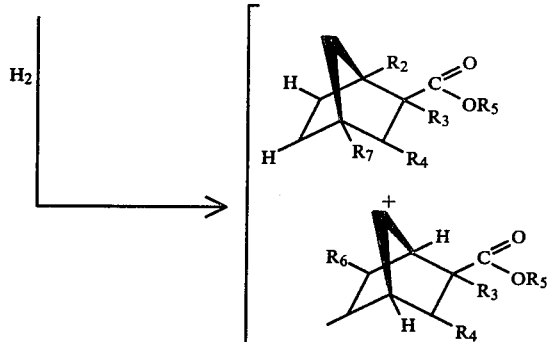

wherein $R_1$, $R_2$, $R_3$, $R_4$, $R_5$, $R_6$ and $R_7$ are as defined above.

The following tables set forth the products covered by our invention and the alkyl acrylate precursor reactant starting materials to be reacted with the methylcyclopentadienes to produce said products and in addition sets forth the organoleptic properties of the products of our invention:

TABLE I

| Alkylacrylate Reactant | Reaction Product Names | Reaction Product Structures |
|---|---|---|
| Methylcrotonate (catalytic Diels-alder reaction) | Methyl ester of 1,3- and 3,5-dimethyl norbornene-2-carboxylic acid | 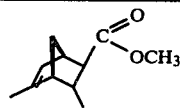 and 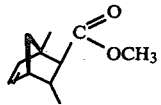 |
| Methylcrotonate (catalytic Diels-alder reaction) | Methyl ester of 1,3- and 3,5-dimethyl norbornane-2-carboxylic acid | 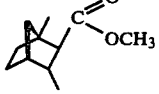 and 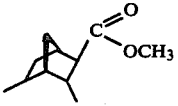 |
| Ethylcrotonate (catalytic Diels-alder reaction) | Ethyl ester of 1,3- and 3,5-dimethyl norbornene-2-carboxylic acid | 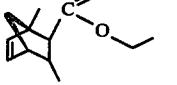 and 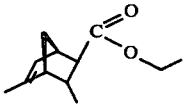 |
| Ethylacrylate (catalytic Diels-alder reaction) | Ethyl ester of 1- and 5-methyl-5-norbornene-2-carboxylic acid | 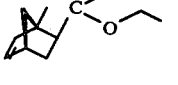 and 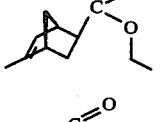 |
| Ethylacrylate (catalytic Diels-alder reaction) | Ethyl ester of 1- and 5-methyl-norbornane-2-carboxylic acid | 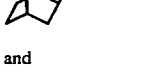 and  |

TABLE I-continued

| Alkylacrylate Reactant | Reaction Product Names | Reaction Product Structures |
|---|---|---|
| | | 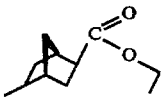 |
| n-Butylacrylate (catalytic Diels-alder reaction) | n-Butyl ester of 1- and 5-methyl-5-norbornene-2-carboxylic acid | 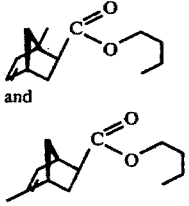<br>and<br>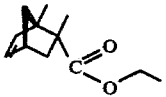 |
| Ethylmethacrylate (catalytic Diels-alder reaction) | Ethyl esters of 1,2- and 2,5-dimethyl-5-nor-bornene-2-carboxylic acid | 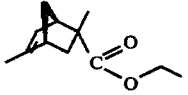<br>and<br>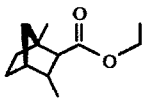 |
| Ethylcrotonate (catalytic Diels-alder reaction) | Ethyl ester of 1,3-and 3,5-dimethyl norbornane-2-carboxylic acid | 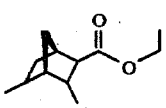<br>and<br> |
| Isopropylacrylate (thermal non-catalytic Diels-alder reaction) | Isopropyl ester of 5- and 6-methyl-5-norbornane-2-carboxylic acid | 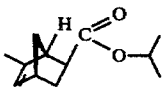<br>and<br>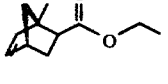 |
| Ethylacrylate | Ethyl esters of 1-; 4-; 5-; and 6-methyl-5-norbornane-2-carboxylic acid | 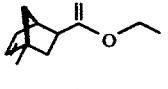<br>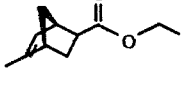<br>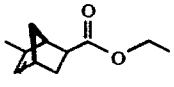<br>and<br> |

TABLE I-continued

| Alkylacrylate Reactant | Reaction Product Names | Reaction Product Structures |
|---|---|---|
| Ethylacrylate (thermal Diels-alder non-catalytic reaction) | Ethyl ester of 1-; 4-; 5-; and 6-methyl-norbornane-2-carboxylic acid | 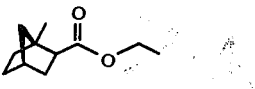<br>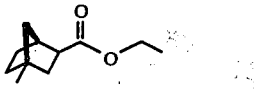<br>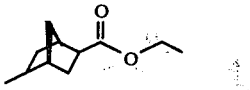<br>and<br>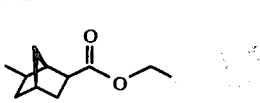 |
| Ethylcrotonate (non-catalytic thermal Diels-alder reaction) | Ethyl esters of 3,5- and 3,6-di-methyl-5-norbornane-2-carboxylic acid | 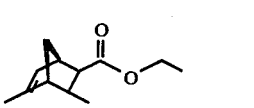<br>and<br>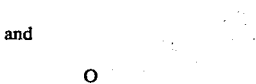 |

TABLE II

| Reaction Product Name | Fragrance Properties | Flavor Properties | Smoking Tobacco Flavor Properties |
|---|---|---|---|
| Methyl ester of 1,3- and 3,5-dimethyl norbornene-2-carboxylic acid (catalytic Diels-alder reaction) | A fruity, banana, creamy aroma with camphoraceous and minty undertones | A burnt fruit aroma and taste at 0.1 ppm | Sweet, fruity, berry-like, woody aroma prior to smoking and a sweet, fruity aroma on smoking both in the main- and sidestreams |
| Methyl ester of 1,3- and 3,5-dimethyl norbornane-2-carboxylic acid (catalytic Diels-alder reaction) | A fruity, camphoraceous and herbaceous aroma | A fruity and blackberry-like aroma and taste at 0.1 ppm | Prior to smoking a sweet, woody, spicy, cooling and clove-like aroma profile; and on smoking a sweet, spicy, cooling and woody aroma and taste in both the main stream and the side stream |
| Ethyl ester of 1,3- and 3,5-dimethyl norbornene-2-carboxylic acid (catalytic Diels-alder reaction) | A sweet, spicy herbal, woody, eucalyptol-like aroma profile with a distinct calamnus undertone with tagett-like nuances on dryout | A sweet, fruit, berry-like, spicy, black pepper-like, herbaceous, clove-like aroma and taste profile at 10 ppm causing it to be useful in blueberry, tobacco, clove and raspberry flavor foodstuffs | A sweet, fruity, berry, spicy, cinnamon bark-like and clove-like aroma and taste profile prior to and on smoking in the main stream and the side stream |
| Ethyl ester of | A sweet, fruity | A sweet, fruity | A fruity, banana- |

TABLE II-continued

| Reaction Product Name | Fragrance Properties | Flavor Properties | Smoking Tobacco Flavor Properties |
|---|---|---|---|
| 1- and 5-methyl-5-norbornene-2-carboxylic acid (catalytic Diels-alder reaction) | (banana-like) creamy and minty aroma profile with the minty notes outstanding on dryout | red berry-like, raspberry and seedy aroma and taste profile with an additional strawberry taste nuance at 0.02 ppm causing it to be useful in red berry, cherry, raspberry and strawberry flavors | like, green and strawberry-like aroma and taste both prior to and on smoking in the main stream and in the side stream |
| Ethyl ester of 1- and 5-methyl-5-norbornane-2-carboxylic acid (catalytic Diels-alder reaction) | A fruity, banaan like, and creamy aroma profile | A sweet, fruity, raspberry, vermouth-like and blueberry aroma with fruit, raspberry and blueberry taste characteristics at 0.01 ppm and at 1 ppm causing it to be useful for vermouth, blueberry and raspberry flavors and mouthwash and toothpaste flavors | A sweet, fruity, "juicyfruit", woody, piney, and blueberry aroma and taste profile prior to and on smoking in the mainstream, and in the side stream |
| n-Butyl ester of 1- and 5-methyl-5-norbornene-2-carboxylic acid (catalytic Diels-alder reaction) | A balsamic and rum/butterscotch aroma profile | A fruity, strawberry, blueberry and balsamic aroma profile with blueberry, balsamic and bitter taste characteristics at 2 ppm | An earthy, mushroom aroma prior to and on smoking |
| Ethyl esters of 1,2- and 2,5-dimethyl-5-norbornene-2-carboxylic acid (catalytic Diels-alder reaction) | A green, minty, borneol-like, spicy, somewhat medicinal aroma profile reminiscent of pepacuana boric extract | A fruit, raspberry and seedy aroma and taste profile with additional bitter taste nuances at 0.2 ppm | A sweet, green, herbaceous, dill and fruity aroma and taste profile both prior to and on smoking in mainstream and in the side stream |
| Ethyl esters of 1,3- and 3,5-dimethyl-5-norbornane-2-carboxylic acid (catalytic Diels-alder reaction) | A fruity, piney, herbaceous and cassis aroma profile with calamnus undertones | A fruity, blueberry and herbaceous aroma character with a sweet, fruity and blueberry flavor characteristic at 0.02 parts per million | |
| Isopropyl ester of 5- and 6-methyl-5-norbornane-2-carboxylic acid (thermal non-catalytic Diels-alder reaction) | A green, fruity aroma | A camphoraceous blueberry and wild strawberry aroma and flavor profile at 0.1 ppm | |
| Ethyl esters of 1-; 4-; 5-; and 6-methyl-5-norbornane-2-carboxylic acid (thermal non-catalytic Diels-alder reaction) | A sweet, fruity, minty aroma | Sweet, fruity, raspberry aroma with strawberry nuances | A fruity, natural tobacco aroma and taste both prior to and on smoking in the main stream and the side stream |

TABLE II-continued

| Reaction Product Name | Fragrance Properties | Flavor Properties | Smoking Tobacco Flavor Properties |
|---|---|---|---|
| Ethyl ester of 1-; 4-; 5-; and 6-methyl-norbornane-2-carboxylic acid (thermal non-catalytic Diels-alder reaction) | A fruity, banana and creamy aroma profile | A raspberry aroma and taste with blueberry nuances at 0.05 ppm | A sweet, fruity "juicy-fruit" aroma and taste profile both prior to and on smoking in the main stream and in the side stream |
| Ethyl esters of 3,5- and 3,6-dimethyl-5-norbornane-2-carboxylic acid (thermal non-catalytic Diels-alder reaction) | An intense, fruity, strawberry-like, raspberry-like, reseda body-like aroma but does not have cagett nuances | A sweet, fruity, clove-like aroma and taste profile at 4 ppm | A sweet, fruity, spicy clove-like aroma and taste both prior to and on smoking in the main stream and the side stream |

When the norbornane derivatives of our invention are used as food flavor adjuvants, the nature of the co-ingredients included with each of the said norbornane derivatives in formulating the product composition will also serve to alter, modify, augment or enhance the organoleptic characteristics of the ultimate foodstuff treated therewith.

As used herein in regard to flavors, the terms "alter", "modify" and "augment" in their various forms mean "supplying or imparting flavor character or note to otherwise bland, relatively tasteless substances or augmenting the existing flavor characteristic where a natural flavor is deficient in some regard or supplementing the existing flavor impression to modify its quality, character or taste".

The term "enhance" is used herein to mean the intensification of a flavor or aroma characteristic or note without the modification of the quality thereof. Thus, "enhancement" of a flavor or aroma means that the enhancement agent does not add any additional flavor note.

As used herein, the term "foodstuff" includes both solid and liquid ingestible materials which usually to, but need not, have nutritional value. Thus, foodstuffs include soups, convenience foods, beverages, dairy products, candies, vegetables, cereals, soft drinks, snacks and the like.

As used herein, the term "medicinal product" includes both solids and liquids which are ingestible non-toxic materials which have medicinal value such as cough syrups, cough drops, aspirin and chewable medicinal tablets.

The term "chewing gum" is intended to mean a composition which comprises a substantially water-insoluble, chewable plastic gum base such as chicle, or substitutes therefor, including jelutong, guttakay, rubber or certain comestible natural or synthetic resins or waxes. Incorporated with the gum base in admixture therewith may be plasticizers of softening agents, e.g., glycerine; and a flavor composition which incorporates one or more of the norbornane derivatives of our invention, and in addition, sweetening agents which may be sugars, including sucrose or dextrose and/or artificial sweeteners such as cyclamates or saccharin. Other optional ingredients may also be present.

Substances suitable for use herein as co-ingredients or flavoring adjuvants are well known in the art for such use, being extensively described in the relevant literature. It is a requirement that any such material be "ingestibly" acceptable and thus non-toxic and otherwise non-deleterious particularly from an organoleptic standpoint whereby the ultimate flavor and/or aroma of the consumable material used is not caused to have unacceptable aroma and taste nuances. Such materials may in general be characterized as flavoring adjuvants or vehicles comprising broadly stabilizers, thickeners, surface active agents, conditioners, other flavorants and flavor intensifiers.

Stabilizer compounds include preservatives, e.g., sodium chloride; antioxidants, e.g., calcium and sodium ascorbate, ascorbic acid, butylated hydroxyanisole (mixture of 2- and 3-tertiary-butyl-4-hydroxyanisole), butylated hydroxytoluene (2,6-di-tertiary-butyl-4-methylphenol), propyl gallate and the like and sequestrants, e.g., citric acid.

Thickener compounds include carriers, binders, protective colloids, suspending agents, emulsifiers and the like, e.g., agar agar, carrageenan; cellulose and cellulose derivatives such as carboxymethyl cellulose and methyl cellulose; natural and synthetic gums such as gum arabic, gum tragacanth; gelatin, proteinaceous materials; lipids; carbohydrates; starches, pectins and emulsifiers, e.g., mono- and diglycerides of fatty acids, skim milk powder, hexoses, pentoses, disaccharides, e.g., sucrose corn syrup and the like.

Surface active agents includes emulsifying agents, e.g., fatty acids such as capric acid, caprylic acid, palmitic acid, myristic acid and the like, mono- and diglycerides of fatty acids, lecithin, defoaming and flavor-dispersing agents such as sorbitan monostearate, potassium stearate, hydrogenated tallow alcohol and the like.

Conditioners include compounds such as bleaching and maturing agents, e.g., benzoyl peroxide, calcium peroxide, hydrogen peroxide and the like; starch modifiers such as peracetic acid, sodium chlorite, sodium hypochlorite, propylene oxide, succinic anhydride and the like, buffers and neutralizing agents, e.g., sodium acetate, ammonium bicarbonate, ammonium phosphate, citric acid, lactic acid, vinegar and the like; colorants, e.g., carminic acid, cochineal, tumeric and curcuma and the like; firming agents such as aluminum sodium sulfate, calcium chloride and calcium gluconate; texturizers, anti-caking agents, e.g., aluminum calcium sulfate and tri-basic calcium phosphate; enzymes; yeast foods, e.g., calcium lactate and calcium sulfate; nutrient supplements, e.g., iron salts such as ferric phosphate, ferrous gluconate and the like, riboflavin, vitamins, zinc sources such as zinc chloride, zinc sulfate and the like.

Other flavorants and flavor intensifiers include aldehydes, esters, natural oils, alcohols, sulfides, ketones, lactones, carboxylic acids and hydrocarbons such as heliotropin, terpinenol-4, benzaldehyde, anisaldehyde, phenyl acetaldehyde, benzyl formate, benzyl acetate, cis-3-hexenyl benzoate, methyl hexanoate, hexanal, eucalyptol, eugenol, acetaldehyde, ethyl acetate, ethyl butyrate, turpentine gum oil, limonene, gum camphor, isobornyl acetate, borneol, cinnamic aldehyde, cuminic aldehyde, furfural, methyl cinnamate, cassia oil, vanillin, maltol, parahydroxybenzyl acetate, dimethyl sulfide, alphaionone, acetic acid, isobutyl acetate, acetone, butyric acid, formic acid, valeric acid, amyl acetate, amyl butyrate, anethol, benzyl salicylate, diacetyl, dimethyl anthranilate, ethyl methylphenylglycidate, ethyl succinate, ethyl valerate, geraniol, cis-3-hexen-1-ol, 2-hexenyl acetate, 2-hexenyl butyrate, hexyl butyrate, 4-(p-hydroxyphenyl)-2-butanone, betaionone, isobutyl cinnamate, jasmine, lemon essential oil, methyl butyrate, methyl caproate, methyl disulfide, methyl p-naphthyl ketone, orris butter, rose absolute, terpenyl acetate, gamma-undecalactone, vanilla and alcohol.

The specific flavoring adjuvant selected for use may be either solid or liquid depending upon the desired physical form of the ultimate product, i.e., foodstuff, whether simulated or natural, and should, in any event, (i) be organoleptically compatible with the norbornane derivatives of our invention by not covering or spoiling the organoleptic properties (aroma and/or taste) thereof; (ii) be non-reactive with the norbornane derivatives of our invention and (iii) be capable of providing an environment in which the norbornane derivatives can be dispersed or admixed to provide a homogeneous medium. In addition, selection of one or more flavoring adjuvants, as well as the quantities thereof will depend upon the precise organoleptic character desired in the finished product. Thus, in the case of flavoring compositions, ingredient selection will vary in accordance with the foodstuff, chewing gum, medicinal product or toothpaste to which the flavor and/or aroma are to be imparted, modified, altered or enhanced. In contradistinction, in the preparation of solid products, e.g. simulated foodstuffs, ingredients capable of providing normally solid compositions should be selected such as various cellulose derivatives.

As will be appreciated by those skilled in the art, the amount of norbornane derivatives employed in a particular instance can vary over a relatively wide range, depending upon the desired organoleptic effects to be achieved. Thus, correspondingly, greater amounts would be necessary in those instances wherein the ultimate food composition to be flavored is relatively bland to the taste, whereas relatively minor quantities may suffice for purposes of enhancing the composition merely deficient in natural flavor or aroma. The primary requirement is that the amount selected to be effective, i.e., sufficient to alter, modify, or enhance the organoleptic characteristics of the parent composition, whether foodstuff per se, chewing gum, per se, medicinal product per se, toothpaste per se, or flavoring composition.

The use of insufficient quantities of norbornane derivatives will, of course, substantially vitiate any possibility of obtaining the desired results while excess quantities prove needlessly costly and, in extreme cases, may disrupt the flavor-aroma balance, thus proving self-defeating. Accordingly, the terminology "effective amount" and "sufficient amount" is to be accorded a significance in the context of the present invention consistent with the obtention of desired flavoring effects.

Thus, and with respect to ultimate food compositions, chewing gum compositions, medicinal product compositions and toothpaste compositions, it is found that quantities of norbornane derivatives ranging from a small but effective amount, e.g., 0.01 parts per million up to about 100 parts per million based on total composition are suitable. Concentrations in excess of the maximum quantity stated are not normally recommended, since they fail to prove commensurate enhancement of organoleptic properties. In those instances, wherein the norbornane derivatives are added to the foodstuff as an integral component of a flavoring composition, it is, of course, essential that the total quantity of flavoring composition employed be sufficient to yield an effective norbornane derivative concentration in the foodstuff product.

Food flavoring compositions prepared in accordance with the present invention preferably contain the norbornane derivatives in concentrations ranging from about 0.01% up to about 15% by weight based on the total weight of the said flavoring composition.

The composition described herein can be prepared according to conventional techniques well known as typified by cake batters and fruit drinks and can be formulated by merely admixing the involved ingredients within the proportions stated in a suitable blender to obtain the desired consistency, homogeneity of dispersion, etc. Alternatively, flavoring compositions in the form of particulate solids can be conveniently prepared by mixing the norbornane derivatives with, for example, gum arabic, gum tragacanth, carrageenan and the like, and thereafter spray-drying the resultant mixture whereby to obtain the particular solid product. Pre-prepared flavor mixes in powder form e.g., a fruit-flavored powder mix are obtained by mixing the dried solid components, e.g., starch, sugar and the like and norbornane derivatives in a dry blender until the requisite degree of uniformity is achieved.

It is presently preferred to combine with the norbornane derivatives of our invention, the following adjuvants:
Heliotropin;
Terpinenol-4;
Benzaldehyde;
Anisaldehyde;
Phenylacetaldehyde;
Benzyl formate;
Benzyl acetate;
Cis-3-hexenyl benzoate;
Methyl hexanoate;
Hexanal;
Eucalyptol;
Eugenol;
Acetaldehyde;
Ethyl acetate;

Ethyl butyrate;
Turpentine gum oil;
Limonene;
Gum camphor;
Isobornyl acetate;
Borneol;
Cinnamic aldehyde;
Cuminic aldehyde;
Furfural;
Methyl cinnamate;
Cassia oil;
Vanillin;
Malto;
Paranydroxybenzylacetone;
Dimethyl sulfide;
Alpha-ionone;
Acetic acid;
Isobutyl acetate;
Acetone;
Butyric acid;
Formic acid;
Valeric acid;
Amyl acetate;
Amyl butyrate;
Anethol;
Benzyl salicylate;
Diacetyl;
Dimethyl anthranilate;
Ethyl methylphenylglycidate;
Ethyl succinate;
Ethyl valerate;
Geraniol;
Cis-3-hexen-1-ol;
2-Hexenyl acetate;
2-Hexenyl butyrate;
Hexyl butyrate;
4-(p-Hydroxyphenyl)-2-butanone;
Beta-ionone;
Isobutyl cinnamate;
Jasmine;
Lemon essential oil;
Methyl butyrate;
Methyl capronate;
Methyl disulfide;
Methyl p-naphthyl ketone;
Orris butter;
Rose absolute;
Terpenyl acetate;
Gamma-undecalactone;
Vanilla; and
Alcohol.

An additional aspect of our invention provides an organoleptically improved smoking tobacco product and additives therefor, as well as methods of making the same which overcome problems heretofore encountered in which desired spicy, cooling, clove-like, cinnamon bark-like, sweet, fruity, berry-like, juicyfruit, woody, piney, blueberry, banana, green, herbaceous, strawberry-like, and dill flavor characteristics of natural tobacco (prior to smoking and, on smoking, in the mainstream and in the sidestream) as well as cooling effects, are created or enhanced or modified or augmented and may be readily controlled and maintained at the desired uniform level regardless of variations in the tobacco components of the blend.

This invention further provides improved tobacco additives and methods whereby various desirable natural aromatic tobacco flavoring characteristics with spicy, cooling, clove-like, cinnamon bark-like, sweet, fruity, berry-like, juicyfruit, woody, piney, blueberry, banana, green, herbaceous, strawberry-like and dill notes may be imparted to smoking tobacco products and may be readily varied and controlled to produce the desired uniform flavoring characteristics.

In carrying out this aspect of our invention, we add to smoking tobacco materials or a suitable substitute therefor (e.g., dried lettuce leaves) an aroma and flavor additive containing as an active ingredient one or more norbornane derivatives of our invention.

In addition to the norbornane derivatives of our invention other flavoring and aroma additives may be added to the smoking tobacco material or substitute therefor either separately or in mixture with the norbornane derivatives as follows:

I. Synthetic Materials

Beta-ethyl-cinnamaldehyde;
Eugenol;
Dipentene;
Damascenone;
Maltol;
Ethyl maltol;
Delta undecalactone;
Delta decalactone;
Benzaldehyde;
Amyl acetate;
Ethyl butyrate;
Ethyl valerate;
Ethyl acetate;
2-Hexenol-1;
2-Methyl-5-isopropyl-1,3-nonadiene-8-one;
2,6-Dimethyl-2,6-undecadiene-10-one;
2-Methyl-5-isopropylacetophenone;
2-Hydroxy-2,5,5,8a-tetramethyl-1-(2-hydroxyethyl)-decahydronaphthalene;
Dodecahydro-3a,6,6,9a-tetramethylnaphtho-(2,1-b-)-furan
4-Hydroxyhexanoic acid, gamma lactone; and
Polyisoprenoid hydrocarbons defined in Example V of U.S. Pat. No. 3,589,372, issued on 6-29-71.

II. Natural Oils

Celery seed oil;
Coffee extract;
Bergamot oil;
Cocoa extract;
Nutmeg oil; and
Origanum oil.

An aroma and flavoring concentrate containing one or more norbornane derivatives of our invention and, if desired, one or more of the above indicated additional flavoring additives may be added to the smoking tobacco material, to the filter or to the leaf or paper wrapper. The smoking tobacco material may be shredded, cured, cased and blended tobacco material or reconstituted tobacco material or tobacco substitutes (e.g., lettuce leaves) or mixtures thereof. The proportions of flavoring additives may be varied in accodance with taste but insofar as enhancement or the imparting of spicy and/or cooling and/or clove-like and/or cinnamon bark-like and/or sweet and/or fruity and/or berry-like and/or juicyfruit and/or woody and/or piney and/or blueberry and/or banana and/or green and/or herbaceous and/or strawberry-like and/or dill notes, we have found that satisfactory results are obtained if the proportion by weight of the sum total of norbornane derivative(s) to smoking tobacco material is between 50 ppm and 1,500 ppm (0.015%–0.15%). We have further found that satisfactory results are obtained if the proportions by weight of the sum total of norbornane derivative used to flavoring material is between 1,500 and 15,000 ppm (0.15%–1.5%).

Any convenient method for incorporating the norbornane derivative(s) into the tobacco product may be employed. Thus, the nobornane derivative(s) taken alone or along with other flavoring additives may be dissolved in a suitable solvent such as ethanol, diethyl ether and/or volatile organic solvents and the resulting solution may either be spread on the cured, cased and blended tobacco material or the tobacco material may be dipped into such solution. Under certain circumstances, a solution of the norbornane derivative(s) taken alone or taken further together with other flavoring additives as set forth above, may be applied by means of a suitable applicator such as a brush or roller on the paper or leaf wrapper for the smoking product, or it may be applied to the filter by either spraying, or dipping, or coating.

Furthermore, it will be apparent that only a portion of the tobacco or substitute therefor need be treated and the thus treated tobacco may be blended with other tobaccos before the ultimate tobacco product is formed. In such cases, the tobacco treated by have the norbornane derivative(s) in excess of the amounts or concentrations above indicated so that when blended with other tobaccos, the final product will have the percentage within the indicated range.

In accordance with one specific example of our invention an aged, cured and shredded domestic burley tobacco is sprayed with a 20% ethanol solution of the mixture of 1,3-and 3,5-dimethyl-2-norbornane carboxylic acid methyl esters having the structures:

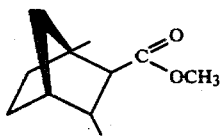

and

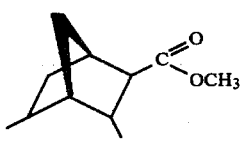

in an amount of mixture to provide tobacco composition containing 800 ppm by weight of the mixture of the two esters on a dry basis. Thereafter the alcohol is removed by evaporation and the tobacco is manufactured into cigarettes by the usual techniques. The cigarette when treated as indicated has a desired and pleasing aroma which is detectable in the mainstream and the sidestream when the cigarette is smoked. This aroma is described as being sweeter, more aromatic, more tobacco-like having sweet, spicy, cooling, woody and clove-like notes.

While our invention is particularly useful in the manufacture of smoking tobacco, such as cigarette tobacco, cigar tobacco and pipe tobacco, other tobacco products, formed from sheeted tobacco dust or fines may also be used. Likewise, the norbornane derivative(s) of our invention can be incorporated with materials such as filter tip materials (e.g. cellulose acetate filters wherein spicy, cooling, clove-like, cinnamon bark-like, sweet, fruity, berry-like, juicyfruit, woody, piney, blueberry, banana, green, herbaceous, strawberry-like and/or dill effects are desired), seam paste, packaging materials and the like which are used along with tobacco to form a product adapted for smoking. Furthermore, the norbornane derivative(s) can be added to certain tobacco substitutes of natural or synthetic origin (e.g., dried lettuce leaves) and, accordingly, by the term "tobacco" as used throughout this specification is meant any composition intended for human consumption by smoking or otherwise, whether composed of tobacco plant parts or substitute materials or both.

The norbornane derivative(s) and one or more auxiliary perfume ingredients, including, for example, hydrocarbons, alcohols, ketones, aldehydes, nitriles, esters, lactones or cyclic esters, synthetic essential oils and natural essential oils, may be admixed so that the combined odors of the individual components produce a pleasant and desired fragrance, particularly and preferably in fruity, banana, creamy, camphoraceous, herbaceous, strawberry-like, raspberry-like, reseda body-like, sweet, spicy, woody, eucalyptol-like, tagett-like, rum/butterscotch, balsamic, green, and/or minty fragrances. Such perfume compositions usually contain (a) the main note or the "bouquet": or foundation stone of the composition; (b) modifiers which round off and accompany the main note; (c) fixatives which include odorous substances which lend a particular note to the perfume throughout all stages of evaporation and substances which retard evaporation; and (d) topnotes which are usually low boiling fresh-smelling materials.

In perfume compositions, it is the individual components which contribute to their particular olfactory characteristics, however the overall sensory effect of the perfume composition will be at least the sum total of the effects of each of the ingredients. Thus, one or more of the norbornane derivative(s) of our invention can be used to alter, modify or enhance the aroma characteristics of a perfume composition, for example by utilizing or moderating the olfactory reaction contributed by another ingredient in the composition.

The amount of norboranane derivative(s) of our invention which will be effective in perfume compositions as well as perfumed articles and colognes depends on many factors, including the other ingredients, their amounts and the effects which are desired. It has been found that perfume compositions containing as little as 0.01% of norbornane derivative(s) or even less (e.g., 0.005%) can be used to impart a fruity, banana, creamy, camphoraceous, strawberry-like, raspberry-like, reseda body-like, herbaceous, sweet, spicy, woody, eucalyptol-like, rum/butterscotch, balsamic, green, minty, borneol-like, tagett-like and/or medicinal odor with camphor, minty and calamnus-like nuances to soaps, detergents (including anionic, nonionic, cationic and zwitterionic solid or liquid detergents), cosmetics, fabric softeners, dryer-added fabric softener articles, fabric whiteners and optical brighteners or other products. The amount employed can range up to 70% of the fragrance components and will depend on considerations of cost, nature of the end product, the effect desired on the finished product and the particular fragrance sought.

The norbornane derivative(s) of our invention are useful (taken alone or together with other ingredients in perfume compositions) in detergents and soaps, space odorants and deodorants, perfumes, colognes, toilet water, bath preparations, such as lacquers, brilliantines, pomades and shampoos; cosmetic preparations, such as creams, deodorants, hand lotions and sun screens; powders such as talcs, dusting powders, face powders and the like. As little of 0.005% of the nobornane derivative(s) (in the ultimate perfumed article) will suffice to impart an intense, fruity, banana, creamy, camphoraceous, strawberry-like, raspberry-like, reseda body-like, herbaceous, sweet, spicy, woody, eucalyptol-like, rum/butterscotch, balsamic, green, minty, borneol-like, tagett-like and/or medicinal note to various types of perfumed articles. Generally no more than 3% of the norbornane derivative(s) based on the ultimate end product (perfumed article) is required.

In addition, the perfume composition or fragrance composition of our invention can contain a vehicle, or carrier for the norbornane derivative(s). The vehicle can be a liquid such as a non-toxic alcohol, a non-toxic glycol or the like. The carrier can also be an absorbent solid, such as a gum (e.g., gum arabic), or components for encapsulating the composition (such as gelatin).

It will thus be apparent that the norbornane derivative(s) of our invention can be utilized to alter, modify or enhance sensory properties, particularly organoleptic properties such as flavor(s) and/or fragrance(s) of a wide variety of consumable materials.

The following examples serve to illustrate processes for specifically producing the norbornane derivative(s) useful in our invention.

The following examples also serve to illustrate specific embodiments of our invention It will be understood that these examples are illustrative and the invention is to be considered to be restricted thereto only as indicated in the appended claims.

All parts and percentages given herein are by weight unless otherwise specified.

EXAMPLE I

PREPARATION OF 1,3-DIMETHYL-5-NORBORNENE-2-CARBOXYLIC ACID METHYL ESTER AND 3,5-DIMETHYL-5-NORBORNENE-2-CARBOXYLIC ACID METHYL ESTER (CATALYTIC DIELS-ALDER REACTION)

Reaction:

Reaction:

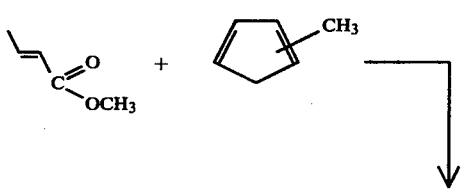

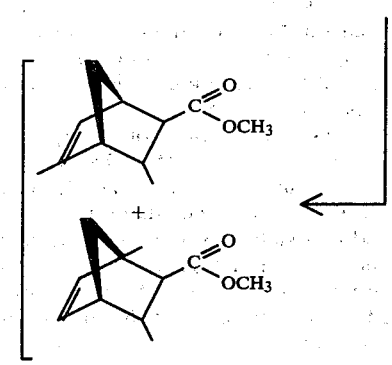

Into a 3 liter flask equipped with stirrer, thermometer, condenser, addition funnel and cooling bath are charged 1000 ml toluene, 500 grams methyl crotonate, 45 grams ethyl aluminum dichloride. The resulting mixture is cooled to 20°–25° C. Over a period of 50 minutes while maintaining the reaction mass at 24°–25° C., 320 grams of methyl cyclopentadiene (mixture of 1-methyl-1,3-cyclopentadiene and 2-methyl-1,3-cyclopentadiene (50% in toluene solution)) is added. After the completion of the addition of the methyl cyclopentadiene mixture, the reaction mass is stirred for a period of 3 hours at 21°–125° C. At the end of the three hour period the reaction mass is heated to 40° C. and the temperature is maintained at 40° C. for a period of 2.7 hours. At the end of the 207 hour period the reaction mass is cooled to 20° C. and is poured into one liter of 10% hydrochloric acid solution. The reaction mass now exists in two phases. The aqueous phase is separated from the organic phase. The aqueous phase is extracted with 500 ml toluene extract and organic phase are combined. The resulting organic phase is then washed as follows:

One 1 liter portion water;
One 1 liter portion saturated sodium carbonate;
One 1 liter portion water.

The toluene is then removed under reduced pressure. The resulting organic material is then distilled in a 12 inch Goodloe column yielding the following fractions:

| Fraction No. | Vapor Temp. (°C.) | Liquid Temp. (°C.) | mm/Hg. Pressure | Reflux Ratio | Weight of Fraction (g.) |
|---|---|---|---|---|---|
| 1 | 41/43 | 70/71 | 2.1/2.0 | 9:1 | 21.0 |
| 2 | 48 | 72 | 2.0 | 9:1 | 22.6 |
| 3 | 45 | 73 | 2.0 | 9:1 | 21.8 |
| 4 | 48 | 73 | 2.0 | 9:1 | 22.2 |
| 5 | 48 | 72 | 2.0 | 9:1 | 16.7 |
| 6 | 48 | 73 | 2.0 | 9:1 | 22.0 |
| 7 | 49 | 74 | 2.0 | 9:1 | 19.9 |
| 8 | 49 | 86 | 2.0 | 9:1 | 20.5 |
| 9 | 50/35 | 95/205 | 2.5/1.0 | 9:1 | 12.0 |

Fractions 4–7 are bulked for purposes of flavor evaluation. The bulked fractions 4–7 as analyzed by NMR, IR and mass spectral analysis contain a mixture of compounds having the structures:

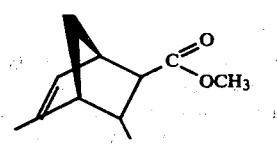

-continued and

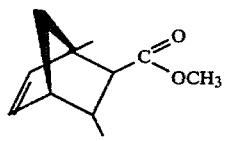

Fractions 4–7 bulked has a burnt fruit aroma and flavor characteristic at 0.1 ppm.

Fractions 4–7 bulked has a fruity, banana, creamy aroma with camphoraceous, minty undertones.

Figure 1:
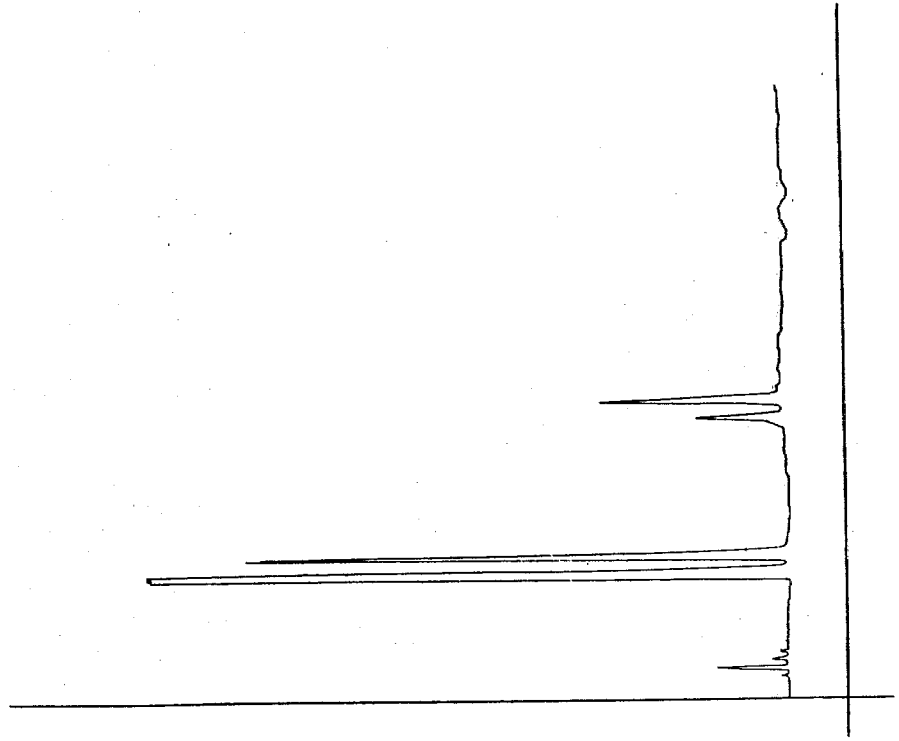
FIG. 1 sets forth the GLC profile for the reaction product of Example I containing compounds having the structures.

FIG. 1 represents the GLC profile for the reaction product of Example I containing the compounds having the structures:

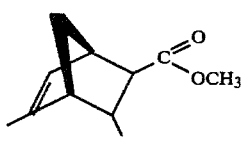

and

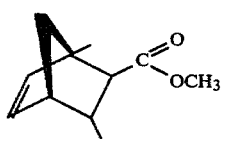

FIG. 2A represents the NMR spectrum for fraction 8 of the foregoing distillation containing only the compound having the structure:

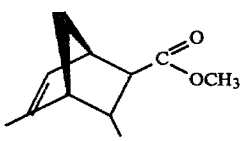

FIG. 2B represents the NMR spectrum for fraction 2 of the foregoing distillation containing the compound having the structure:

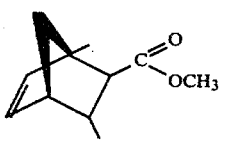

FIG. 3A represents the infrared spectrum for fraction 8 of the foregoing distillation containing only the compound having the structure:

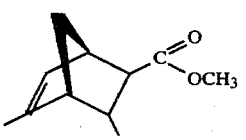

FIG. 3B represents the infrared spectrum for fraction 2 of the foregoing distillation containing only the compound having the structure:

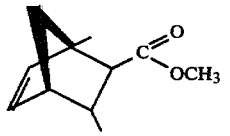

FIG. 4 represents the mass spectrum for the reaction product of Example I containing the compounds having the structures:

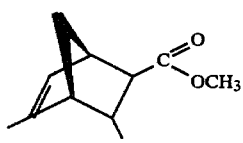

and

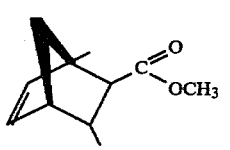

EXAMPLE II

PREPARATION OF
1,3-DIMETHYL-5-NORBORNANE-2-CARBOXYLIC ACID METHYL ESTER AND
3,5-DIMETHYL-5-NORBORNANE2-CARBOXYLIC ACID METHYL ESTER

Reaction:

Reaction:

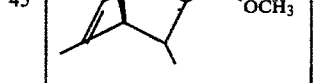
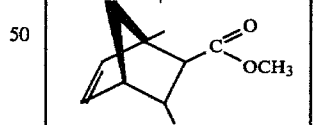

Into a 500 ml pressure bottle held in a Parr shaker is charged 100 ml isopropyl alcohol and 160 grams (0.89 moles) of the methyl cyclopentadiene/methyl crotonate adduct having the structures:

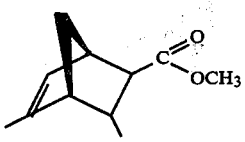

and

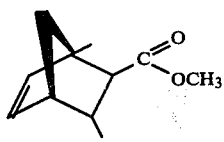

prepared according to Example I and 4 grams of Raney Nickel. The Parr shaker is purged with hydrogen and charged to 50 psig. Shaking is begun and the Parr shaker is recharged with hydrogen when necessary in order to maintain the pressure at 50 psig. A total pressure drop of 74 pounds of hydrogen is observed. A GLC profile (conditions: Carbowax column programmed at 80°–220° C. at 8° C. per minute) indicates some change. NMR analysis indicates that all of the olefin is consumed.

At the end of the reaction the pressure bottle is opened and the Raney Nickel catalyst is filtered and the solvent is stripped off under reduced pressure. The resulting residue is distilled yielding 122 grams of product. The distillation takes place on a 12"×2' Goodloe column yielding the following fractions:

| Fraction No. | Vapor Temp. (°C.) | Liquid Temp. (°C.) | mm/Hg. Pressure | Reflux Ratio | Weight of Fraction (g.) |
|---|---|---|---|---|---|
| 1 | 37/41 | 72/75 | .65/.8 | 9:1 | 21 |
| 2 | 42 | 76 | .65 | 9:1 | 25 |
| 3 | 43 | 78 | .65 | 9:1 | 23 |
| 4 | 44 | 80 | .8 | 9:1 | 19 |
| 5 | 45 | 95 | .8 | 9:1 | 22 |
| 6 | 60 | 215 | .8 | 9:1 | 12 |

NMR, mass spectral and IR analysis yields the information that the resulting product is a mixture of the compounds having the structures:

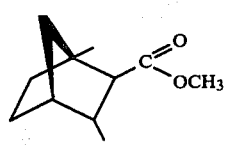

and

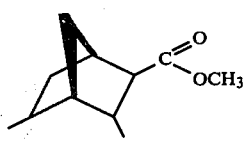

FIG. 5 sets forth the GLC profile for the reaction product produced according to this example. FIG. 6A sets forth the NMR spectrum for peak 1 of the GLC profile which consists essentially of the compound having the structure:

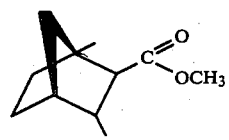

FIG. 6B sets forth the NMR spectrum for fraction 6 of the foregoing distillation which consists essentially of the compound having the structure:

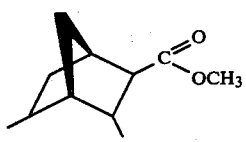

FIG. 7A sets forth the infrared spectrum for peak 1 of the foregoing GLC profile which consists essentially of the compound having the structure:

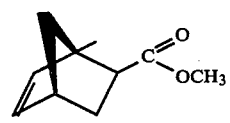

FIG. 7B sets forth the infrared spectrum for fraction 6 of the foregoing distillation which consists essentially of the compound having the structure:

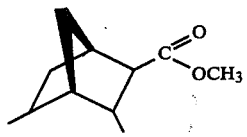

FIG. 8 sets forth a mass spectrum for the reaction product of this example which contains the compounds having the structures:

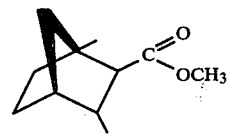

and

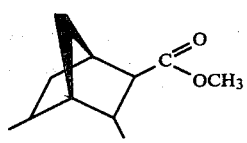

The resulting mixture, from a food flavor standpoint, has a fruity, blueberry aroma and flavor characteristic at 0.1 ppm. The resulting mixture from a fragrance standpoint, has a fruit, camphoraceous and herbaceous aroma profile.

The mixture of this example also has a sweet, woody, spicy, cooling and clove-like aroma profile prior to smoking and a sweet, spicy, cooling and woody aroma and taste profile on smoking tobacco articles in both the mainstream and the sidestream.

EXAMPLE III

PREPARATION OF THE ETHYL ESTER OF 1,3 and 3,5-DIMETHYL 5-NORBORNENE CARBOXYLIC ACID (CATALYTIC DIELS-ALDER REACTION)

Reaction:

Reaction:

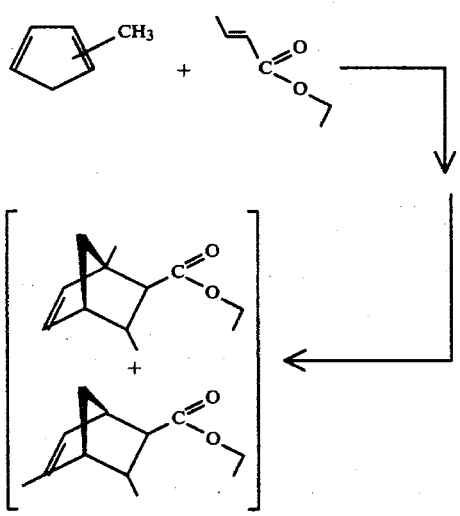

Into a 5 liter reaction vessel equipped with stirrer, thermometer, condenser, addition funnel, nitrogen purge and cooling bath are added 1000 ml toluene; 600 grams ethyl crotonate; and 50 grams of a 25% solution of ethyl aluminum dichloride in anhydrous toluene. The resulting mixture is cooled to 20°-25° C. and over a period of 3 hours while maintaining the temperature of the reaction at 20°-23° C., 378 grams of methyl cyclopentadiene mixture containing compounds having the structures:

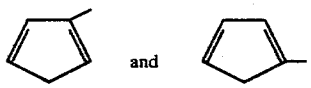

are added.

The reaction mass is then poured into one liter of a 10% aqueous hydrochloric acid solution. The reaction mass now exists in two phases; an aqueous phase and an organic phase. The aqueous phase is removed from the organic phase and the aqueous phase is extract with one 500 ml volume of toluene. The toluene and organic phases are combined and washed as follows:

A. One 1 liter portion of water;
B. One 1 liter portion of saturated sodium bicarbonate solution; and
C. One 1 liter portion of water.

The solvent is stripped off via vacuum. The resulting material is then distilled using a 12 inch Goodloe column yielding the following fractions:

| Fraction No. | Vapor Temp. (°C.) | Liquid Temp. (°C.) | mm/Hg. Pressure | Reflux Ratio | Weight of Fraction (g.) |
|---|---|---|---|---|---|
| 1 | 32 | 53 | 2.0 | 9:1 | 43.8 |
| 2 | 30 | 62 | 1.0 | 9:1 | 43.0 |
| 3 | 38 | 73 | 1.8 | 9:1 | 38.3 |
| 4 | 40 | 73 | .86 | 9:1 | 37.5 |
| 5 | 44 | 74 | .86 | 9:1 | 44.5 |
| 6 | 44 | 76 | .86 | 9:1 | 37.0 |
| 7 | 44 | 82 | .86 | 9:1 | 52.7 |
| 8 | 44 | 90 | .86 | 9:1 | 43.6 |
| 9 | 44 | 102 | .85 | 9:1 | 48.7 |
| 10 | 55 | 130 | .85 | 9:1 | 16.2 |
| 11 | 65 | 220 | 2.5 | 9:1 | 48.8 |

NMR, IR and mass spectral analysis yields the information that the reaction product contains compounds having the structures:

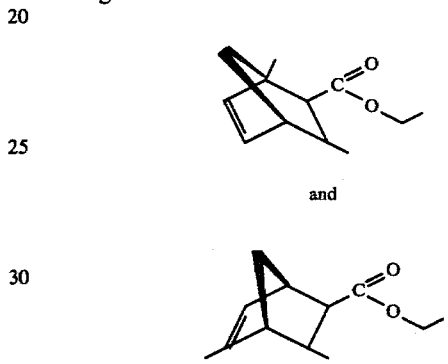

FIG. 9 sets forth the GLC profile prior to distillation of the resulting reaction product.

FIG. 10A sets forth the NMR spectrum for fraction 10 of the foregoing distillation containing only the product having the structure:

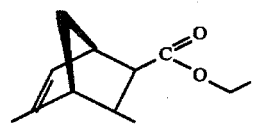

FIG. 10B is the NMR spectrum for the compound contained in fraction 6 of the foregoing distillation, having the structure:

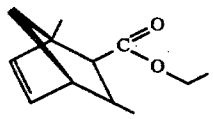

FIG. 11A is the infrared spectrum for the compound of fraction 10 of the foregoing distillation having the structure:

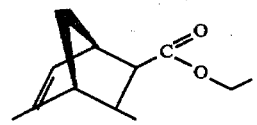

FIG. 11B is the infrared spectrum for the compound contained in fraction 6 of the foregoing distillation, having the structure:

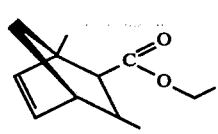

FIG. 12 is the mass spectrum for the mixture of compounds produced by the foregoing reaction having the structures:

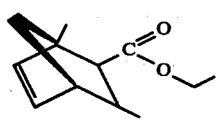

and

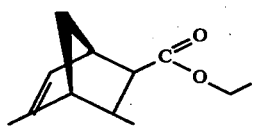

Bulked fractions 5-11 containing the compounds having the structures:

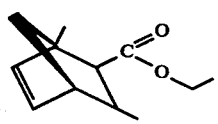

and

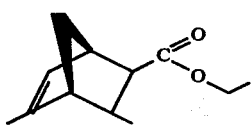

from a fragrance standpoint has a sweet, spicy, herbal, woody, eucalyptol-like aroma with distinct calamnus undertones.

Bulked fractions 5-11 from a food flavor standpoint has a sweet, fruity, berry-like, spicy, black pepper-like, herbaceous and clove-like aroma and taste profile at 10 ppm causing said bulked fractions to be useful in blueberry flavored tobacco (cloves) flavor and raspberry flavor.

Bulked fractions 5-11 from a tobacco flavor standpoint has a sweet, fruity, berry, spicy, cinnamon bark-like and clove-like aroma and taste profile both prior to and on smoking in the mainstream and in the sidestream of smoking tobacco articles such as cigarettes and cigars.

EXAMPLE IV

PREPARATION OF ETHYL ESTERS OF 1- and 5-METHYL-5-NORBORNENE-2-CARBOXYLIC ACIDS (CATALYTIC DIELS-ALDER REACTION)

Reaction:

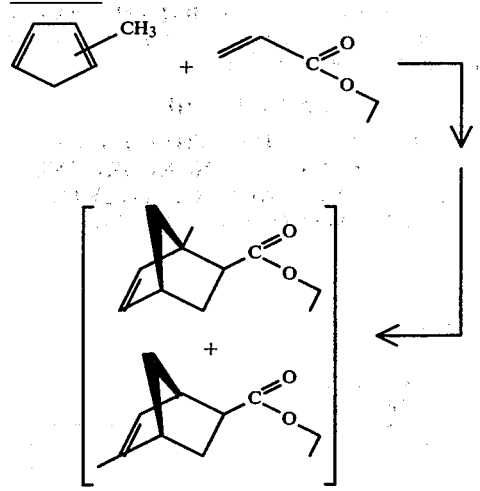

-continued

Into a three liter flask equipped with thermometer, stirrer, condenser, addition funnel, cooling bath and nitrogen purge are placed one gram of hydroquinone, 1000 ml toluene and 50 grams of 25% ethyl aluminum dichloride dissolved in anhydrous toluene. The reaction mass is cooled to about 10° C. and, over a period of 30 minutes, 600 grams of ethyl acrylate is added to the resulting mixture. During the addition the temperature of the mixture is maintained at between 10° C. and 14° C.

Over a period of three hours while maintaining the reaction temperature at 20°-23° C., 389 grams of a mixture of 1-methyl-1,3-cyclopentadiene and 2-methyl-1,3-cyclopentadiene is added to the reaction mixture. At the end of the three hour period GLC analysis indicates the reaction to be complete.

The resulting reaction mass is poured into one liter of 10% aqueous hydrochloric acid. The reaction mass now exists in two phases; an organic phase and an aqueous phase. The aqueous phase is separated from the organic phase and the organic phase is washed as follows:

A. One 1 liter portion of water;
B. One 1 liter portion of saturated sodium bicarbonate solution;
C. One 1 liter portion of water;
D. One 1 liter portion of water.

The pH of the resulting washing is about six.

The resulting organic layers are combined and the toluene is stripped off under vacuum. Calcium carbonate and primol ® is added to the reaction mass and the reaction mass is distilled yielding the following fractions on a 12 inch Goodloe column:

| Fraction No. | Vapor Temp. (°C.) | Liquid Temp. (°C.) | mm/Hg. Pressure | Reflux Ratio | Weight of Fraction (g.) |
|---|---|---|---|---|---|
| 1 | 48/48 | 63/65 | 3.0/3.0 | 9:1 | 23.8 |
| 2 | 50 | 64 | 3.0 | 9:1 | 19.3 |
| 3 | 50 | 64 | 2.8 | 9:1 | 20.5 |
| 4 | 53 | 64 | 2.6 | 9:1 | 19.1 |
| 5 | 54 | 64 | 2.6 | 9:1 | 20.2 |
| 6 | 55 | 65 | 2.8 | 9:1 | 19.9 |
| 7 | 56 | 66 | 2.7 | 9:1 | 25.2 |
| 8 | 54 | 66 | 2.5 | 9:1 | 21.7 |
| 9 | 54 | 66 | 2.5 | 9:1 | 48.6 |
| 10 | 54 | 66 | 2.5 | 9:1 | 55.8 |

| Fraction No. | Vapor Temp. (°C.) | Liquid Temp. (°C.) | mm/Hg. Pressure | Reflux Ratio | Weight of Fraction (g.) |
|---|---|---|---|---|---|
| 11 | 54 | 67 | 2.5 | 9:1 | 48.7 |
| 12 | 57 | 77 | 2.5 | 9:1 | 59.7 |
| 13 | 57 | 77 | 2.5 | 9:1 | 47.2 |
| 14 | 57 | 87 | 2.5 | 9:1 | 58.0 |
| 15 | 55/58 | 87/108 | 2.5/2.5 | 4:1 | 33.0 |
| 16 | 45 | 110 | 3.0 | 4:1 | 6.6 |

Fractions 7-12 are bulked and NMR, IR and mass spectral analysis yield the information that these fractions consist essentially of a mixture of compounds having the structures:

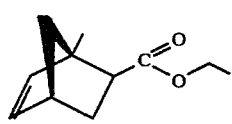

and

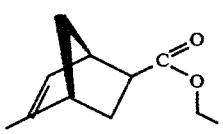

FIG. 13 is the GLC profile of the crude reaction product washed, but before distilling. (Conditions: Carbowax column programmed at 80°-122° C. at 8° C. per minute).

FIG. 14 is the GLC profile of fractions 7-12 from the foregoing distillation, bulked.

FIG. 15A is the NMR spectrum for the compound having the structure:

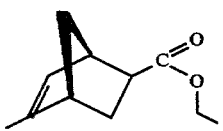

FIG. 15B is the NMR spectrum for the compound having the structure:

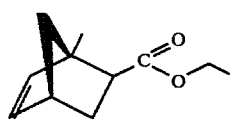

FIG. 16A is the infrared spectrum for the compound having the structure:

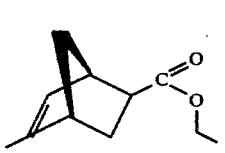

FIG. 16B is the infrared spectrum for the compound having the structure:

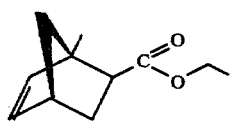

FIG. 17 is the mass spectrum for the mixture of compounds having the structures:

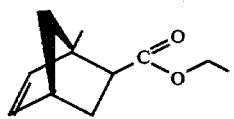

and

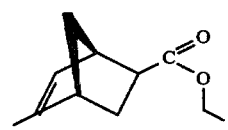

The mixture of compounds having the structures:

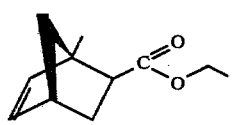

and

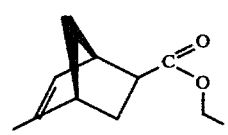

from a fragrance standpoint has a sweet, fruity (banana-like) and creamy aroma profile with minty nuances intense on dryout.

From a food flavor standpoint, the resulting mixture has a sweet, fruity, red berry, raspberry and seedy aroma and taste and in addition a strawberry taste at 0.02 ppm. Thus, this material is useful in red berry, cherry, raspberry and strawberry flavored foodstuffs.

The resulting mixture has a fruity, banana, green and strawberry-like aroma and taste both prior to and on smoking smoking tobacco articles in both the mainstream and the sidestream.

EXAMPLE V

PREPARATION OF THE ETHYL ESTERS OF 1-AND 5-METHYL NORBORNANE-2-CARBOXYLIC ACIDS

Reaction:

Reaction:

-continued

Reaction:

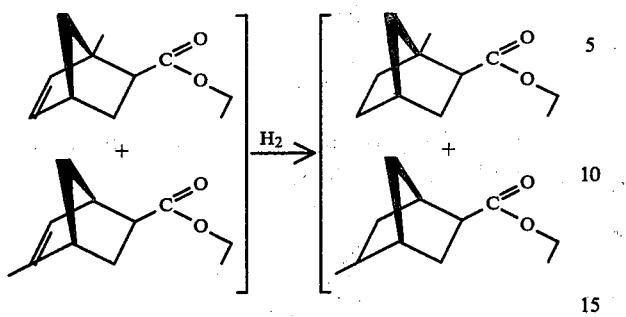

Into a 500 ml pressure bottle attached to a Parr shaker is charged 200 grams (1.11 moles) of the reaction mixture (bulked fractions 7–12) produced according to Example IV consisting essentially of compounds having the structures:

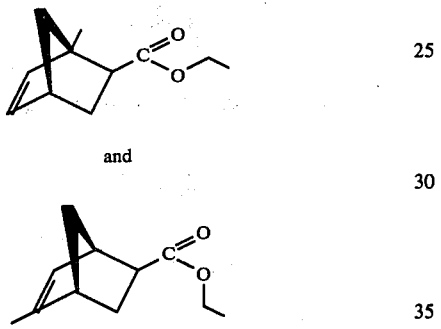

5 grams of Raney Nickel and 125 ml of isopropyl alcohol. The Parr shaker apparatus is purged six times with hydrogen and the 500 ml pressure bottle with contents is pressurized to 50 psig. The bottle is closed and shaking is begun and continued until the hydrogen uptake ceases. This period of time takes 4.25 hours. The 500 ml pressure bottle is recharged when necessary. At the end of the reaction the 500 ml pressure bottle is opened and the reaction mass is filtered and the solvent stripped in vacuum. The resulting residue is distilled on a 1" Goodloe-silver column and yields the following fractions:

| Fraction No. | Vapor Temp. (°C.) | Liquid Temp. (°C.) | mm/Hg. Pressure | Reflux Ratio | Weight of Fraction (g.) |
|---|---|---|---|---|---|
| 1 | 54/42 | 77/77 | 2.8/.8 | 9:1 | 18.5 |
| 2 | 42 | 77 | 0.75 | 9:1 | 22.2 |
| 3 | 42 | 78 | 0.70 | 9:1 | 22.0 |
| 4 | 46 | 85 | 0.70 | 9:1 | 23.0 |
| 5 | 50 | 87 | 1.4 | 9:1 | 18.0 |
| 6 | 50 | 90 | 0.8 | 9:1 | 21.0 |
| 7 | 51 | 111 | 0.7 | 9:1 | 19.0 |
| 8 | 45 | 170 | 0.75 | 9:1 | 23.0 |
| 9 | 39 | 214 | 0.76 | 9:1 | 3.0 |

NMR, IR and mass spectral analysis on fractions 1 and 9 yield the information that the resulting mixture contains and consists essentially of the compounds having the structures:

FIG. 18 is the GLC profile for the resulting reaction mixture.

FIG. 19A is the NMR spectrum for fraction 9 of the foregoing distillation containing and consisting of the compound having the structure:

FIG. 19B is the NMR spectrum for fraction 1 of the foregoing distillation consisting of the compound having the structure:

FIG. 20A is the infrared spectrum for fraction 9 of the foregoing distillation consisting of the compound having the structure:

FIG. 20B is the infrared spectrum for fraction 1 of the foregoing distillation consisting of the compound having the structure:

FIG. 21 is the mass spectrum for the reaction product produced according to this example containing the mixture of compounds having the structures:

and

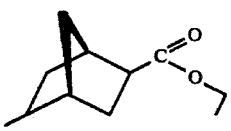

From a fragrance standpoint bulked fractions 6–8 have a fruity, banana, and creamy aroma profile.

From a food flavor standpoint, bulked fractions 6–8 have a sweet, fruity, raspberry, vermouth-like and blueberry aroma profile with a fruity, raspberry and blueberry taste profile at 0.01 ppm and at 1 ppm causing this mixture to be useful for vermouth, blueberry, raspberry mouthwash and toothpaste flavors.

From a tobacco flavor standpoint, bulked fractions 6–8 has prior to and on smoking in the mainstream and in the sidestream a sweet, fruity, "juicyfruit", woody, piney and blueberry aroma and taste profile.

EXAMPLE VI

PREPARATION OF 1- AND 5-METHYL-5-NORBORNENE-2-CARBOXYLIC ACID n-BUTYL ESTERS (CATALYTIC DIELS-ALDER REACTION)

Reaction:

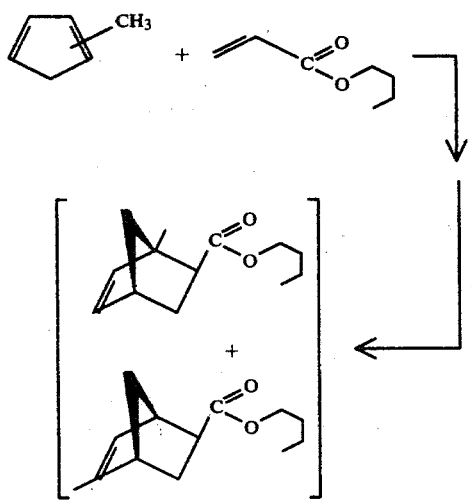

Into a 3 liter reaction flask equipped with stirrer, thermometer, reflux condenser, dropping funnel and cooling bath is placed 700 ml toluene and 60 grams of ethyl aluminum dichloride. While maintaining the temperature of the mixture at 20°–25° C., via the dropping funnel is added 300 grams of n-butyl acrylate over a period of 20 minutes.

While keeping temperature at 20°–25° C. over a 40 minute period, 380 grams of a 50% solution of 1-methyl-1,3-cyclopentadiene and 2-methyl-1,3-cyclopentadiene is added to the reaction mass.

After about 2 hours an additional 30 grams of ethyl aluminum dichloride is added and the reaction mass is stirred for another 1.5 hours while maintaining the temperature thereof at 20°–25° C.

Reaction mass is then added to 1 liter of 10% hydrochloric acid. The reaction mass now exists in two phases; an organic phase and an aqueous phase. The organic phase is removed and washed as follows:

A. One 1 liter portion of water;
B. One 1 liter portion of saturated sodium carbonate;
C. One 1 liter portion of water.

The solvent is then removed by vacuum distillation and the resulting product is distilled on a 12" Goodloe column yielding the following fractions:

| Fraction No. | Vapor Temp. (°C.) | Liquid Temp. (°C.) | mm/Hg. Pressure | Reflux Ratio | Weight of Fraction (g.) |
|---|---|---|---|---|---|
| 1 | 70/70 | 107/113 | 1.0/1.0 | 9:1/4:1 | 16.0 |
| 2 | 70 | 113 | 1.0 | 4:1 | 18.0 |
| 3 | 69 | 112 | 1.0 | 4:1 | 14.2 |
| 4 | 69 | 113 | 1.0 | 9:1 | 22.6 |
| 5 | 71 | 116 | 1.0 | 9:1 | 23.4 |
| 6 | 71 | 116 | 1.0 | 9:1 | 21.4 |
| 7 | 74 | 116 | 1.0 | 9:1 | 8.7 |
| 8 | 72 | 121 | 1.2 | 9:1 | 17.4 |
| 9 | 73 | 122 | 1.5 | 9:1 | 18.5 |
| 10 | 74 | 123 | 1.2 | 9:1 | 18.6 |
| 11 | 74 | 123 | 1.2 | 9:1 | 22.6 |
| 12 | 82 | 130 | 1.3 | 9:1 | 18.1 |
| 13 | 82 | 133 | 1.3 | 9:1 | 21.2 |
| 14 | 82 | 138 | 1.3 | 9:1 | 22.5 |
| 15 | 82 | 140 | 1.4 | 9:1 | 20.3 |
| 16 | 82 | 148 | 1.4 | 9:1 | 25.6 |
| 17 | 82 | 182 | 1.2 | 9:1 | 23.7 |
| 18 | 84 | 190 | 1.2 | 9:1 | 6.0 |

NMR, IR and mass spectral analysis yielding the information that the resulting product is a mixture of compounds having the structures:

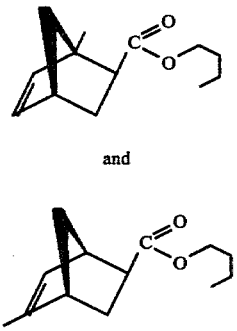

and

FIG. 22 sets forth the GLC profile for the reaction product.

FIG. 23A sets forth the NMR spectrum for fraction 14 for the foregoing fractional distillation and this fraction consists of compound having the structure:

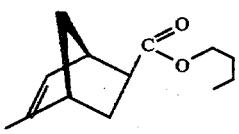

FIG. 23B sets forth the NMR spectrum for fraction 4 of the foregoing distillation consisting of the compound having the structure;

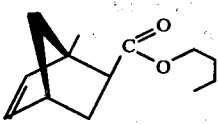

FIG. 24A sets forth the infrared spectrum for fraction 14 of the foregoing distillation consisting of the compound having the structure:

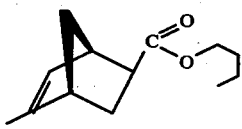

FIG. 24B sets forth the infrared spectrum for fraction 4 of the foregoing distillation consisting of the compound having the structure:

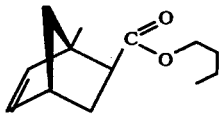

FIG. 25 sets forth the mass spectrum for the reaction product containing the compounds having the structures:

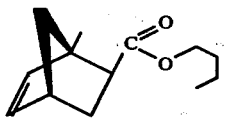

and

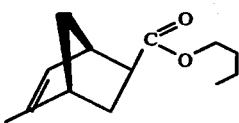

From a fragrance standpoint bulked fractions 2–18 have a balsamic and rum/butterscotch aroma profile.

From a food flavor standpoint, bulked fractions 5–14 have a fruity, strawberry, blueberry, balsamic aroma profile with a blueberry, balsamic and bitter flavor profile at 2 ppm.

From a tobacco flavor standpoint, bulked fractions 5–14 have an earthy and mushroom aroma and taste both prior to and on smoking in the mainstream and in the sidestream.

EXAMPLE VII

PREPARATION OF ETHYL ESTERS OF 1,2- AND 2,5-DIMETHYL-5-NORBORNENE-2-CARBOXYLIC ACIDS (CATALYTIC DIELS-ALDER REACTION)

Reaction:

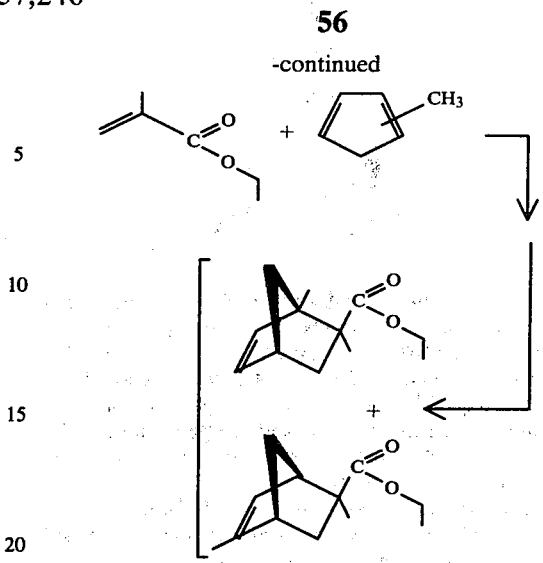

Into a 5 liter flask equipped with condenser, thermometer, addition funnel, nitrogen purge and cooling bath are placed 1000 ml toluene, 50 grams of ethyl aluminum dichloride and 680 grams of ethyl methacrylate. The resulting mixture is cooled to 20°–25° C. and over a period of 3 hours while maintaining the temperature at 23°–24° C. 400 grams of a mixture of 1-methyl-1,3-cyclopentadiene and 2-methyl-1,3-cyclopentadiene is added to the reaction mass.

The reaction mass is then poured into 1 liter of 10% aqueous hydrochloric acid. The reaction mass now exists in two phases; an aqueous phase and an organic phase. The aqueous phase is extracted with one 500 ml portion of toluene and the toluene extract is combined with the organic layer. The resulting organic phase is washed as follows:

A. One 1 liter portion of water;
B. One 1 liter portion of saturated sodium bicarbonate;
C. One 1 liter portion of water.

The resulting product is then stripped of solvent under vacuum. Primol ® and Ionox ® are then added to the reaction mass. The reaction mass is then distilled on an 18″ Goodloe column yielding the following fractions:

| Fraction No. | Vapor Temp. (°C.) | Liquid Temp. (°C.) | mm/Hg. Pressure | Reflux Ratio | Weight of Fraction (g.) |
|---|---|---|---|---|---|
| 1 | 55/56 | 84/85 | 5.5/5.5 | 9:1 | 8.3 |
| 2 | 60 | 83 | 4.0 | 9:1 | 41.9 |
| 3 | 66 | 84 | 4.0 | 9:1 | 40.0 |
| 4 | 67 | 85 | 4.0 | 9:1 | 44.4 |
| 5 | 67 | 88 | 4.0 | 9:1 | 40.8 |
| 6 | 67 | 93 | 4.0 | 9:1 | 40.7 |
| 7 | 68 | 101 | 4.0 | 9:1 | 39.1 |
| 8 | 69 | 110 | 4.0 | 9:1 | 51.3 |
| 9 | 70 | 125 | 4.0 | 9:1 | 39.4 |
| 10 | 70 | 157 | 4.0 | 9:1 | 16.0 |
| 11 | 72/75 | 170/220 | 4.0/4.0 | 9:1 | 10.0 |

NMR, IR and mass spectral analysis yield the information that the resulting product contains two compounds having the structures:

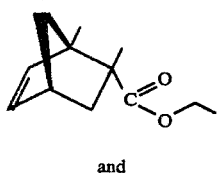

and

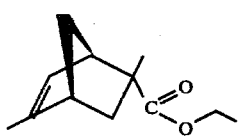

These materials are not separable via ordinary commercial physical separation procedures or commercial unit operations.

FIG. 26 sets forth the GLC profile for the resulting mixture containing the compounds having the structures:

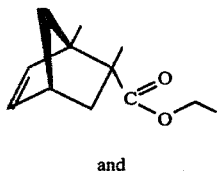

and

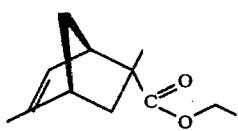

FIG. 27 sets forth the NMR spectrum for the mixture of compounds having the structures:

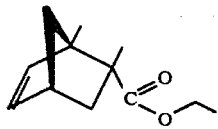

and

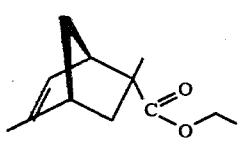

FIG. 28 sets forth the infrared spectrum for the compounds having the structures:

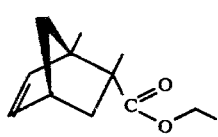

and

-continued

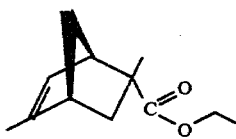

in admixture.

FIG. 29 sets forth the mass spectrum for the reaction product as produced above containing and consisting of the structures:

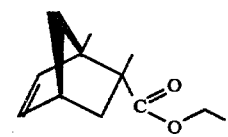

and

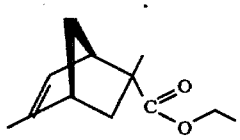

Bulked fractions 4–10 from a fragrance standpoint has a green, minty, spicy aroma with medicinal nuances and a pepacuana bark extract type undertone.

From a food flavor standpoint the resulting mixture containing the compounds having the structures:

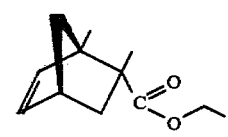

and

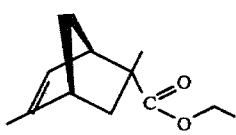

has a fruity, raspberry and seedy aroma and flavor characteristic with additional bitter flavor nuance at 0.2 ppm.

From a tobacco flavor standpoint, the resulting mixture has a sweet, green, herbaceous, dill and fruity aroma and taste both prior to and on smoking in smoking tobacco in the main stream and in the side stream.

EXAMPLE VII-A

PREPARATION OF 1,3- AND 3,5-DIMETHYL NORBORNANE CARBOXYLIC ACID ESTERS

Reaction:

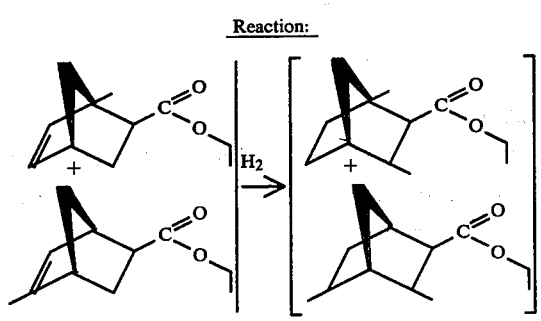

Into a 500 ml pressure bottle equipped with Parr shaker is placed 200 grams of the reaction product of Example III containing the compound having the structures:

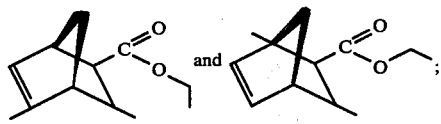

100 ml isopropyl alcohol and 5 grams of Raney nickel. The 500 ml pressure bottle is then closed and placed under hydrogen pressure. The Parr shaker is shaken under while maintaining the hydrogen pressure at 50 psig for a period of 5.5 hours at a temperature of 20°–30° C. The Parr shaker and pressure bottle apparatus is then opened and the reaction mass is filtered and the solvent is removed from the reaaction mass. The resulting reaction product is then distilled yielding the following fractions:

| Fraction No. | Vapor Temp. (°C.) | Liquid Temp. (°C.) | mm. Hg. Pressure | Reflux Ratio | Weight of Fraction (g.) |
|---|---|---|---|---|---|
| 1 | 53/55 | 70/73 | 1.2/1.2 | 9:1/9:1 | 5.7 |
| 2 | 55 | 73 | 1.2 | 3:1 | 18.5 |
| 3 | 54 | 73 | 1.2 | 3:1 | 15.9 |
| 4 | 57 | 74 | 1.2 | 3:1 | 13.0 |
| 5 | 58 | 74 | 1.2 | 3:1 | 17.3 |
| 6 | 62 | 75 | 1.2 | 3:1 | 14.6 |
| 7 | 64 | 75 | 1.5 | 3:1 | 25.3 |
| 8 | 60 | 80 | 1.4 | 3:1 | 17.6 |
| 9 | 58 | 78 | 1.2 | 3:1 | 24.9 |
| 10 | 59 | 80 | 1.2 | 3:1 | 18.5 |
| 11 | 59 | 82 | 1.2 | 3:1 | |

Fractions 3–8 are bulked and NMR, IR and mass spectral analyses yield the information that bulked fractions 3–8 consist of the compounds having the structures:

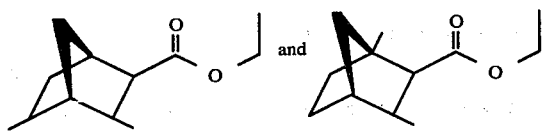

Fraction 1 of the foregoing distillation contains the pure compound having the structure:

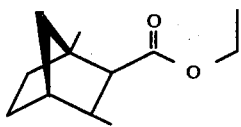

Peak 2 of the foregoing GLC analysis consists of the compound having the structure:

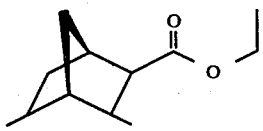

FIG. 31-A is the NMR spectrum for the compound having the structure:

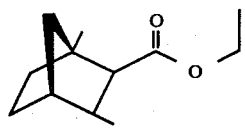

of fraction 1 of the foregoing distillation.

FIG. 31-B is the NMR spectrum for the compound having the structure:

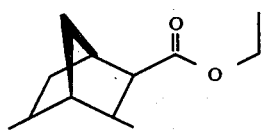

of peak 2 of the foregoing GLC profile.

FIG. 32-A is the infrared spectrum for fraction 1 of the foregoing distillation consisting of the compound having the structure:

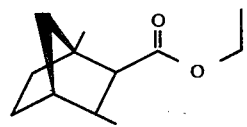

FIG. 32-B is the infrared spectrum for peak 2 of the foregoing GLC profile consisting of the compound having the structure:

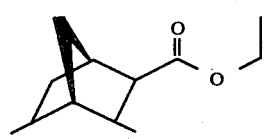

FIG. 33-A is the mass spectrum for fraction 1 of the foregoing distillation consisting of the compound having the structure:

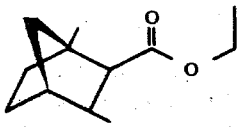

FIG. 33-B is the mass spectrum for peak 2 of the foregoing GLC profile consisting of the compound having the structure:

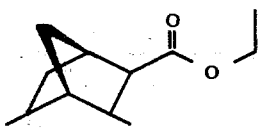

EXAMPLE VIII

The following spicy, floral and herbal type formulae are prepared:

| Ingredient | Parts by Weight | |
|---|---|---|
| | VIII (A) | VIII (B) |
| Geranium Bourbon | 20.0 | 20.0 |
| Rosemary Oil Spanish | 10.0 | 10.0 |
| Lavender Oil Barreme | 10.0 | 10.0 |
| Thyme Oil White | 10.0 | 10.0 |
| Amyl Cinnamic Aldehyde | 10.0 | 10.0 |
| Sauge Sclaree French | 5.0 | 5.0 |
| Sandalwood Oil | 5.0 | 5.0 |
| Galbanum Oil | 5.0 | 5.0 |
| Patchouli Oil Light | 5.0 | 5.0 |
| Cedarwood Oil Light | 15.0 | 15.0 |
| Product produced according to Example III, bulked fractions 5-11 containing and consisting of the compounds having the structures: | 5.0 | — |

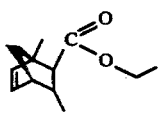

and

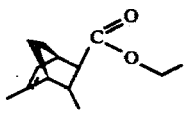

| | | |
|---|---|---|
| Product produced according to Example V containing bulked fractions 1-9 and consisting of the compounds having the structures: | — | 5.0 |

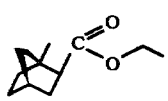

and

| Ingredient | Parts by Weight | |
|---|---|---|
| | VIII (A) | VIII (B) |

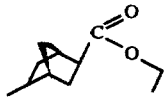

When the compositions of matter prepared according to Example III or Example V are incorporated into the formulae at 5.0% both compositions of matter add a pleasant fruity, tagette character to these spicy, herbal, floral type perfume formulations.

EXAMPLE IX

A jasmine formulae is produced containing the following ingredients:

| Ingredients | Parts by Weight |
|---|---|
| Isoeugenol | 2.0 |
| Benzyl Propionate | 10.0 |
| Benzyl Acetate | 13.0 |
| Benzyl Alcohol | 14.0 |
| Benzyl Benzoate | 9.0 |
| Linalool | 8.0 |
| Phytol | 30.0 |
| Methyl Oleate | 4.0 |
| Methyl Palmitate | 4.0 |
| Indole - 10% in Diethyl Phthalate | 1.0 |
| Composition produced according to Example IV containing bulked fractions 7-12 and containing the compounds having the structures: | 5.0 |

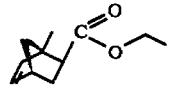

and

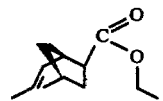

The material produced according to Example IV incorporated into the formula above at 5.0% gives rise to the pleasant fruityness aroma undertone of this jasmine formulation.

EXAMPLE X

The following sweet, floral formula is produced:

| Ingredients | Parts by Weight |
|---|---|
| Hexyl Cinnamic Aldehyde | 12.0 |
| Benzyl Propionate | 8.0 |
| Isoeugenol | 2.0 |
| Indole - 10% in Diethyl Phthalate | 1.0 |
| Linalool | 8.0 |
| Benzyl Acetate | 8.0 |
| Vetivert Oil - Bourbon | 2.0 |
| Gamma Methyl Ionone | 1.0 |
| Phenyl Ethyl Alcohol | 6.0 |
| Patchouli Oil Light | 1.0 |
| Lavandin Abrialis | 4.0 |
| Hydroxy Citronellal | 4.0 |
| Bergamot Oil M.P.F. | 6.0 |

| Ingredients | Parts by Weight |
|---|---|
| Benzyl Salicylate | 13.0 |
| Musk Ambrette | 8.0 |
| Coumarin | 6.0 |
| Composition of matter produced according to Ex. II consisting of bulked fractions 4-6 and consisting the compounds having the structures: | 10.0 |

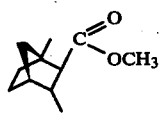

and

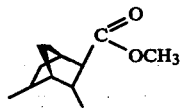

At the 10% level in the foregoing sweet, floral formulation the compounds having the structures:

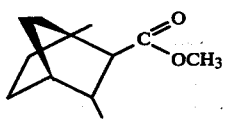

and

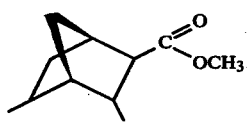

produced according to Example II contribute an intense and pleasant fruity, floralcy to this sweet, floral fragrance.

EXAMPLE XI

A stable lotion is prepared with the following formulations:

| Ingredients | Parts by Weight |
|---|---|
| poly(N,N-dimethyl-3,5-dimethylene piperidinium chloride) (Merquat 100, Merck & Co., U.S.A., average molecular weight 50,000-100,000,viscosity in 40% aqueous solution, 10,000 cps. | 1.0 |
| cocoamidopropyl dimethyl glycine (betaine) | 5.7 |
| myristyl dimethylamine oxide | 12.0 |
| stearic monoethanolamide opacifier | 2.0 |
| perfume as indicated in Table III (below) giving rise to the aroma profiles as indicated in Table III (below) | 0.5 |
| water, colour, salts, U.V. absorber | q.s. to 100 |

Two or three bottle capfuls of the above lotion held under the tap releasing the water into the bathtub yields a copiously foamed bubble bath with no visible precipitation flocculation, or "bathtub ring" even using hard water. Bathing in this bath is found to have a cleansing and pleasing emollient effect on the skin as described above.

When, after immersion in this bath, the body is soaped, rinsed and dried, an even better, more long-lasting emollient, moisturizing effect on the skin is observed. The foam or bubbles are substantially unaffected by the soaping step, and no precipitate, flocculate or "bathtub ring", or any bothersome film or coating on the bathtub surface is found.

The aroma produced is as is set forth in Table III below:

TABLE III

| Product | Aroma Profile |
|---|---|
| Product produced according to Example I, bulked fractions 4-7 consisting of compounds having the structures:<br/>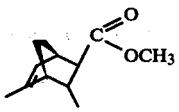<br/>and<br/>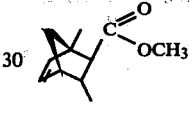 | A fruity, banana and creamy aroma with camphoraceous and minty undertones. |
| Product produced according to Example II, bulked fractions 4-6 consisting of the compounds having the structures:<br/>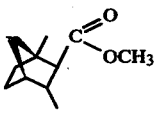<br/>and<br/>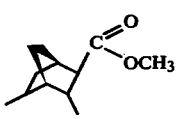 | A fruity, camphoraceous and herbaceous aroma. |
| Product produced according to Example III, bulked fractions 7 and 8 consisting of the compounds having the structures:<br/>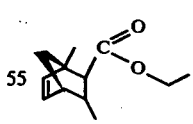<br/>and<br/>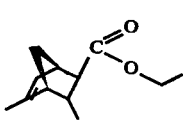 | A sweet, spicy, herbal woody and eucalyptol-like aroma with a distinct calamnus undertone |
| Product produced according to Example IV, bulked fractions 7-12 consisting of compounds having the structures: | A sweet, fruity (banana) creamy and minty aroma with the minty nuances increasing in intensity on dryout. |

TABLE III-continued

| Product | Aroma Profile |
|---|---|
| 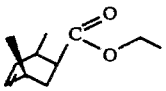 and  Product produced according to Example V, bulked fractions 6–8 consisting of the compounds having the structures: | A fruity, banana and creamy aroma profile. |
| 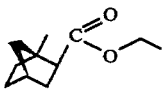 and  Product produced according to Example VI, bulked fractions 5–14 containing and consisting of the compounds having the structures: | A rum/butterscoth and balsamic aroma. |
| 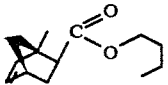 and 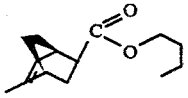 Product produced according to Example VII, bulked fractions 6–9 consisting of the compounds having the structures: | A green, minty, borneol-like, spicy, somewhat medicinal aroma reminiscent of pepacuana bark extract with strong pepacuana bark-like undertones. |
| 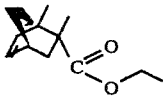 and 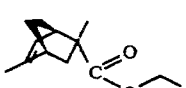 Fragrance formulation of Example VIII(A) | A spicy, floral, herbal aroma with pleasant fruity tagette characteristics. |
| Fragrance formulation of Example VIII(B) | A spicy, floral, herbal aroma with pleasant fruity tagette characteristics. |
| Fragrance formulation of Example IX | A jasmine aroma with a pleasant fruityness. |
| Fragrance formulation of Example X | A sweet, floral aroma with excellent fruity floralcy undertones. |

EXAMPLE XII

The following formulation is prepared with results in properties and use similar to those described in Example XI.

| Ingredients | Parts by Weight |
|---|---|
| "Merquat 100" | 1.0 |
| cocoamidopropyl dimethyl glycine | 8.0 |
| myristyl dimethyl amine oxide | 16.0 |
| Perfume ingredient as set forth in Table IV (below) giving rise to the aroma profiles as set forth in Table IV (below) | 0.8 |
| Water | q.s. to 100 |

The composition is a clear liquid. Its viscosity may be increased by addition of a lauric or myristic diethanolamide or a soluble polyethylene glycol ester such as polyethylene glycol 6000. In addition, this composition may be rendered opaque by addition of stearic monoethanolamide stearate, polyethylene glycol 600 monostearate or a glycol amido stearate such as "Cerasynt 1P".

TABLE IV

| Product | Aroma Profile |
|---|---|
| Product produced according to Example I, bulked fractions 4–7 consisting of compounds having the structures: 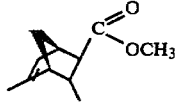 and 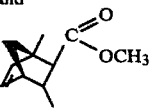 | A fruity, banana and creamy aroma with camphoraceous and minty undertones. |
| Product produced according to Example II, bulked fractions 4–6 consisting of the compounds having the structures: 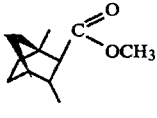 and 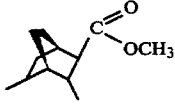 | A fruity, camphoraceous and herbaceous aroma. |
| Product produced according to Example III, bulked fractions 7 and 8 consisting of the compounds having the structures: 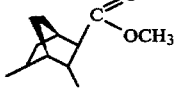 | A sweet, spicy, herbal woody and eucalyptol-like aroma with a distinct calamnus undertone. |

TABLE IV-continued

| Product | Aroma Profile |
|---|---|
| 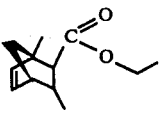 and 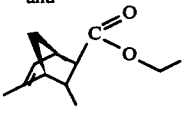<br>Product produced according to Example IV, bulked fractions 7–12 consisting of compounds having the structures: | A sweet, fruity (banana) creamy and minty aroma with the minty nuances increasing in intensity on dryout. |
| 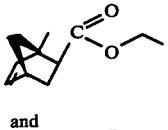 and 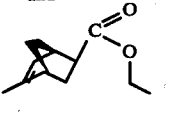<br>Product produced according to Example V, bulked fractions 6–8 consisting of the compounds having the structures: | A fruity, banana and creamy aroma profile. |
| 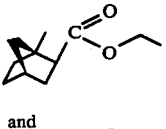 and 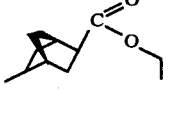<br>Product produced according to Example VI, bulked fractions 5–14 containing and consisting of the compounds having the structures: | A rum/butterscotch and balsamic aroma. |
| 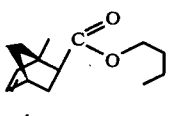 and 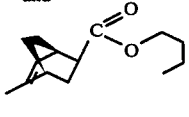<br>Product produced according to Example VII, bulked fractions 6–9 consisting of the compounds having the structures: | A green, minty, borneol-like, spicy, somewhat medicinal aroama reminiscent of pepacuana bark extract with strong pepacuana bark-like undertones. |
| 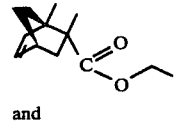 and 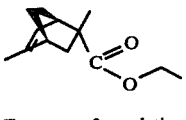 | |
| Fragrance formulation of Example VIII(A) | A spicy, floral, herbal aroma with pleasant fruity tagette characteristics. |
| Fragrance formulation of Example VIII(B) | A spicy, floral, herbal aroma with pleasant fruity tagette characteristics. |
| Fragrance formulation of Example IX | A jasmine aroma with a pleasant fruityness. |
| Fragrance formulation of Example X | A sweet, floral aroma with excellent fruity floralcy undertones. |

EXAMPLE XIII

The following shampoo is prepared containing the following ingredients:

| Ingredients | Parts by Weight |
|---|---|
| Tridecyloxy polyethoxy ethanol of ten ethoxy groups | 17.3 |
| Polyoxyethylene (20) sorbitan monolaurate | 7.5 |
| Myristyl dimethylamine oxide (30% active) | 25.0 |
| $C_{10}$—$C_{20}$ fatty acyl monoethanolamide (cocomonoethanolamide) | 2.5 |
| Polyacrylamide of molecular weight of about 1,500,000 | 0.2 |
| Hydrogen peroxide (30% aqueous solution) | 0.5 |
| Perfume ingredient as indicated at Table V (below) giving rise to the aroma profiles as indicated in Table V (below) | 1.0 |
| Deionized water (3 micromhos/cm conductivity) | 46.0 |

A shampoo of the above composition is made in the following matter. First, the tridecyloxy polyethoxy ethanol is added to a clean mixing tank, with the agitator on, and the amine oxide, polyoxyethylene sorbitan monolaurate and cocomonoethanolamine are added sequentially, with continued agitation. The mix is then heated to 68° C., until the cocomonoethanolamide is melted and/or dissolved. The hydrogen peroxide solution is then admixed with the mentioned nonionics and mixing is continued for about half an hour, in which the peroxide destroys any free amines or other harmful impurities that may be present. The mix is then cooled to 38° C.

In a separate mixer the polyacrylamide is gradually added to the formula weight of deionized water, with the mixer on. Addition is effected carefully and slowly (the polyacrylamide is sprinkled in) to avoid the production of "fish eyes" in the mix. After dissolving of the polyacrylamide the solution thereof is added to the first mixing tank with agitation and is blended with the nonionics, such mixings being at room temperature. Subsequently the perfume as indicated in Table V (below) giving rise to the aroma profile as set forth in Table V (below) is admixed with the balance of the composition and mixing is continued for another half hour.

TABLE V

| Product | Aroma Profile |
|---|---|
| Product produced according to Example I, bulked fractions 4–7 consisting of compounds having the structures: 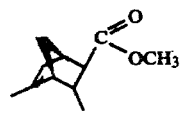 and 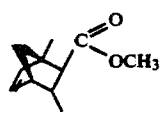 | A fruity, banana and creamy aroma with camphoraceous and minty undertones. |
| Product produced according to Example II, bulked fractions 4–6 consisting of the compounds having the structures: 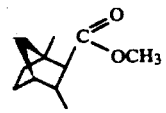 and 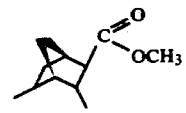 | A fruity, camphoraceous and herbaceous aroma. |
| Product produced according to Example III, bulked fractions 7 and 8 consisting of the compounds having the structures: 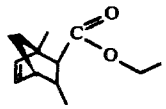 and 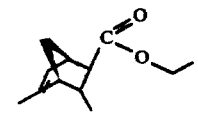 | A sweet, spicy, herbal woody and eucalyptol-like aroma with a distinct calamnus undertone. |
| Product produced according to Example IV, bulked fractions 7–12 consisting of compounds having the structures: 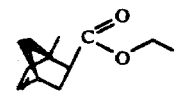 and | A sweet, fruity (banana) creamy and minty aroma with the minty nuances increasing in intensity on dryout. |

TABLE V-continued

| Product | Aroma Profile |
|---|---|
| Product produced according to Example V, bulked fractions 6–8 consisting of the compounds having the structures: and | A fruity, banana and creamy aroma profile. |
| Product produced according to Example VI, bulked fractions 5–14 containing and consisting of the compounds having the structures: and | A rum/butterscotch and balsamic aroma. |
| Product produced according to Example VII, bulked fractions 6–9 consisting of the compounds having the structures: and | A green, minty, borneol-like, spicy, somewhat medicinal aroma reminiscent of pepacuana bark extract with strong pepacuana bark-like undertones |
| Fragrance formulation of Example VIII(A) | A spicy, floral, herbal aroma with pleasant fruity tagette characteristics. |
| Fragrance formulation of Example VIII(B) | A spicy, floral, herbal aroma with pleasant fruity tagette characteristics. |
| Fragrance formulation of Example IX | A jasmine aroma with a pleasant fruityness. |
| Fragrance formulation of Example X | A sweet, floral aroma with excellent fruity floralcy undertones. |

The product made is an excellent shampoo of satisfactory viscosity and aroma, foaming power, foam stability, low conductivity and good shampooing effects. The viscosity is about 1,000 centipoises at 20° C. and the conductivity, using the Hach Conductivity Meter, is 750 micromhos/cm. The foaming power is 250 ml and the foam stability is 22 seconds, by the test method previously described. In comparison, a commercial shampoo based on triethanolamine lauryl sulphate detergent has a conductivity of about 22,000 micromhos/cm, a viscosity of about 1,500 centipoises, a foaming power of about 380 ml and a foam stability of 60 seconds.

In panel evaluations of the experimental shampoo compared to a different commercial product, in actual shampooing, the experimental formula was adjudged significantly better in being less drying, producing a softer feel for the wet hair, leaving the wet hair easier to comb, being less prone to accumulate static charges (less flyaway) and having a foam of better appearance and feel. Additionally, the experimental product was judged better in almost all hair effect properties, with the control only being about equal to it in curl retention. In properties other than those mentioned the experimental product was better in rinsability, the control was better in foam build-up rate and the foams were about equal in volume and stability.

In the shampooing described herein and in subsequent Examples the human hair is washed on the head by wetting the hair with warm tap water at about 42° C., applying 15 grams of shampoo to the hair, lathering it into the hair for a minute, rinsing with warm tap water for 30 seconds, re-lathering with 7 grams of shampoo for a minute and rinsing off for 30 seconds, after which the hair is towel dried and dried further with an automatic hair dryer.

EXAMPLE XIV

FABRIC FRESHENER COMPOSITION

A fabric freshener composition is prepared as follows:

| Ingredients | Parts by Weight |
|---|---|
| Sodium bicarbonate | 3 |
| "Kyro" EOB (Trade Mark)* | 1 |
| Perfume ingredient as set forth in Table VI below giving rise to an aroma as set forth in Table VI below | 1 |
| Water | 0.05 |

The composition of this Example is prepared by simply mixing the ingredients.

The above described composition is applied to a lightly soiled and wrinkled fabric as droplets (ca. 5.0 mm avg. size) using a trigger acton sprayer having a nozzle which is adjustable to provide composition droplets in the desire range. The composition is applied at a rate of about 1 gram of composition to about 10 grams of fabric.

The fabric is then placed in an automatic dryer and dried, with tumbling action, at a temperature of 60° C.-80° C. for a period of 15 minutes. The fabric is rendered free of wrinkles and static, and has a fresh appearance and pleasant odor profile as set forth in Table VI below. Suprisingly, the sodium bicarbonate is not visible on the refreshed fabric.

In the foregoing procedure, substantially the same results were obtained when sodium carbonate is substituted for the sodium bicarbonate.

TABLE VI

| Product | Aroma Profile |
|---|---|
| Product produced according to Example I, bulked fractions 4–7 consisting of compounds having the structures: [structure with C=O, OCH₃] and [structure with C=O, OCH₃] | A fruity, banana and creamy aroma with camphoraceous and minty undertones. |
| Product produced according to Example II, bulked fractions 4–6 consisting of the compounds having the structures: [structure with C=O, OCH₃] and [structure with C=O, OCH₃] | A fruity, camphoraceous and herbaceous aroma. |
| Product produced according to Example III, bulked fractions 7 and 8 consisting of the compounds having the structures: [structure with C=O, O-] and [structure with C=O, O-] | A sweet, spicy, herbal woody and eucalyptol-like aroma with a distinct calamnus undertone. |
| Product produced according to Example IV, bulked fractions 7–12 consisting of compounds having the structures: [structure with C=O, O-] and | A sweet, fruity (banana) creamy and minty aroma with the minty nuances increasing in intensity on dryout. |

TABLE VI-continued

| Product | Aroma Profile |
|---|---|
| Product produced according to Example V, bulked fractions 6–8 consisting of the compounds having the structures: [structure], and [structure] | A fruity, banana and creamy aroma profile. |
| Product produced according to Example VI, bulked fractions 5–14 containing and consisting of the compounds having the structures: [structure], and [structure] | A rum/butterscotch and balsamic aroma. |
| Product produced according to Example VII, bulked fractions 6–9 consisting of the compounds having the structures: [structure], and [structure] | A green, minty, borneol-like, spicy, somewhat medicinal aroma reminiscent of pepacuana bark extract with strong pepacuana bark-like undertones. |
| Fragrance formulation of Example VIII(A) | A spicy, floral, herbal aroma with pleasant fruity tagette characteristics. |
| Fragrance formulation of Example VIII(B) | A spicy, floral, herbal aroma with pleasant fruity tagette characteristics. |
| Fragrance formulation of Example IX | A jasmine aroma with a pleasant fruityness. |
| Fragrance formulation of Example X | A sweet, floral aroma with excellent fruity floralcy undertones. |

*A commercial nonionic surfactant comprising an average of eleven carbon atoms, ethoxylated to an average of 9 ethyleneoxy groups per molecule.

EXAMPLE XV

PERFUMED LIQUID DETERGENT

Concentrated liquid detergents (lysine salts of n-dodecyl benzene sulfonic acid as more specifically described in U.S. Pat. No. 3,948,818, issued on Apr. 6, 1976) with aromas as indicated in Table VII below are prepared containing 0.10%, 0.15%, 0.20%, 0.25%, 0.30%, 0.40%, 0.50% and 0.80% of the perfume ingredient as set forth in Table VII below. The detergents are prepared by adding a homogeneously mixing the appropriate quantity of perfume ingredient as set forth in Table VII below. The detergents all possess aromas as set forth in Table VII below with the intensity of each increasing with greater concentrations of the perfume ingredient as indicated in Table VII below.

TABLE VII

| Product | Aroma Profile |
|---|---|
| Product produced according to Example I, bulked fractions 4–7 consisting of compounds having the structures: [structure with $OCH_3$], and [structure with $OCH_3$] | A fruity, banana and creamy aroma with camphoraceous and minty undertones. |
| Product produced according to Example II, bulked fractions 4–6 consisting of the compounds having the structures: [structure with $OCH_3$], and [structure with $OCH_3$] | A fruity, camphoraceous and herbaceous aroma. |
| Product produced according to Example III, bulked fractions 7 and 8 consisting of the compounds having the structures: [structure], and [structure] | A sweet, spicy, herbal woody and eucalyptol-like aroma with a distinct calamnus undertone. |
| Product produced according to | A sweet, fruity (banana) |

TABLE VII-continued

| Product | Aroma Profile |
|---|---|
| Example IV, bulked fractions 7–12 consisting of compounds having the structures: 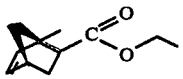 and 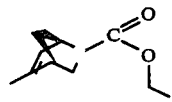 | creamy and minty aroma with the minty nuances increasing in intensity on dryout. |
| Product produced according to Example V, bulked fractions 6–8 consisting of the compounds having the structures: 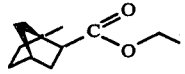 and 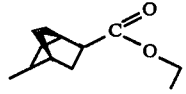 | A fruity, banana and creamy aroma profile. |
| Product produced according to Example VI, bulked fractions 5–14 containing and consisting of the compounds having the structures: 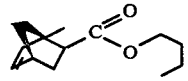 and 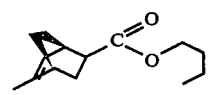 | A rum/butterscotch and balsamic aroma. |
| Product produced according to Example VII, bulked fractions 6–9 consisting of the compounds having the structures: 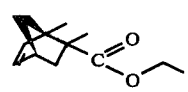 and  | A green, minty, borneol-like, spicy, somewhat medicinal aroma reminiscent of pepacuana bark extract with strong pepacuana bark-like undertones. |
| Fragrance formulation of Example VIII(A) | A spicy, floral, herbal aroma with pleasant fruity tagette characteristics. |
| Fragrance formulation of Example VIII(B) | A spicy, floral, herbal aroma with pleasant fruity tagette characteristics. |
| Fragrance formulation of Example IX | A jasmine aroma with a pleasant fruityness. |
| Fragrance formulation of Example X | A sweet, floral aroma with excellent fruity floralcy undertones. |

EXAMPLE XVI

PREPARATION OF A COLOGNE AND HANDKERCHIEF PERFUME

The perfume ingredient as set forth in Table VIII below is incorporated into colognes at concentrations of 2.0%, 2.5%, 3.0%, 3.5%, 4.0%, 5.0% and 6.0% in 75%, 80%, 85%, 90% and 95% aqueous ethanol solutions. Distinct and definite aromas as set forth in Table VIII below are imparted to the colognes. The perfume ingredients as indicated in Table VIII below are also added to handkerchief perfumes at concentrations of 15%, 20%, 25%, 30% and 35% (in 75%, 80%, 85%, 90% and 95% aqueous ethanol) and aroma profiles as set forth in Table VIII are imparted to the handkerchief perfume.

TABLE VIII

| Product | Aroma Profile |
|---|---|
| Product produced according to Example I, bulked fractions 4–7 consisting of compounds having the structures: 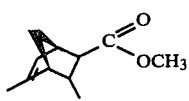 and 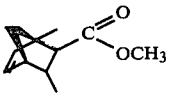 | A fruity, banana and creamy aroma with camphoraceous and minty undertones. |
| Product produced according to Example II, bulked fractions 4–6 consisting of the compounds having the structures: 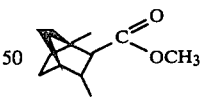 and 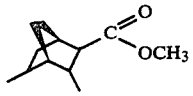 | A fruity, camphoraceous and herbaceous aroma. |
| Product produced according to Example III, bulked fractions 7 and 8 consisting of the compounds having the structures: 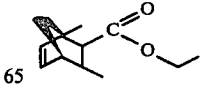 and | A sweet, spicy, herbal woody and eucalyptol-like aroma with a distinct calamnus undertone. |

TABLE VIII-continued

| Product | Aroma Profile |
|---|---|
| 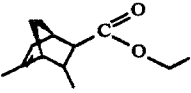 Product produced according to Example IV, bulked fractions 7-12 consisting of compounds having the structures: 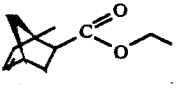 and 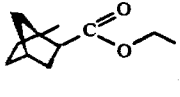 | A sweet, fruity (banana) creamy and minty aroma with the minty nuances increasing in intensity on dryout. |
| Product produced according to Example V, bulked fractions 6-8 consisting of the compounds having the structures: 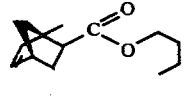 and 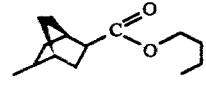 | A fruity, banana and creamy aroma profile. |
| Product produced according to Example VI, bulked fractions 5-14 containing and consisting of the compounds having the structures: 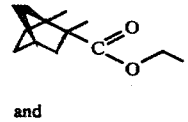 and 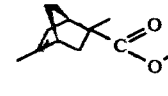 | A rum/butterscotch and balsamic aroma. |
| Product produced according to Example VII, bulked fractions 6-9 consisting of the compounds having the structures: 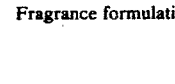 and 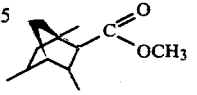 | A green, minty, borneol-like, spicy, somewhat medicinal aroma reminiscent of pepacuana bark extract with strong pepacuana bark-like undertones. |
| Fragrance formulation of Example VIII(A) | A spicy, floral, herbal aroma with pleasant fruity tagette characteristics. |
| Fragrance formulation of Example VIII(B) | A spicy, floral, herbal aroma with pleasant fruity tagette characteristics. |
| Fragrance formulation of Example IX | A jasmine aroma with a pleasant fruityness. |
| Fragrance formulation of Example X | A sweet, floral aroma with excellent fruity floralcy undertones. |

EXAMPLE XVII

BLUEBERRY FLAVOR FORMULATION

The following formulation is prepared:

| Ingredients | Parts by Weight |
|---|---|
| Heliotropin | 3.0 |
| Terpinenol-4 (10% in 95% aqueous food grade ethanol) | 0.2 |
| Benzaldehyde | 1.5 |
| Anisaldehyde | 0.2 |
| Phenyl acetaldehyde | 0.4 |
| Benzyl formate | 0.5 |
| Benzyl acetate | 2.0 |
| Cis-3-hexenyl benzoate (10% in 95% aqueous food grade ethanol) | 0.5 |
| Methyl hexanoate | 2.0 |
| Hexanal | 1.0 |
| Eucalyptol (1% in 95% aqueous food grade ethanol) | 0.5 |
| Eugenol | 0.2 |
| Acetaldehyde | 3.0 |
| Ethyl acetate | 21.0 |
| Ethyl butyrate | 26.0 |
| Propylene glycol | 38.0 |
| | 100.0 |

The above formulation is split into 5 portions. To the first four portions are added at the rate of 1%, the norbornane derivatives of Table IX. To the fifth portion nothing is added. All five formulations with and without said norbornyl derivatives are combined with water at the rate of 100 ppm. The flavor of the first four portions each including a norbornyl derivative prepared according to the preceeding examples as indicated in Table IX below have fruity, blueberry characteristics with several other nuances as indicated in Table IX below and are all closely similar to the flavor of wild blueberries. It is therefore preferred to use the formulations containing the norbornyl derivatives as listed in Table IX below, to the basic blueberry formulation which does not contain any of said norbornyl derivatives.

TABLE IX

| Norbornyl Derivative | Flavor Characteristics |
|---|---|
| Composition produced according to Example II consisting of bulked fractions 4-6 containing the compounds having the structures: 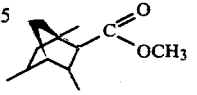 | A fruity, blueberry aroma and taste. |

TABLE IX-continued

| Norbornyl Derivative | Flavor Characteristics |
|---|---|
| and [structure: norbornyl-C(=O)-OCH₃] | |
| The composition of Example III bulked fractions 7 and 8 containing the compounds having the structures: [two norbornyl ester structures] and | A sweet, fruity, berry-like, spicy, black pepper-like, herbaceous and clove-like aroma and taste characteristic. |
| Composition of Example V bulked fractions 6-8 containing the compounds having the structures: [two norbornyl ester structures] and | A sweet, fruity, raspberry, vermouth-like and blueberry aroma profile with a fruity, raspberry and blueberry flavor profile. |
| Composition produced according to Example VI bulked fractions 5-14 containing the compounds having the structures: [two norbornyl ester structures] and | A fruity, strawberry, blueberry, balsamic aroma profile with blueberry, balsamic and bitter profile at 2ppm. |

EXAMPLE XVIII

USE OF NORBORNANE DERIVATIVES FOR RASPBERRY FLAVORS

The following basic raspberry formulation is prepared:

| Ingredients | Parts By Weight |
|---|---|
| Vanillin | 2 |
| Maltol | 4 |
| Parahydroxy benzyl acetone | 5 |
| Dimethyl sulfide | 1 |
| Alpha-ionone (10% in propylene glycol) | 2 |
| Ethyl butyrate | 6 |
| Ethyl acetate | 16 |
| Isobutyl acetate | 14 |
| Acetic acid | 10 |
| Acetaldehyde | 10 |
| Propylene glycol | 930 |
| | 1000 |

The above formulation is split into five parts. Two the first four parts, at the rate of 0.3% are added the norbornyl derivative produced according to the preceeding examples, as set forth in Table X below. No additive is added to the fifth part. The five formulations are compared in water at the rate of 50 ppm. The four flavors containing the norbornyl derivatives have more ripe raspberry tastes and woody, raspberry kernel characters. They also have additional nuances as set forth in Table X below. Therefore the raspberry formulations containing the four norbornyl derivatives as additives have more natural-like and more characteristic raspberry flavors and are therefore preferred.

TABLE X

| Norbornyl Derivative | Flavor Profile |
|---|---|
| Product produced according to Example III, bulked fractions 7 and 8 consisting of compounds having the structures: [two norbornyl ester structures] and | A sweet, fruity, berry-like, spicy, black pepper-like, herbaceous and clove-like aroma and taste. |
| Product produced according to Example IV, bulked fractions 7-12 consisting of the compounds having the structures: [two norbornyl ester structures] and | A sweet, fruity, red berry, raspberry-like and seedy aroma profile with a sweet, fruity, red berry-like, raspberry-like, seedy and strawberry taste profile |
| Product produced according to Example V, bulked fractions 6-8, consisting of the compounds having the structures: [norbornyl ester structure] and | A sweet, fruity, raspberry, vermouth-like and blueberry aroma profile with a fruity, raspberry and blueberry flavor profile. |

TABLE X-continued

| Norbornyl Derivative | Flavor Profile |
|---|---|
| 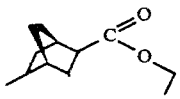 Product produced according to Example VII, bulked fractions 6–9, consisting of the compounds having the structures: 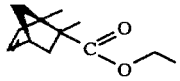 and  | A fruity, raspberry and seedy aroma profile with a fruity, raspberry, seedy and bitter flavor profile |

EXAMPLE XIX

FRUITED TAPIOCA CREAM

The contents of Ann Page Tapioca pudding mix (ingredients: sugar, corn starch, tapioca, sodium chloride, tapioca flavor and artificial color; Net weight 138 grams) is emptied into a sauce pan. Three cups of milk are added together with one beaten egg yolk previously blended therewith. The resulting mix is cooked over medium heat stirring constantly while slowly adding at the rate of 0.2%, either one of the flavor materials of Example XVII (blueberry flavor) or one of the flavor materials of Example XVIII (raspberry flavor) each of the materials containing one of the norbornyl derivatives of Table IX or of Table X as the case may be. The resulting mixture after heating, is then cooled to room temperature in the saucepan. One egg white is slowly added to the resulting mixture together with three tablespoons of sugar. The resulting mixture is then blended and chilled yielding pleasantly tasting blueberry or raspberry tapioca cream deserts depending upon whether the materials of Example XVII or Example XVIII are added.

EXAMPLE XX

FLAVORED INSTANT PUDDING

A pudding mix (Royal Instant, Net weight 3.5 ozs. produced by Standard Brands Inc., New York, New York 10022) is intimately admixed with 2 cups of cold fresh whole milk. To this mixture, at the rate of 0.3%, is added one of the blueberry flavors of Example XVII containing the norbornyl derivative as listed in Table IX or one of the raspberry flavors of Example XVIII containing one of the norbornyl derivatives as listed in Table X. The resulting mixture is blended in a Waring blender for a period of three minutes. The resulting mixture is then cooled at 15° C. for a period of five minutes. The resulting puddings have excellent natural blueberry or natural raspberry flavors as the case may be, depending on whether the blueberry flavors of Example XVII or whether the raspberry flavors of Example XVIII are used.

EXAMPLE XXI

A. POWDER FLAVOR COMPOSITION

20 Grams of one of the flavor compositions of Example XVII (containing at least one of the norbornyl derivatives of Table IX) is emulsified in a solution containing 300 grams gum acacia and 700 grams water. The emulsion is spray-dried with a Bowen Lab Model Drier utilizing 260 c.f.m. of air with an inlet temperature of 500° F., an outlet temperature of 200° F., and a wheel of speed of 50,000 rpm.

B. SUSTAINED RELEASE FLAVOR

The following mixture is prepared:

| Ingredients | Parts by Weight |
|---|---|
| Liquid Blueberry Flavor, composition of Ex. XVII | 20 |
| Propylene glycol | 9 |
| Cab-O-Sil ® M-5 (Brand of Silica produced by the Cabot Corp. of 125 High St. Boston, Mass. 02110; Physical Properties: Surface area: 200 m²/gm Nominal particle size: 0.012 microns Density: 2.3 lbs./cu. ft. | 5.00 |

The Cab-O-Sil is dispersed in the liquid blueberry flavor compositions (containing the norbornyl derivatives) of Example XVII with vigorous stirring, thereby resulting in a viscous liquid. 71 Parts by weight of the powder flavor composition of Part A, supra, is then blended into the said viscous liquid, with stirring, at 25° C. for a period of 30 minutes resulting in a dry, free flowing sustained release flavor powder.

EXAMPLE XXII

10 Parts by weight of 50 Bloom pigskin gelatin is added to 90 parts by weight of water at a temperature of 150° F. The mixture is agitated until the gelatin is completely dissolved and the solution is cooled to 120° F. 20 Parts by weight of the one of the liquid flavor compositions of Example XVII (containing at least one of the norbornyl derivatives of Table IX) is added to the solution which is then homogenized to form an emulsion having particle size typically in the range of 2–5 microns. This material is kept at 120° F. under which conditions the gelatin with not jell.

Coascervation is induced by adding, slowly and uniformyl 40 parts by weight of a 20% aqueous solution of sodium sulphate. During coacervation the gelatin molecules are deposited uniformly about each oil droplet as a nucleus.

Gelatin is effected by pouring the heated coascervate mixture into 1,000 parts by weight of 7% aqueous solution of sodium sulphate at 65° F. The resulting jelled coascervate may be filtered and washed with water at temperatures below the melting point of gelatin, to remove the salt.

Hardening of the filtered cake, in this example, is effected by washing with 200 parts by weight of 37% solution of formaldehyde in water. The cake is then washed to remove residual formaldehyde.

EXAMPLE XXIII

100 Parts by weight of chicle are mixed with 4 parts by weight of the flavor prepared in accordance with Example XXI. 300 Parts of sucrose and 100 parts of corn syrup are added. Mixing is effected in a ribbon blender with jacketed side walls of the type manufactured by the Baker Perkins Co.

The resultant chewing gum blend is then manufactured into strips 1 inch in width and 0.1 inches in thickness. The strips are cut into lengths of 3 inches each. On chewing, the chewing gum as a pleasant, long lasting blue-berry flavor.

EXAMPLE XXIV
CHEWING GUM

100 Parts by weight of chicle are mixed with 18 parts by weight of the flavor prepared in accordance with Example XXII. 300 Parts of sucrose and 100 parts of corn syrup are then added. Mixing is effected in a ribbon blender with jacketed side walls of the type manufactured by the Baker Perkins Co.

The resulting chewing gum blend is then manufactured into strips 1 inch in width and 0.1 inches in thickness. The strips are cut into lengths of 3 inches each. On chewing, the chewing gum has a pleasant, long lasting blueberry flavor.

EXAMPLE XXV
TOOTHPASTE FORMULATION

The following separate groups of ingredients are prepared:

| Parts by Weight | Ingredients |
| --- | --- |
| Group "A" | |
| 30.200 | Glycerine |
| 15.325 | Distilled Water |
| .100 | Sodium Benzoate |
| .125 | Saccharin Sodium |
| .400 | Stannous Fluoride |
| Group "B" | |
| 12.500 | Calcium Carbonate |
| 37.200 | Dicalsium Phosphate (Dihydrate) |
| Group "C" | |
| 2.000 | Sodium N—Lauroyl Sarcosinate (foaming agent) |
| Group "D" | |
| 1.200 | Flavor Material of Ex. XVI |
| 100.00 Total | |

PROCEDURE

1. The ingredients in Group "A" are stirred and heated in a steam jacketed kettle to 160° F.
2. Stirring is continued for an additional three to five minutes to form a homogeneous gel.
3. The powders of Group "B" are added to the gel, while mixing, until a homogeneous paste is formed.
4. With stirring, the flavor of "D" is added and lastly the sodium n-lauroyl sarcosinate.
5. The resultant slurry is then blended for one hour. The completed paste is then transferred to a three roller mill and then homogenized, and finally tubed.

The resulting toothpaste when used in a normal toothbrushing procedure yields a pleasant blueberry flavor, of constant strong intensity throughout said procedure (1-1.5 minutes).

EXAMPLE XXVI
CHEWABLE VITAMIN TABLETS

The flavor material (containing norbornyl derivatives) of Table X of Example XVIII is added to a chewable vitamin tablet formulation at the rate of 10 gm/Kg which chewable vitamin tablet formulation is prepared as follows:

In a Hobart Mixer the following materials are blended to homogeneity:

|  | Gms/1000 Tablets |
| --- | --- |
| Vitamin C (ascorbic acid) as ascorbic acid-sodium ascorbate mixture 1:1 | 70.00 |
| Vitamin $B_1$ (thiamine mononitrate $33\frac{1}{3}\%$ (Hoffman La Roche) | 4.0 |
| Vitamin $B_2$ (roboflavin) as Rocoat® roboflavin $33\frac{1}{3}\%$ | 5.0 |
| Vitamin $B_6$ (pyridoxine hydrochloride) as Rocoat® pyridoxine hydrochloride $33\frac{1}{3}\%$ | 4.0 |
| Niacinamide as Rocoat® niacinamide $33\frac{1}{3}\%$ | 33.0 |
| Calcium pantothenate | 11.5 |
| Vitamin $B_{12}$ (cyanocobalamin) as Merck 0.1% in gelatin | 3.5 |
| Vitamin E (dl-alpha tocopheryl acetate) as dry Vitamin E acetate $33\frac{1}{3}\%$ Roche | 6.6 |
| d-Biotin | 0.044 |
| Flavor of Example XVIII containing norbornyl derivatives of Table X | (as indicated above) |
| Certified lake color | 5.0 |
| Sweetener - sodium saccharin | 1.0 |
| Magnesium stearate lubricant | 10.0 |
| Mannitol q.s. to make | 500.0 |

Preliminary tablets are prepared by slugging with flat-faced punches and grinding the slugs to 14 mesh. 13.5 G dry Vitamin A Acetate and 0.6 g Vitamin D are then added as beadlets. The entire blend is then compressed using concave punches at 0.5 g each.

Chewing of the resultant tablets yields a pleasant long lasting, consistently strong raspberry flavor for a period of 12 minutes.

EXAMPLE XXVII
CHEWING TOBACCO

Onto 100 pounds of tobacco for chewing (85% Wisconsin leaf and 15% Pennsylvania leaf) the following casing is sprayed at a rate of 30%:

| Ingredients | Parts by Weight |
| --- | --- |
| Corn Syrup | 60 |
| Licorice | 10 |
| Glycerine | 20 |
| Fig Juice | 4.6 |
| Prune Juice | 5 |
| Flavor Material of Ex. XVII Containing Norbornyl Derivatives as listed in Table IX | 0.4 |

The resultant product is redried to a moisture content of 20%. On chewing, this tobacco has an excellent substantially consistent, long-lasting blueberry nuance in conjunction with the tobacco note.

EXAMPLE XXVIII

TOBACCO FORMULATION

A tobacco mixture is produced by admixing the following ingredients:

| Ingredient | Parts by Weight |
| --- | --- |
| Bright | 40.1 |
| Burley | 24.9 |
| Maryland | 1.1 |
| Turkish | 11.6 |
| Stem (flue-cured) | 14.2 |
| Glycerine | 2.8 |
| Water | 5.3 |

Cigarettes are prepared from this tobacco. The following flavor formulation is prepared:

| Ingredient | Parts by Weight |
| --- | --- |
| Ethyl butyrate | .05 |
| Ethyl valerate | .05 |
| Maltol | 2.00 |
| Cocoa extract | 26.00 |
| Coffee extract | 10.00 |
| Ethyl alcohol | 20.00 |
| Water | 41.90 |

The above-stated tobacco flavor formulation is applied at the rate of 0.1% to all of the cigarettes produced using the above tobacco formulation. Half of the cigarettes are then treated with 500 to 1,500 ppm of one of the following norbornyl derivatives of Table XI as follows:

TABLE XI

A. Product produced according to Example II, bulked fractions 4–6 consisting of the compounds having the structures:

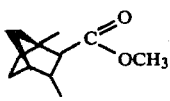

and

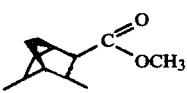

B. Composition of matter produced according to Example III bulked fractions 7 and 8 consisting of the compounds having the structures:

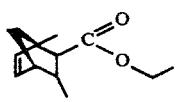

and

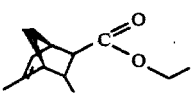

The control cigarettes not containing the norbornyl derivatives as set forth in Table XI and the experimental cigarettes which contain the norbornyl derivatives as set forth in Table XI are evaluated by paired comparison and the results are as follows:

The experimental cigarettes, are found, on smoking, to have a sweeter, spicy, woody-oriental, clove-like taste with much more body and much more natural tobacco-like aroma prior to smoking and on smoking in the mainstream and the sidestream. The experimental cigarettes containing the product produced according to Example II in addition have cooling nuances. The experimental cigarettes produced containing the product produced according to Example III also have cinnamon bark nuances prior to and on smoking in the mainstream and in the sidestream.

All cigarettes are evaluated for smoke flavor with a 20 mm cellulose acetate filter.

Accordingly, it is concluded that the norbornyl derivatives set forth in Table XI produced according to the processes of Examples II and III enhance the tobacco-like taste and aroma particularly the oriental-like taste of the blended cigarette imparting to it sweet, spicy and woody-oriental tobacco-like nuances and in addition clove-like nuances.

EXAMPLE XXIX

The following is a description of a preferred embodiment of the invention as carried out using a process wherein minute capsules having a diameter in the range of 50 up to 500 microns were added to a wet web of reconstituted tobacco (weight ratio of dry web to dry capsules = 1:0.04. The capsules and binder materials (weight ratio of dry capsule to dry binder = 1:0.1 when placed among the tobacco fibers, wet them and entangle with them and clothe them, thus in effect securing and binding the capsules against migration through the sheet, thereby forming a subsident stratum. The majority of binder and associated capsules are caught in the sheet. Substantially no capsules migrate through the sheet. When the wet tobacco web is dried, the binder shrinks by loss of solvent, leaving the dried polymeric binder material, and the capsules remain in place relatively with respect to sheet thickness. The sheets containing the capsules are then shredded and used in producing smoking articles such as cigarettes. Such cigarettes are formed using a wrapper, containing a fill of tobacco extending from one end of the wrapper to the other, and intimately admixed with the tobacco, a plurality of microcapsules each comprising an aromatic volatile synthetic clove oil flavorant. The capsules are homogeneously spaced in contiguous relationship with the tobacco such that as the burning front of the tobacco advances the length of the tobacco article, a concomitant elevation of temperature initiates consecutive rupture of the capsules (1) releasing the volatile synthetic clove oil-containing material which emanates with smoke from the smoking article into the smoker's mouth and (2) yielding a crackling sound audible to the human ear.

Tragacanth gum solution and starch solution were prepared in the following manner:

PART A

Concentrated Tragacanth Gum Solution (Binder)

4.5 Pounds of dry tragacanth gum powder were stirred into 50 gallons of water, using a suitable mixer. Five minutes after all the powder had been added, the mixer was turned off. The tragacanth gum solution was allowed to stir for 2 hours, and then the mixer was turned on for 5 minutes. Sitting for 2 additional hours, enabled the tragacanth gum to hydrate. After five minutes, the mixer was turned off, and the 55 gallon drum was covered. Just prior to combining the tragacanth gum solution and the capsular slurry, 50 gallons of tragacanth gum solution was diluted with water to 3 percent tragacanth gum on a solids basis.

PART B

Starch Solution

The hydrolyzed starch solution was prepared by heating a slurry of the starch at 190 degrees Fahrenheit for a minumum of 15 minutes to provide a 1 percent by weight, starch-in-water solution.

Capsule slurries were prepared in the following manner:

PART C

Preparation of Synthetic Clove Oil

A mixture is prepared containing the following ingredients:

| Ingredient | Percentage |
|---|---|
| α-Caryophyllene | 2.0 |
| β-Caryophyllene | 2.0 |
| γ-Caryophyllene | 10.0 |
| Furfural | 0.1 |
| Eugenol | 65.0 |
| Eugenyl Acetate | 5.0 |
| Acetyl Eugenols | 5.9 |
| Norbornol Derivatives as follows: | |
| A. Product produced according to Example II, bulked fractions 4–6 consisting of the compounds having the structures: 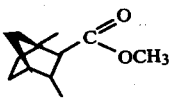 and 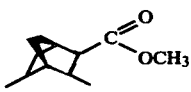 | 5.0 |
| B. Composition of matter produced according to Example III bulked fractions 7 and 8 consisting of the compounds having the structures: 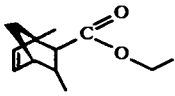 and 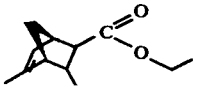 | 5.0 |

PART D

Preparation of Capsular Slurry-Encapsulation of Synthetic Clove Oil

Ten grams of gum arabic were dissolved at room temperature in 220 grams of deionized water. The mixture was agitated until the gum arabic was fully dissolved. In a separate 240 milliliter Erlenmeyer flask, 10.0 grams of modified gelatin was mixed with 220.0 grams of deionized water. The gelatin was allowed to tumefy at room temperature and also then warmed in a water bath in about 40° C. With stirring so that the gelatin was dissolved.

The gelatin solution and the gum arabic solution were poured into a beaker equipped with a stirrer. A flocculence indicating the precipitation of the gelatin was noted. The temperature of the mixture was decreased to 35° C. The speed of the stirrer was adjusted so that it was turning only enough to keep the phases mixed. The pH of the mixture was 4.50.

Into the beaker containing the mixture of gum arabic and gelatin was poured 118.0 grams of synthetic clove oil as prepared in Part C. The speed of the stirrer was then adjusted to mix the colloids and the oil. The oil separated into droplets. Two drops of octyl alcohol were added to prevent foaming. The progress of the coacervation was monitored by means of microscopic examination.

The temperature of the mixture was lowered to room temperature, e.g., 24° C. At the higher temperature of 31° C., colloid deposition was observed on the oil droplets. At 24° C., little colloid could be observed in aqueous portions of the mixture. Deposition had ceased. Stirring was continued for 30 minutes, whereupon the reaction mixture was cooled on an ice bath to 4° C. The reaction mixture was maintained at this temperature for 200 minutes. (When hardening was desired, 1.0 milliliters of a 25 percent glutaraldehyde in water per gram of gelatin is added.)

The internal phase of the capsules thus formed was approximately 80–90 percent of the total weight of the capsules.

The capsules thus produced had diameters in the range of from 50 up to 500 microns. They were coated with the binder onto a tobacco sheet material which was shredded and used as a fill in the manufacture of a smoking article.

PART E

Variation of the Encapsulation of Synthetic Clove Oil

A variation of the encapsulation procedure set forth immediately supra is shown below.

The solution of gum arabic was warmed to 38° C., placed in a Waring blender and stirred. The clove oil prepared in Part C was added gradually while the speed of the blender was being increased until the size of the clove oil droplets was approximately 50–500 microns. The mixture thus formed was poured into a 1,000 milliliter beaker containing gelatin, also at 38° C., and was stirred thoroughly. The temperature was then allowed to drop to room temperature and then further decreased to a temperature of 4° C. to 10° C. by means of an ice bath.

It is evident that the tobacco film or filaments can be made from various types and combinations of tobacco. For instance, the tobacco sheet material can be made from relatively expensive tobacco such as Latakia in which it is highly desirous to use all waste because of the high price thereof. So, also, it may be formed of Burley or one or more scrap or waste cigarette type tobaccos and incorporated in accordance with a particular cigarette manufacture's formula as if it were natural cigarette tobacco leaves. Any desired formula can thus be maintained in accordance with the demands of a manufacturer's particular brand using one or more types of natural shredded tobacco leaves and admixed desired quantities of shredded capsule containing tobacco film material or filaments, either as a blending or flavoring medium or both or for purposes of bulking.

In the case of the manufacture of cigarettes, according to the present invention, tobacco films are shredded into strands or the film is formed directly into filaments substantially the width of the strands of natural shredded tobacco and of any desired length. In the case of cigars, the capsule containing films are use in large pieces much as long filler tobacco and forming long filler cigars. In all cases the shredded film or filaments or film used in cigarettes and cigars can be handled either manually or by machine in the same manner as natural shredded tobacco leaves or whole leaves or portions thereof. The amount of shredded capsule-containing reconstituted tobacco or pieces of this material employed in a particular blend in cigarettes or cigars, respectively, will vary according to types of tobacco used in the sheet material and the requirements of a particular manufacture.

EXAMPLE XXX

PREPARATION OF A DETERGENT COMPOSITION

A total of 100 grams of detergent powder (a low phosphate content detergent composition which contains 12% by weight phosphate builder, 8% hardness mineral ion insensitive detergent, 0.9% by weight maleic anhydride-vinyl compound co-polymer and 2% alkylene oxide condensation product prepared according to Example IV at column XI, of U.S. Pat. No. 4,000,080 issued on Dec. 28, 1976) is intimately admixed with 0.15 grams of one of the perfume materials of Table XII below until a substantially homogeneous composition is obtained. This composition has an aroma as set forth in Table XII below which is pleasant and long lasting:

TABLE XII

| Product | Aroma Profile |
|---|---|
| Product produced according to Example I, bulked fractions 4–7 consisting of compounds having the structures: 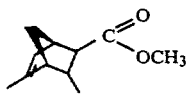 and 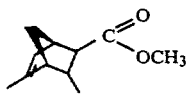 | A fruity, banana and creamy aroma with camphoraceous and minty undertones. |
| Product produced according to Example II, bulked fractions 4–6 consisting of the compounds having the structures: 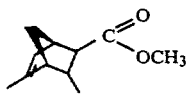 and 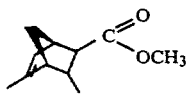 | A fruity, camphoraceous and herbaceous aroma. |
| Product produced according to Example III, bulked fractions 7 and 8 consisting of the compounds having the structures: 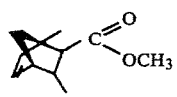 and 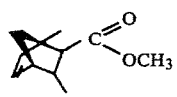 | A sweet, spicy, herbal woody and eucalyptol-like aroma with a distinct calamnus undertone. |
| Product produced according to Example IV, bulked fractions 7–12 consisting of compounds having the structures: 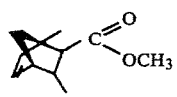 and 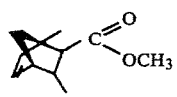 | A sweet, fruity (banana) creamy and minty aroma with the minty nuances increasing in intensity on dryout. |
| Product produced according to Example V, bulked fractions 6–8 consisting of the compounds having the structures: 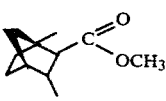 and 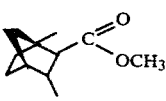 | A fruity, banana and creamy aroma profile. |
| Product produced according to Example VI, bulked fractions 5–14 containing and consisting of the compounds having the structures: 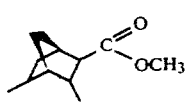 and 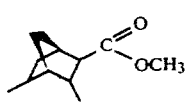 | A rum/butterscotch and balsamic aroma. |
| Product produced according to Example VII, bulked fractions 6–9 consisting of the compounds having the structures: | A green, minty, borneol-like, spicy, somewhat medicinal aroma reminiscent of pepacuana bark extract with strong pepacuana bark-like undertones. |

TABLE XII-continued

| Product | Aroma Profile |
|---|---|
| [structure: bicyclic with C(=O)OEt] and [structure: bicyclic with C(=O)OEt] | |
| Fragrance formulation of Example VIII(A) | A spicy, floral, herbal aroma with pleasant fruity tagette characteristics. |
| Fragrance formulation of Example VIII(B) | A spicy, floral, herbal aroma with pleasant fruity tagette characteristics. |
| Fragrance formulation of Example IX | A jasmine aroma with a pleasant fruityness. |
| Fragrance formulation of Example X | A sweet, floral aroma with excellent fruity floralcy undertones. |

EXAMPLE XXXI

PERFUMED LIQUID DETERGENTS

Concentrated liquid detergents with aromas as set forth in Table XIII below are prepared containing 0.10%, 0.15%, and 0.20% of the perfume ingredients set forth in Table XIII below. They are prepared by adding and homogeneously mixing the appropriate quantity of perfume ingredient set forth in Table XIII below in a liquid detergent which is a homogeneous single-phase heavy duty liquid detergent composition containing:

a. 12.5% by weight based on the free acid form of an anionic detersive surfactant;
b. 0.5% magnesium sulfate;
c. 12% by weight of an ethoxylated nonionic detersive surfactant;
d. 3% by weight of a water-soluble bis(styrylsulfonate)biphenyl brightener; and
e. the balance of the composition being water, prepared according to U.S. Pat. No. 3,998,750 issued on Dec. 21, 1976. The detergents all possess aromas as described in Table XIII below:

TABLE XIII

| Product | Aroma Profile |
|---|---|
| Product produced according to Example I, bulked fractions 4–7 consisting of compounds having the structures: [two bicyclic structures with C(=O)OCH₃] | A fruity, banana and creamy aroma with camphoraceous and minty undertones. |
| Product produced according to Example II, bulked fractions 4–6 consisting of the compounds having the structures: [two bicyclic structures with C(=O)OCH₃] | A fruity, camphoraceous and herbaceous aroma. |
| Product produced according to Example III, bulked fractions 7 and 8 consisting of the compounds having the strucutures: [two bicyclic structures with C(=O)OEt] | A sweet, spicy, herbal woody and eucalyptol-like aroma with a distinct calamnus undertone. |
| Product produced according to Example IV, bulked fractions 7–12 consisting of compounds having the structures: [two bicyclic structures with C(=O)O-isopropyl] | A sweet, fruity (banana) creamy and minty aroma with the minty nuances increasing in intensity on dryout. |
| Product produced according to Example V, bulked fractions 6–8 consisting of the compounds having the structures: [two bicyclic structures with C(=O)O-isobutyl] | A fruity, banana and creamy aroma profile. |
| Product produced according to Example VI, bulked fractions 5–14 contained and consisting of the compounds having the structures: [two bicyclic structures with C(=O)O-propyl] | A rum/butterscotch and balsamic aroma. |

TABLE XIII-continued

| Product | Aroma Profile |
|---|---|
| Product produced according to Example VII, bulked fractions 6-9 consisting of the compounds having the structures: <br><br> and <br>  | A green, minty, borneol-like, spicy, somewhat medicinal aroma reminiscent of pepacuana bark extract with strong pepacuana bark-like undertones. |
| Fragrance formulation of Example VIII(A) | A spicy, floral, herbal aroma with pleasant fruity tagette characteristics. |
| Fragrance formulation of Example VIII(B) | A spicy, floral, herbal aroma with pleasant fruity tagette characteristics. |
| Fragrance formulation of Example IX | A jasmine aroma with a pleasant fruityness. |
| Fragrance formulation of Example X | A sweet, floral aroma with excellent fruity floralcy undertones. |

EXAMPLE XXXII

PREPARATION OF MIXTURE OF ISOPROPYL ESTERS OF 5-METHYL AND 6-METHYL-2-NORBORNANE CARBOXYLIC ACIDS (THERMAL NON-CATALYTIC DIELS-ALDER REACTION)

Reaction:

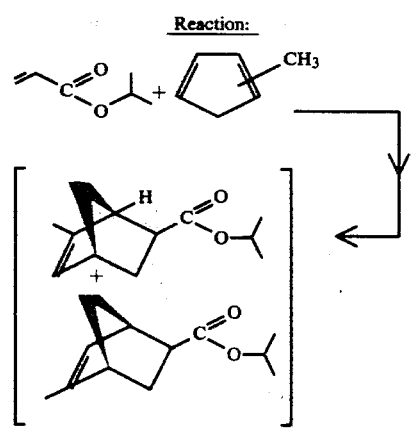

Into a 500 cc high pressure stainless steel autoclave equipped with shaker are placed 140 grams of methylcyclopentadiene dimer, 200 grams of isopropyl acrylate and 1 gram of Ionol ®. The autoclave is closed and heated to 200° C. and maintained at 200° C. for a period of 10 hours. At the end of the 10 hour period, the autoclave is opened and the contents cooled to room temperature.

The reaction mass is then distilled on a fractional distillation column yielding the following fractions:

| Fraction Number | Vapor Temp. °C. | Liquid Temp. °C. | Head Vac. mm Hg. | Reflux Ratio | Weight of Fraction |
|---|---|---|---|---|---|
| 1 | 57/65 | 107/110 | 3.0/2.9 | 9:1 | 14.3 |
| 2 | 65 | 113 | 1.8 | 9:1 | 12 |
| 3 | 65 | 118 | 1.6 | 9:1 | 16 |
| 4 | 68 | 121 | 1.6 | 9:1 | 18 |
| 5 | 68 | 126 | 1.6 | 9:1 | 15.5 |
| 6 | 68 | 138 | 1.6 | 9:1 | 16.8 |
| 7 | 68 | 153 | 1.6 | 9:1 | 17.8 |
| 8 | 72 | 169 | 1.4 | 9:1 | 17.8 |
| 9 | 79 | 177 | 1.4 | 9:1 | 10.1 |
| 10 | 121 | 209 | 2.0 | 9:1 | 8 |
| 11 | 124 | 217 | 2.2 | 9:1 | 14.9 |
| 12 | 128 | 226 | 2.2 | 9:1 | 14.2 |
| 13 | 119 | 250 | 2.2 | 9:1 | 8.6 |

FIG. 34 is the GLC profile of the reaction product prior to distillation (conditions: carbowax column programmed at 80°-220° C. at 8° C. per minute).

FIG. 35-A is the NMR spectrum for Peak 1 of the GLC profile of FIG. 34 containing the compound having the structure:

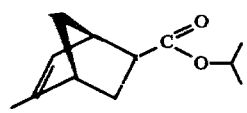

FIG. 35-B is the NMR spectrum for Peak 2 of the GLC profile of FIG. 34 containing the compound having the structure:

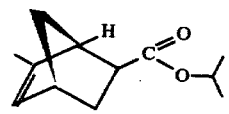

FIG. 36-A is the infra-red spectrum for Peak 1 of the GLC profile of FIG. 34 containing the compound having the structure:

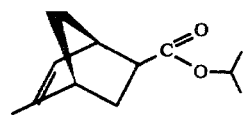

FIG. 36-B is the infra-red spectrum for Peak 2 of the GLC profile of FIG. 34 containing the compound having the structure:

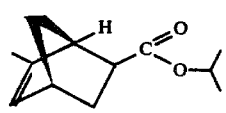

EXAMPLE XXXIII

PREPARATION OF ETHYL ESTER OF 1-; 4-; 5-; and 6-METHYL-2-NORBORNANE-CARBOXYLIC ACIDS (NON-CATALYTIC THERMAL DIELS-ALDER REACTION)

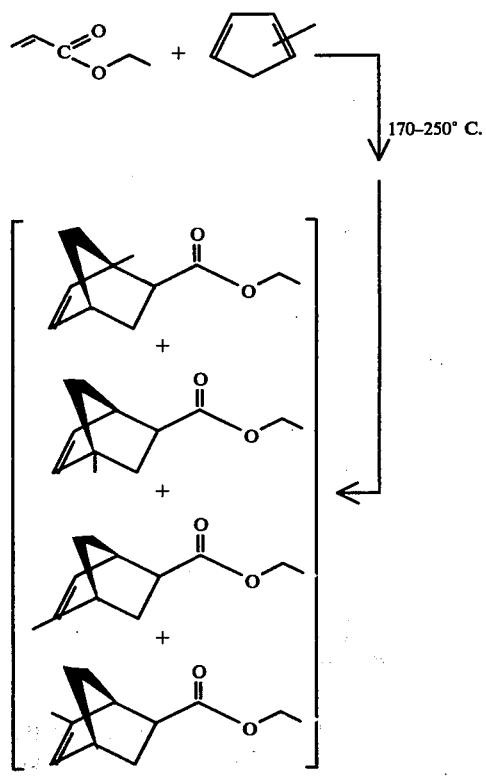

Into a 1 liter autoclave is placed 400 grams of methylcyclopentadiene dimer and 500 grams of ethyl acrylate. The autoclave is closed and the contents are heated with stirring to a temperature of 200° C. and maintained at that temperature for a period of 7 hours. The autoclave pressure is 25 psig. At the end of the 7 hour period, the autoclave is depressurized and opened and the contents cooled to room temperature.

The contents of the autoclave are then distilled on a fractional distillation column yielding the following fractions:

| Fraction Number | Vapor Temp. °C. | Liquid Temp. °C. | Head Vac. mm. Hg. | Reflux Ratio | Weight of Fraction |
|---|---|---|---|---|---|
| 1 | 53/60 | 84/80 | 18/30 | 4:1 | 51 |
| 2 | 60 | 82 | 3.0 | 4:1 | 66 |
| 3 | 60 | 82 | 3.0 | 4:1 | 110 |
| 4 | 62 | 83 | 3.0 | 4:1 | 83 |
| 5 | 67 | 87 | 3.0 | 4:1 | 112 |
| 6 | 67 | 93 | 3.0 | 4:1 | 107 |
| 7 | 62 | 105 | 3.0 | 4:1 | 103 |
| 8 | 62 | 139 | 3.0 | 4:1 | 43 |
| 9 | 66 | 225 | 3.0 | 4:1 | 47 |

FIG. 37 is the GLC profile of the reaction product prior to distillation. Conditions: programmed at 80°-220° C. at 8° C. per minute: SE-30 column.

FIG. 38-A is the NMR spectrum for Fraction 1, Peak 1 of the distillation product of the reaction product of Example XXXIII containing the compounds having the structures:

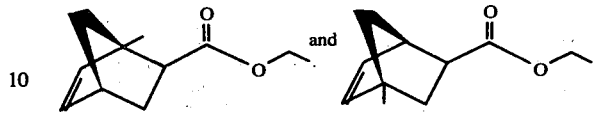

FIG. 38-B is the NMR spectrum for Fraction 8, Peak 2 of the distillation product of the reaction product of Example XXXIII containing the compounds having the structures:

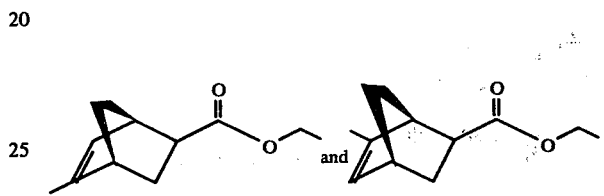

FIG. 39-A is the infra-red spectrum for Fraction 1, Peak 1 of the distillation product of the reaction product of Example XXXIII containing the compounds having the structures:

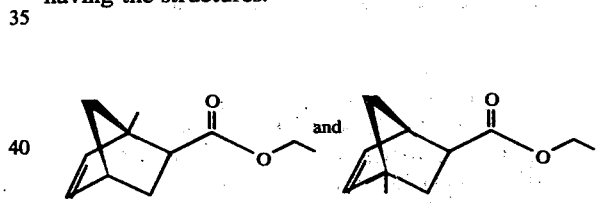

FIG. 39-B is the infra-red spectrum for Fraction 8, Peak 2 of the distillation product of the reaction product of Example XXXIII containing the compounds having the structures:

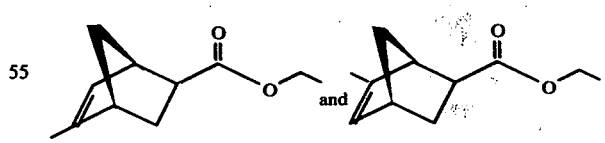

EXAMPLE XXXIV

PREPARATION OF 1-; 4-; 5-; and 6-METHYL NORBORNANE CARBOXYLIC ACID ETHEL ESTERS

Reaction:

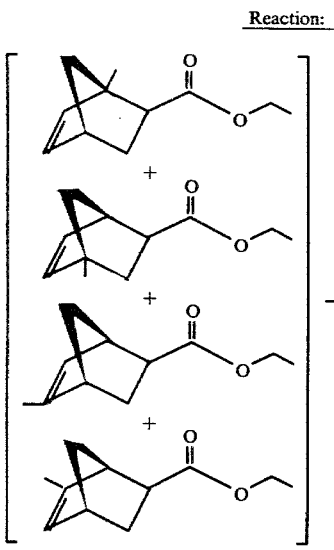

Into a high pressure bottle equipped with Parr shaker is placed 200 grams of the methyl cyclopentadiene-ethyl acrylate reaction product produced according to Example XXXIII; 50 ml isopropyl alcohol and 5 grams of Raney Nickel catalyst. The contents are purged with hydrogen and the bottle is then pressurized to 50 psig. While maintaining the hydrogen pressure at between 20 and 50 psig over a period of 13 hours, the reaction mass is shaken using the Parr shaker. At the end of the 13 hour period the pressure bottle is opened and the reaction mass is distilled on a 12 inch Goodloe column yielding the following fractions:

| Fraction Number | Vapor Temp. °C. | Liquid Temp. °C. | Head Vac. mm. Hg. | Reflux Ratio | Weight of Fraction |
|---|---|---|---|---|---|
| 1 | 49/44 | 78/79 | 2.0/0.8 | 9:1/9:1 | 14.8 |
| 2 | 45 | 80 | .35 | 4:1 | 16.8 |
| 3 | 45 | 80 | .35 | 4:1 | 23.4 |
| 4 | 46 | 80 | .35 | 4:1 | 24.3 |
| 5 | 46 | 80 | .35 | 4:1 | 28.0 |
| 6 | 46 | 87 | .35 | 4:1 | 22.3 |
| 7 | 48 | 88 | .35 | 4:1 | 22.6 |
| 8 | 54 | 88 | .35 | 4:1 | 16.5 |
| 9 | 51 | 112 | .35 | 4:1 | 13.6 |

-continued

| Fraction Number | Vapor Temp. °C. | Liquid Temp. °C. | Head Vac. mm. Hg. | Reflux Ratio | Weight of Fraction |
|---|---|---|---|---|---|
| 10 | 49 | 230 | .35 | 4:1 | 8.6 |

FIG. 40-A is the NMR spectrum for Fraction 2, Peak 1 of the distillation product of the reaction product of Example XXXIV containing the compounds having the structures:

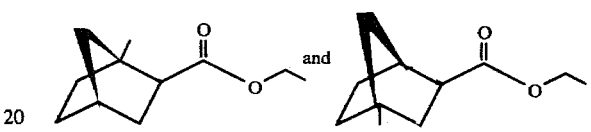

FIG. 40-B is the NMR spectrum for Fraction 10, Peak 2 of the distillation product of the reaction product of Example XXXIV containing the compounds having the structures:

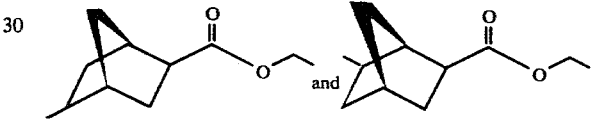

FIG. 41-A is the infra-red spectrum for Fraction 2, Peak 1 of the distillation product of the reaction product of Example XXXIV containing the compounds having the structures:

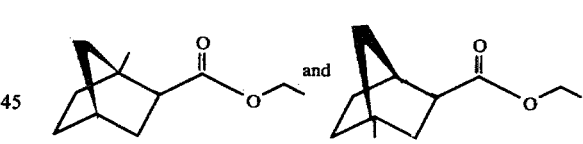

FIG. 41-B is the infra-red spectrum for Fraction 10, Peak 2 of the distillation product of the reaction product of Example XXXIV containing the compounds having the structures:

EXAMPLE XXXV

PREPARATION OF 3,5- AND 3,6-DIMETHYL-2-NORBORNENE CARBOXYLIC ACID ETHYL ESTERS

Reaction:

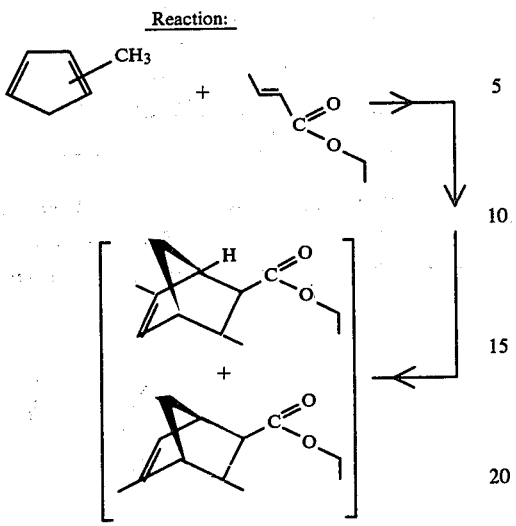

Into a 500 cc autoclave equipped for high pressure reactions is placed 175 grams of methyl cyclopentadiene dimer; 250 grams of ethyl crotonate and 1 gram of Ionol ®. The autoclave is closed and with stirring heated to 200° C. and maintained at 200° C. under pressure for a period of 10 hours. The contents of the autoclave are then cooled to room temperature and the autoclave is opened. The autoclave is then emptied of its contents and the contents are then distilled in an 18″ silver column with Goodloe packing yielding the following fractions:

| Fraction Number | Vapor Temp. °C. | Liquid Temp. °C. | Head Vac. mm. Hg. | Reflux Ratio | Weight of Fraction |
|---|---|---|---|---|---|
| 1 | 37/39 | 100/110 | 1.0/.8 | 9:1 | 19 |
| 2 | 52 | 97 | .8 | 9:1 | 22 |
| 3 | 52 | 97 | .8 | 9:1 | 18 |
| 4 | 50 | 90 | .8 | 9:1 | 19 |
| 5 | 50 | 90 | .8 | 9:1 | 19 |
| 6 | 50 | 91 | .7 | 9:1 | 20 |
| 7 | 50 | 91 | .7 | 9:1 | 20 |
| 8 | 50 | 91 | .7 | 9:1 | 20 |
| 9 | 50 | 93 | .7 | 9:1 | 24 |
| 10 | 50 | 101 | .7 | 9:1 | 22 |
| 11 | 50 | 119 | .7 | 9:1 | 24 |
| 12 | 50 | 124 | .7 | 9:1 | 22 |
| 13 | 50 | 143 | .7 | 9:1 | 23 |
| 14 | 64 | 163 | .7 | 9:1 | 8 |
| 15 | 96 | 230 | .7 | 9:1 | 13 |
| 16 | 109 | 250 | .7 | 9:1 | 10 |

FIG. 42 is the GLC profile of the reaction product prior to distillation.

FIG. 43-A is the NMR spectrum for Peak 1 of the GLC profile of FIG. 42 of the reaction product of Example XXXV containing the compound having the structure:

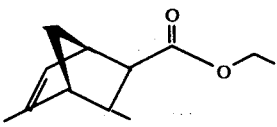

FIG. 43-B is the NMR spectrum for Peak 2 of the GLC profile of FIG. 42 for the reaction product of Example XXXV containing the compound having the structure:

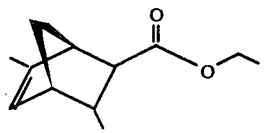

FIG. 44-A is the infra-red spectrum for Peak 1 of the GLC profile of FIG. 42 of the reaction product of Example XXXV containing the compound having the structure:

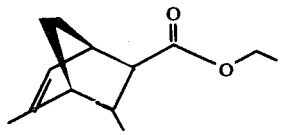

FIG. 44-B is the infra-red spectrum for Peak 2 of the GLC profile of FIG. 42 of the reaction product of Example XXXV containing the compound having the structure:

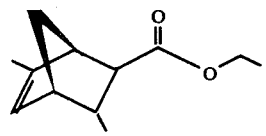

EXAMPLE XXXVI

PREPARATION OF A DETERGENT COMPOSITION

A total of 100 grams of detergent powder (a low phosphate content detergent composition which contains 12% by weight phosphate builder, 8% hardness mineral ion insensitive detergent, 0.9% by weight maleic anhydride-vinyl compound copolymer and 2% alkylene oxide condensation product prepared according to Example IV at column XI, of U.S. Pat. No. 4,000,080 issued on Dec. 8, 1976) is intimately admixed with 0.15 grams of one of the perfume materials of Table XIV below until a substantially homogeneous composition is obtained. This composition has an aroma as set forth in Table XIV below which is pleasant and long lasting:

TABLE XIV

| Product | Aroma Profile |
|---|---|
| Isopropyl ester of 5- and 6-methyl-5-norbornane-2-carboxylic acid (thermal non-catalytic Diels-alder reaction) prepared according to Example XXXII | A green, fruity aroma. |
| Ethyl esters of 1-; 4-; 5-; and 6-methyl-5-norbornane-2-carboxylic acid (thermal non-catalytic Diels-alder reaction) prepared according to Example XXXIII | A sweet, fruity, minty aroma. |
| Ethyl ester of 1-; 4-; 5-; and 6-methyl-norbornane-2-carboxylic acid (thermal non-catalytic Diels-alder reaction) prepared according | A fruity, banana and creamy aroma profile. |

TABLE XIV-continued

| Product | Aroma Profile |
|---|---|
| to Example XXXIV Ethyl esters of 3,5- and 3,6-dimethyl-5-norbornane-2-carboxylic acid (thermal non-catalytic Diels-alder reaction) prepared according to Example XXXV | An intense, fruity, strawberry-like, raspberry-like, reseda body-like aroma but does not have tagett nuances. |

EXAMPLE XXXVII

PERFUMED LIQUID DETERGENTS

Concentrated liquid detergents with aromas as set forth in Table XV below are prepared containing 0.10%, 0.15%, and 0.20% of the perfume ingredients set forth in Table XV below. They are prepared by adding and homogeneously mixing the appropriate quantity of perfume ingredient set forth in Table XV below in a liquid detergent which is a homogeneous single-phase heavy duty liquid detergent composition containing:

a. 12.5% by weight based on the free acid form of an anionic detersive surfactant;
b. 0.5% magnesium sulfate;
c. 12% by weight of an ethoxylated nonionic detersive surfactant;
d. 3% by weight of a water-soluble bis(styrylsulfonate)biphenyl brightener; and
e. the balance of the composition being water, prepared according to U.S. Pat. No. 3,998,750 issued on Dec. 21, 1976. The detergents all possess aromas as described in Table XV below:

TABLE XV

| Product | Aroma Profile |
|---|---|
| Product produced according to Example I, bulked fractions 4-7 consisting of compounds having the structures: 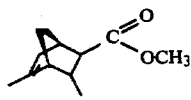 and 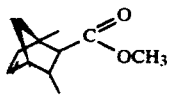 | A fruity, banana and creamy aroma with camphoraceous and minty undertones. |
| Product produced according to Example II, bulked fractions 4-6 consisting of the compounds having the structures: 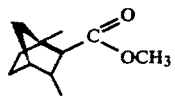 and 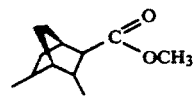 | A fruity, camphoraceous and herbaceous aroma. |
| Product produced according to Example III, bulked fractions 7 and 8 consisting of the compounds having the strucutres: | A sweet, spicy, herbal woody and eucalyptol-like aroma with a distinct calamnus undertone. |

TABLE XV-continued

| Product | Aroma Profile |
|---|---|
| 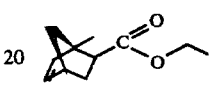 and 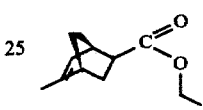 | |
| Product produced according to Example IV, bulked fractions 7-12 consisting of compounds having the structures: 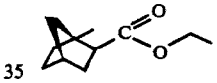 and 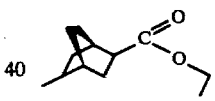 | A sweet, fruity (banana) creamy and minty aroma with the minty nuances increasing in intensity on dryout. |
| Product produced according to Example V, bulked fractions 6-8 consisting of the compounds having the structures: 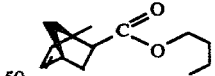 and  | A fruity, banana and creamy aroma profile. |
| Product produced according to Example VI, bulked fractions 5-14 containing and consisting of the compounds having the structures:  and 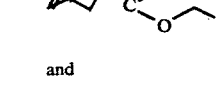 | A rum/butterscotch and balsamic aroma. |
| Product produced according to Example VII, bulked fractions 6-9 consisting of the compounds having the structures: | A green, minty, borneol-like, spicy, somewhat medicinal aroma reminiscent of pepacuana bark extract with strong pepacuana bark-like undertones. |

TABLE XV-continued

| Product | Aroma Profile |
|---|---|
| 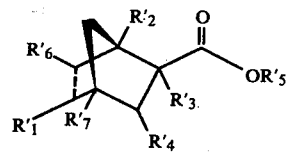 Fragrance formulation of Example VIII (A) | A spicy, floral, herbal aroma with pleasant fruity tagette characteristics. |
| Fragrance formulation of Example VIII (B) | A spicy, floral, herbal aroma with pleasant fruity tagette characteristics. |
| Fragrance formulation of Example IX | A jasmine aroma with a pleasant fruityness. |
| Fragrance formulation of Example X | A sweet, floral aroma with excellent fruity floralcy undertones. |
| Isopropyl ester of 5- and 6-methyl-5-norbornane-2-carboxylic acid (thermal non-catalytic Diels-alder reaction) prepared according to Example XXXII | A green, fruity aroma. |
| Ethyl esters of 1-; 4-; 5-; and 6-methyl-5-norbornane-2-carboxylic acid (thermal non-catalytic Diels-alder reaction) prepared according to Example XXXIII | A sweet, fruity, minty aroma. |
| Ethyl esters of 1-; 4-; 5-; and 6-methyl-norbornane-carboxylic acid (thermal non-catalytic Diels-alder reaction) prepared according to Example XXXIV | A fruity, banana and creamy aroma profile. |
| Ethyl esters of 3,5- and 3,6-dimethyl-5-norbornane-2-carboxylic acid (thermal non-catalytic Diels-alder reaction) prepared according to Example XXXV | An intense, fruity, strawberry-like, raspberry-like, reseda body-like aroma but does not have tagett nuances. |

What is claimed is:

1. A fabric softener composition comprising a fabric softener base and intimately admixed therewith an aroma augmenting or enhancing quantity of at least one compound defined according to the structure:

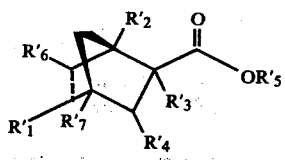

wherein the dashed line represents a carbon-carbon single bond or a carbon-carbon double bond; $R_1'$, $R_2'$, $R_3'$, $R_4'$, $R_6'$, and $R_7'$ are each selected from the group consisting of hydrogen and methyl and $R_5'$ is $C_1$-$C_4$ alkyl with the provisos that:
1. one of $R_1'$, $R_2'$, $R_6'$ and $R_7'$ is methyl and the other of $R_1'$, $R_2'$, $R_6'$ and $R_7'$ represents hydrogen;
2. $R_3'$ and $R_4'$ are not both methyl;
3. when the dashed line is a carbon-carbon double bond, $R_1'$, $R_3'$ and $R_4'$ are not all hydrogen when $R_2'$ is methyl.

2. A process for augmenting or enhancing the aroma of a dryer-added fabric softener article or an aroma imparted by a dryer-added fabric softener article comprising the step of adding to at least one component of a dryer-added fabric softener article and aroma augmenting or enhancing quantity of at least one compound defined according to the generic structure:

wherein the dashed line represents a carbon-carbon single bond or a carbon-carbon double bond; $R_1'$, $R_2'$, $R_3'$, $R_4'$, $R_6'$, and $R_7'$ are each selected from the group consisting of hydrogen and methyl and $R_5'$ is $C_1$-$C_4$ alkyl with the provisos that:
1. one of $R_1'$, $R_2'$, $R_6'$ and $R_7'$ is methyl and the other of $R_1'$, $R_2'$, $R_6'$ and $R_7'$ represents hydrogen;
2. $R_3'$ and $R_4'$ are not both methyl;
3. when the dashed line is a carbon-carbon double bond, $R_1'$, $R_3'$ and $R_4'$ are not all hydrogen when $R_2'$ is methyl.

* * * * *